United States Patent
Lavey et al.

(10) Patent No.: US 7,683,088 B2
(45) Date of Patent: Mar. 23, 2010

(54) COMPOUNDS FOR THE TREATMENT OF INFLAMMATORY DISORDERS

(75) Inventors: Brian J. Lavey, New Providence, NJ (US); Joseph A. Kozlowski, Princeton, NJ (US); Guowei Zhou, Livingston, NJ (US); Ling Tong, Warren, NJ (US); Wensheng Yu, Edison, NJ (US); Michael K. C. Wong, North Brunswick, NJ (US); Bandarpalle B. Shankar, Branchburg, NJ (US); Neng-Yang Shih, Warren, NJ (US); M. Arshad Siddiqui, Newton, MA (US); Kristin E. Rosner, Watertown, MA (US); Chaoyang Dai, Acton, MA (US); Janeta Popovici-Muller, Waltham, MA (US); Vinay M. Girijavallabhan, Watertown, MA (US); Dansu Li, Watertown, MA (US); Aneta M. Micula, South Amboy, NJ (US); Seong-Heon Kim, Livingston, NJ (US); De-Yi Yang, Morris Plains, NJ (US); Razia Rizvi, Bloomfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/653,798

(22) Filed: Jan. 16, 2007

(65) Prior Publication Data

US 2007/0265299 A1 Nov. 15, 2007

Related U.S. Application Data

(60) Provisional application No. 60/759,300, filed on Jan. 17, 2006.

(51) Int. Cl.
| | |
|---|---|
| A61K 31/4166 | (2006.01) |
| A61K 31/4035 | (2006.01) |
| A61K 31/343 | (2006.01) |
| C07D 233/02 | (2006.01) |
| C07D 209/46 | (2006.01) |
| C07D 307/87 | (2006.01) |

(52) U.S. Cl. .................... 514/389; 514/416; 514/418; 514/455; 514/469; 548/311.1; 548/312.1; 548/317.1; 548/455; 549/462

(58) Field of Classification Search ............... 514/416, 514/418, 389, 469; 548/311.1, 311.4, 312.1, 548/317.1, 455; 549/462
See application file for complete search history.

(56) References Cited

U.S. PATENT DOCUMENTS

| | | | |
|---|---|---|---|
| 6,495,565 B2 | 12/2002 | Duan et al. | |
| 6,534,491 B2 | 3/2003 | Levin et al. | |
| 6,677,355 B1 | 1/2004 | Conrad et al. | |
| 7,482,370 B2 | 1/2009 | Yu et al. | |
| 7,488,745 B2 | 2/2009 | Yu et al. | |
| 7,504,424 B2 | 3/2009 | Yu et al. | |
| 7,524,842 B2 | 4/2009 | Lavey et al. | |
| 2004/0067996 A1 | 4/2004 | Sheppeck | |
| 2006/0205797 A1* | 9/2006 | Yu et al. | 514/373 |
| 2008/0226618 A1 | 9/2008 | Mansoor et al. | |
| 2009/0111803 A1 | 4/2009 | Yu et al. | |
| 2009/0137586 A1 | 5/2009 | Yu et al. | |
| 2009/0156586 A1 | 6/2009 | Lavey et al. | |
| 2009/0170875 A1 | 7/2009 | Yu et al. | |

FOREIGN PATENT DOCUMENTS

| | | |
|---|---|---|
| WO | WO2002/074750 | 9/2002 |
| WO | WO2002/096426 | 12/2002 |
| WO | WO2003/053940 | 7/2003 |
| WO | WO2003/053941 | 7/2003 |
| WO | WO2004/012663 | 2/2004 |
| WO | WO2004/024698 | 3/2004 |
| WO | WO2004/024715 | 3/2004 |
| WO | WO2004/024721 | 3/2004 |
| WO | WO 2004/024721 | 3/2004 |
| WO | WO2004/056766 | 7/2004 |
| WO | WO2006/019768 | 2/2006 |
| WO | WO 2006/019768 | 2/2006 |

OTHER PUBLICATIONS

Vippagunta et al., Advanced Drug Dellivery Reviews, p. 1.*
Knaggs, A., et al., "Biotransformation of Alosetron: Mechanism of Hydantoin Formation", Tetrahedron Letters, vol. 36, No. 3, pp. 477-480 (1995).
PCT International Search Report dated Jun. 18, 2007 for corresponding PCT Application No. PCT/US2007/001030.

* cited by examiner

*Primary Examiner*—Yong Chu
(74) *Attorney, Agent, or Firm*—Krishna G. Banerjee; Eric A. Meade

(57) ABSTRACT

This invention relates to compounds of the Formula (I):

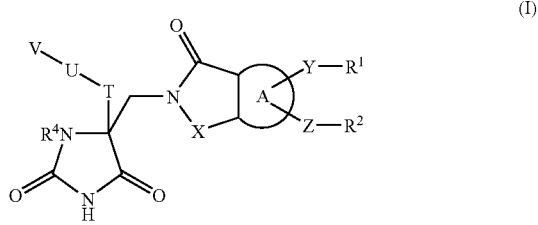

or a pharmaceutically acceptable salt, solvate or isomer thereof, which can be useful for the treatment of diseases or conditions mediated by MMPs, ADAMs, TACE, aggrecanase, TNF-α or combinations thereof.

19 Claims, No Drawings

COMPOUNDS FOR THE TREATMENT OF INFLAMMATORY DISORDERS

This Application claims the benefit of U.S. Provisional Application Ser. No. 60/759,300 filed Jan. 17, 2006, which is incorporated herein by reference in its entirety.

BACKGROUND OF THE INVENTION

1. Field of the Invention

This invention relates generally to novel hydantoin derivatives that can inhibit matrix metalloproteinases (MMPs), a disintegrin and metalloproteases (ADAMs) and/or tumor necrosis factor alpha-converting enzyme (TACE) and in so doing prevent the release of tumor necrosis factor alpha (TNF-α), pharmaceutical compositions comprising such compounds, and methods of treatment using such compounds.

2. Description

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A (1970) 424-434). There are four classes of protein degradative enzymes in mammalian cells: serine, cysteine, aspartic and metalloproteases. The available evidence supports the belief that it is the metalloproteases that are responsible for the degradation of the extracellular matrix of articullar cartilage in OA and RA. Increased activities of collagenases and stromelysin have been found in OA cartilage and the activity correlates with severity of the lesion (Mankin et al. Arthritis Rheum. 21, 1978, 761-766, Woessner et al. Arthritis Rheum. 26, 1983, 63-68 and Ibid. 27, 1984, 305-312). In addition, aggrecanase (a newly identified metalloprotease) has been identified that provides the specific cleavage product of proteoglycan, found in RA and OA patients (Lohmander L. S. et al. Arthritis Rheum. 36, 1993, 1214-22).

Metalloproteases (MPs) have been implicated as the key enzymes in the destruction of mammalian cartilage and bone. It can be expected that the pathogenesis of such diseases can be modified in a beneficial manner by the administration of MP inhibitors (see Wahl et al. Ann. Rep. Med. Chem. 25, 175-184, AP, San Diego, 1990).

MMPs are a family of over 20 different enzymes that are involved in a variety of biological processes important in the uncontrolled breakdown of connective tissue, including proteoglycan and collagen, leading to resorption of the extracellular matrix. This is a feature of many pathological conditions, such as RA and OA, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitor of MPs), which form inactive complexes with the MMP's.

Tumor necrosis factor alpha (TNF-α) is a cell-associated cytokine that is processed from a 26 kDa precursor form to a 17 kd active form. See Black R. A. "Tumor necrosis factor-alpha converting enzyme" Int J Biochem Cell Biol. 2002 January; 34(1):1-5 and Moss M L, White J M, Lambert M H, Andrews RC. "TACE and other ADAM proteases as targets for drug discovery" Drug Discov Today. 2001 Apr. 1; 6(8): 417-426, each of which is incorporated by reference herein.

TNF-α has been shown to play a pivotal role in immune and inflammatory responses. Inappropriate or over-expression of TNF-α is a hallmark of a number of diseases, including RA, Crohn's disease, multiple sclerosis, psoriasis and sepsis. Inhibition of TNF-α production has been shown to be beneficial in many preclinical models of inflammatory disease, making inhibition of TNF-α production or signaling an appealing target for the development of novel anti-inflammatory drugs.

TNF-α is a primary mediator in humans and animals of inflammation, fever and acute phase responses, similar to those observed during acute infection and shock. Excess TNF-α has been shown to be lethal. Blocking the effects of TNF-α with specific antibodies can be beneficial in a variety of conditions, including autoimmune diseases such as RA (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Compounds that inhibit the production of TNF-α are therefore of therapeutic importance for the treatment of inflammatory disorders. Recently it has been shown that metalloproteases, such as TACE, are capable of converting TNF-α from its inactive to active form (Gearing et al Nature, 1994, 370, 555). Since excessive TNF-α production has been noted in several disease conditions also characterized by MMP-mediated tissue degradation, compounds which inhibit both MMPs and TNF-α production may also have a particular advantage in diseases where both mechanisms are involved.

One approach to inhibiting the harmful effects of TNF-α is to inhibit the enzyme, TACE before it can process TNF-α to its soluble form. TACE is a member of the ADAM family of type I membrane proteins and mediates the ectodomain shedding of various membrane-anchored signaling and adhesion proteins. TACE has become increasingly important in the study of several diseases, including inflammatory disease, because of its role in cleaving TNF-α from its "stalk" sequence and thus releasing the soluble form of the TNF-α protein (Black R. A. Int J Biochem Cell Biol. 2002 34, 1-5).

There are numerous patents and publications which disclose hydroxamate, sulphonamide, hydantoin, carboxylate and/or lactam based MMP inhibitors.

U.S. Pat. No. 6,677,355 and U.S. Pat. No. 6,534,491 (B2), describe compounds that are hydroxamic acid derivatives and MMP inhibitors.

U.S. Pat. No. 6,495,565 discloses lactam derivatives that are potential inhibitors of MMPs and/or TNF-α.

PCT Publications WO2002/074750, WO2002/096426, WO20040067996, WO2004012663, WO200274750 and WO2004024721 disclose hydantoin derivatives that are potential inhibitors of MMPs.

PCT Publications WO2004024698 and WO2004024715 disclose sulphonamide derivatives that are potential inhibitors of MMPs.

PCT Publications WO2004056766, WO2003053940 and WO2003053941 also describe potential inhibitors of TACE and MMPSs.

PCT Publication WO2006/019768 refers to hydantoin derivatives that are TACE inhibitors.

There is a need in the art for inhibitors of MMPs, ADAMs, TACE, and TNF-α, which can be useful as anti-inflammatory compounds and cartilage protecting therapeutics. The inhibition of TNF-α, TACE and or other MMPs can prevent the degradation of cartilage by these enzymes, thereby alleviating the pathological conditions of OA and RA as well as many other auto-immune diseases.

SUMMARY OF THE INVENTION

In its many embodiments, the present invention provides a novel class of compounds as inhibitors of TACE, the production of TNF-α, MMPs, ADAMs, aggrecanase, or any combination thereof, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with TACE, aggrecanase TNF-α, MMPs, ADAMs or any combination thereof using such compounds or pharmaceutical compositions.

In one embodiment, the present application discloses a compound, or pharmaceutically acceptable salts or solvates of said compound, said compound having the general structure shown in Formula (I):

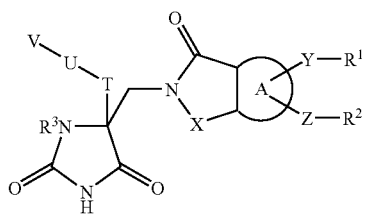

(I)

or a pharmaceutically acceptable salt, solvate, or ester thereof, wherein:

ring A is selected from the group consisting of aryl and heteroaryl, each of which is substituted with —Y—$R^1$ and -Z-$R^2$ as shown;

X is selected from the group consisting of —S—, —O—, —S(O)$_2$, —S(O)—, —(C($R^3$)$_2$)$_m$— and —N($R^3$)—;

T is absent or present, and if present, T is selected from the group consisting of alkyl, aryl, and heteroaryl, wherein when each of said T aryl and heteroaryl contains two radicals on adjacent carbon atoms, said radicals may optionally be taken together with the carbon atoms to which they are attached to form a five- to eight-membered aryl or heteroaryl ring, wherein each of the aforementioned T aryl, and heteroaryl, optionally with said five- to eight-membered aryl or heteroaryl is independently unsubstituted or substituted with one to four $R^{10}$ moieties which can be the same or different;

U is absent or present or absent, and if present, U is selected from the group consisting of —O—, —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-;

V is absent or present, and if present V is selected from the group consisting of alkyl, alkynyl, cycloalkyl, heterocyclyl, aryl, heteroaryl, and N-oxides of said heterocyclyl and heteroaryl, wherein when each of said V cycloalkyl, heterocyclyl, aryl, heteroaryl, and N-oxides of said heterocyyl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said V alkyl, alkynyl, cycloalkyl, heterocyclyl, aryl, and heteroaryl heterocyclyl, optionally with said five- to eight-membered cycloalkyl, aryl, heterocyclyl, or heteroaryl is independently unsubstituted or substituted with one to four $R^{10}$ moieties which can be the same or different;

Y is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)—S(O)$_2$—, —O—, —S—, —C(O)—, —S(O)—, and —S(O)$_2$—;

Z is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)—S(O)$_2$—, —O—, —S—, —C(O)—, —S(O)—, and —S(O)$_2$—;

m is 1 to 3;

n is 1 to 3;

$R^1$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the $R^1$ alkyl, alkynyl, aryl, heteroaryl, and heterocyclyl, optionally with the five or six-membered cycloalkyl, aryl, heterocyclyl or heteroaryl ring is unsubstituted or optionally independently substituted with one to four $R^{20}$ moieties which can be the same or different; with the proviso that when Y is —N($R^4$)—, —S— or —O—, then $R^1$ is not halogen or cyano;

$R^2$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the $R^2$ alkyl, cycloalkyl, aryl, heteroaryl, and heterocyclyl, optionally with the five or six-membered cycloalkyl, aryl, heterocyclyl or heteroaryl ring is unsubstituted or optionally independently substituted with one to four $R^{20}$ moieties which can be the same or different; with the proviso that when Y is —N($R^4$)—, —S— or —O—, then $R^2$ is not halogen or cyano;

each $R^3$ is the same of different and is independently selected from the group consisting of H, alkyl, and aryl;

each $R^4$ is the same or different and is independently selected from the group consisting of H, alkyl, cycloalkyl, haloalkyl, hydroxy, -alkylcycloalkyl, -alkyl-N(alkyl)$_2$, heterocyclyl, aryl, and heteroaryl, wherein when each of said cycloalkyl, heterocyclyl, aryl, and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring;

$R^{10}$ is selected from the group consisting of hydrogen, cyano, nitro, —C($R^4$)=N—O$R^4$, —O$R^4$, —S$R^4$, —N($R^4$)$_2$, —S(O)$R^4$, —S(O)$_2R^4$, —N($R^4$)S(O)$_2R^4$, —N($R^4$)—C(O)—$R^4$, —N($R^4$)—C(O)—N($R^4$)$_2$, —N($R^4$)—C(O)—O$R^4$, —OC(O)N($R^4$)$_2$, —C(O)N($R^4$)—S(O)$_2R^4$, —S(O)$_2$N(R$_4$)—C(O)—$R^4$, —C(O)N($R^4$)C(O)$R^4$, —C(O)N($R^4$)C(O)N$R^4$, —S(O)$_2$N($R^4$)$_2$, —N($R^4$)—C(=N$R^4$)—N($R^4$)$_2$, —N($R^4$)—C(=N—CN)—N($R^4$)$_2$, -haloalkoxy, —C(O)O$R^4$, —C(O)$R^4$, —C(O)N($R^4$)$_2$, halogen, alkyl, haloalkyl, aryl, heteroaryl, heterocyclyl, and cycloalkyl, wherein each of the $R^{10}$ alkyl, aryl, heteroaryl, heterocyclyl, and cycloalkyl is unsubstituted or optionally independently substituted with one to four $R^{30}$ moieties which can be the same or different;

or wherein two $R^{10}$ moieties, when attached to the same or adjacent carbon atoms may optionally be taken together with the carbon atom(s) to which they are attached to form a cycloalkyl, cycloalkenyl, heterocyclyl, aryl, or heteroaryl ring;

$R^{20}$ is selected from the group consisting of cyano, nitro, —C($R^4$)=N—O$R^4$, —O$R^4$, —S$R^4$, —N($R^4$)$_2$, —S(O)$R^4$, —S(O)$_2R^4$, —N($R^4$)S(O)$_2R^4$, —N($R^4$)—C(O)—$R^4$, —N($R^4$)—C(O)—N($R^4$)$_2$, —N($R^4$)—C(O)—O$R^4$, —OC(O)N($R^4$)$_2$, —C(O)N($R^4$)—S(O)$_2R^4$, —S(O)$_2$N($R^4$)—C(O)—$R^4$, —C(O)N($R^4$)C(O)$R^4$, —C(O)N($R^4$)C(O)N$R^4$, —S(O)$_2$N($R^4$)$_2$, —N($R^4$)—C(=N$R^4$)—N($R^4$)$_2$, —N($R^4$)—C(=N—CN)—N($R^4$)$_2$, -haloalkoxy, —C(O)O$R^4$, —C(O)$R^4$, —C(O)N($R^4$)$_2$, halogen, alkyl, haloalkyl, aryl, heteroaryl, heterocyclyl, and cycloalkyl; wherein when each of said $R^{20}$ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said $R^{20}$ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, hydroxyalkyl, cyano, nitro, —NH$_2$, —NH(alkyl), and —N(alkyl)$_2$;

or when two $R^{20}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

$R^{30}$ is selected from the group consisting of cyano, nitro, —C($R^4$)=N—O$R^4$, —O$R^4$, —S$R^4$, —N($R^4$)$_2$, —S(O)$R^4$, —S(O)$_2R^4$, —N($R^4$)S(O)$_2R^4$, —N($R^4$)—C(O)—$R^4$, —N($R^4$)—C(O)—N($R^4$)$_2$, —N($R^4$)—C(O)—O$R^4$, —OC(O)N($R^4$)$_2$, —C(O)N($R^4$)—S(O)$_2R^4$, —S(O)$_2$N($R^4$)—C(O)—$R^4$, —C(O)N($R^4$)C(O)$R^4$, —C(O)N($R^4$)C(O)N$R^4$, —S(O)$_2$N($R^4$)$_2$, —N($R^4$)—C(=N$R^4$)—N($R^4$)$_2$, —N($R^4$)—C(=N—CN)—N($R^4$)$_2$, -haloalkoxy, —C(O)O$R^4$, —C(O)$R^4$, —C(O)N($R^4$)$_2$, halogen, alkyl, haloalkyl, aryl, heteroaryl, heterocyclyl, and cycloalkyl; wherein when each of said $R^{30}$ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said $R^{30}$ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, cyano, nitro, —NH$_2$, —NH(alkyl), and —N(alkyl)$_2$;

or when two $R^{30}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

with the proviso that at least one of T, U, and V must be present; and further that at least one of conditions (1)-(5) below are satisfied:

(1) at least one of T and V is present, and V is other than alkynyl;

wherein said T or V is substituted with at least one $R^{10}$ moiety selected from the group consisting of cyano, —C(O)O$R^4$, —C(O)$R^4$, —C(O)N($R^4$)$_2$, —C(O)N($R^4$)C(O)$R^4$, —C(O)N($R^4$)C(O)N$R^4$, —S$R^4$, —S(O)$_2R^4$, —N($R^4$)—C(O)O$R^4$, —OC(O)N($R^4$)$_2$, —N($R^4$)C(O)N($R^4$)$_2$, —N($R^4$)—C(O)—$R^4$, —S(O)$_2$N($R^4$)$_2$, —S(O)$_2$N($R_4$)—C(O)—$R^4$, —N($R^4$)—C(=N$R^4$)—N($R^4$)$_2$, —N($R^4$)—C(=N—CN)—N($R^4$)$_2$, and —C($R^4$)=N—O$R^4$, wherein each $R^4$ independently is selected from the group consisting of H, alkyl, cycloalkyl, heterocyclyl, aryl, and heteroaryl, wherein when each of said $R^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)$_2R^4$, V is other than piperidinyl, and when $R^{10}$ is cyano, the compound of Formula (I) is other than

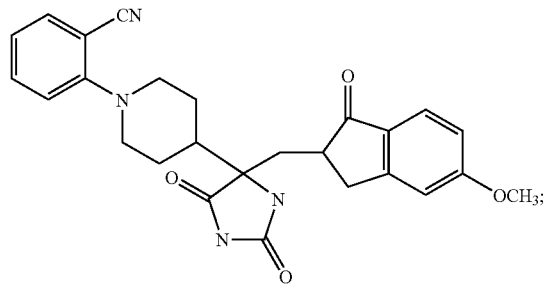

(2) U is present and is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-;

(3) each of —Y—$R^1$ and -Z-$R^2$ is independently selected from the group consisting of cyano, —(C($R^4$)$_2$)$_n$—C(O)OH, —(C($R^4$)$_2$)$_n$—C(O)O-alkyl, —(C($R^4$)$_2$)$_n$—C(O)NH$_2$, —(C($R^4$)$_2$)$_n$—C(O)NH(alkyl), and —(C($R^4$)$_2$)$_n$—C(O)N(alkyl)$_2$. wherein each $R^4$ independently is H or alkyl; and n is 1-3;

(4) T is aryl or heteroaryl, each of which is optionally substituted with one to four independently selected $R^{10}$ moieties, and V is alkynyl which is optionally substituted with one or two independently selected $R^{10}$ moieties; and (5) ring A is heteroaryl, and V is other than alkynyl.

In another embodiment, the present application discloses a compound, or pharmaceutically acceptable salts or solvates of said compound, said compound having the general structure shown in Formula (II):

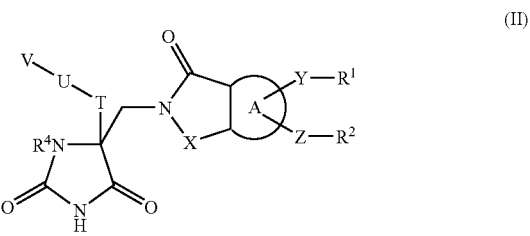

(II)

or a pharmaceutically acceptable salt, solvate, ester or isomer thereof, wherein:

the ring labeled A is selected from the group consisting of aryl and heteroaryl, each of which is substituted with —Y—$R^1$ and -Z-$R^2$ as shown;

X is selected from the group consisting of —S—, —O—, —C($R^3$)$_2$— or —N($R^3$)—;

T is absent or present, and if present, T is selected from the group consisting of H (with U and V being absent), alkyl, alkenyl, alkynyl, aryl, heteroaryl, heterocyclyl, cycloalkyl, alkylaryl-, and arylalkyl-, said aryl, heteroaryl, heterocyclyl, cycloalkyl, alkylaryl-, and arylalkyl- being optionally fused with one or more moieties selected from the group consisting of aryl, heteroaryl, heterocyclyl, cycloalkyl, alkylaryl and arylalkyl, wherein each of any of the aforementioned alkyl, alkenyl, aryl, heteroaryl, heterocyclyl, cycloalkyl, alkylaryl and arylalkyl groups of T is unsubstituted or optionally independently substituted with one to four $R^{10}$ moieties which can be the same or different, each $R^{10}$ moiety being independently selected from the group of $R^{10}$ moieties below;

U is absent or present, and if present U is selected from the group consisting of alkynyl, —C(O)—, —C(O)O—, and —C(O)N$R^4$—;

V is absent or present, and if present V is selected from the group consisting of hydrogen, alkyl, aryl, heteroaryl, heterocyclyl, heterocyclylalkyl-, cycloalkyl, alkylaryl-, and arylalkyl-, said aryl, heteroaryl, heterocyclyl, heterocyclylalkyl-, cycloalkyl, alkylaryl- and arylalkyl- being optionally fused with one or more moieties selected from the group consisting of aryl, heteroaryl, heterocyclyl, cycloalkyl, alkylaryl and arylalkyl, wherein each of any of the aforementioned alkyl, aryl, heteroaryl, heterocyclyl and cycloalkyl is unsubstituted or optionally independently substituted with one to four $R^{10}$ moieties which can be the same or different, each $R^{10}$ moiety being independently selected from the group of $R^{10}$ moieties below;

Y is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)—S(O)$_2$—, —O—, —S—, —C(O)—, —S(O)—, and —S(O)$_2$—;

Z is selected from the group consisting of a covalent bond, —(C($R^4$)$_2$)$_n$—, —N($R^4$)—, —C(O)N($R^4$)—, —N($R^4$)C(O)—, —N($R^4$)C(O)N($R^4$)—, —S(O)$_2$N($R^4$)—, —N($R^4$)—S(O)$_2$—, —O—, —S—, —C(O)—, —S(O)—, and —S(O)$_2$—;

n is 1 to 3;

$R^1$ is selected from the group consisting of H, —O$R^4$, cyano, —C(O)O$R^4$, —C(O)N($R^4$)$_2$, halogen, alkyl, fluoroalkyl, aryl, heteroaryl, heterocyclyl, alkylaryl, alkylheteroaryl and arylalkyl, wherein each of the alkyl, fluoroalkyl, aryl, heteroaryl, heterocyclyl, alkylaryl, alkylheteroaryl and arylalkyl groups of $R^1$ is unsubstituted or optionally independently substituted with one to four $R^{20}$ moieties which can be the same or different, each $R^{20}$ moiety being independently selected from the group of $R^{20}$ moieties below, with the proviso that when Y is present and Y is N, S or O, then $R^1$ is not halogen or cyano;

$R^2$ is selected from the group consisting of H, —O$R^4$, cyano, —C(O)O$R^4$, —C(O)N($R^4$)$_2$, halogen, alkyl, fluoroalkyl, aryl, heteroaryl, heterocyclyl, alkylaryl, alkylheteroaryl and arylalkyl, wherein each of the alkyl, fluoroalkyl, aryl, heteroaryl, heterocyclyl, alkylaryl, alkylheteroaryl and arylalkyl groups of $R^2$ is unsubstituted or optionally independently substituted with one to four $R^{20}$ moieties which can be the same or different, each $R^{20}$ moiety being independently selected from the group of $R^{20}$ moieties below, with the proviso that when Z is present and Z is N, S or O, then $R^2$ is not halogen;

each $R^3$ is the same of different and is independently selected from the group consisting of H, alkyl, and aryl;

each $R^4$ is the same or different and is independently selected from the group consisting of H, alkyl, heterocyclyl, aryl, and heteroaryl;

$R^{10}$ is selected from the group consisting of cyano, —O$R^4$, —S$R^4$, —N($R^4$)$_2$, —S(O)$R^4$—, —S(O)$_2R^4$—, —N($R^4$)S(O)$_2R^4$, —S(O)$_2$N($R^4$)$_2$, —O(fluoroalkyl), —C(O)O$R^4$, —C(O)N($R^4$)$_2$, halogen, alkyl, fluoroalkyl, aryl, heteroaryl, heterocyclyl, cycloalkyl, alkylaryl and arylalkyl, wherein each of the alkyl, fluoroalkyl, aryl, heteroaryl, heterocyclyl, cycloalkyl, alkylaryl and arylalkyl groups of $R^{10}$ is unsubstituted or optionally independently substituted with one to four $R^{30}$ moieties which can be the same or different, each $R^{30}$ moiety being independently selected from the group of $R^{30}$ moieties below;

$R^{20}$ is selected from the group consisting of halogen, alkyl, fluoroalkyl, —N($R^4$)$_2$, and —C(O)N($R^4$)$_2$; and $R^{30}$ is selected from the group consisting of halogen, alkyl, fluoroalkyl, —N($R^4$)$_2$, and —C(O)N($R^4$)$_2$.

The compounds of Formula I can be useful as inhibitors of TACE and may be useful in the treatment and prevention of diseases associated with TACE, TNF-α, MMPs, ADAMs or any combination thereof.

DETAILED DESCRIPTION OF THE INVENTION

In its several embodiments, the present invention provides a novel class of inhibitors of TACE, aggrecanase, the production of TNF-α, MMPs, ADAMs or any combination thereof, pharmaceutical compositions containing one or more of the compounds, methods of preparing pharmaceutical formulations comprising one or more such compounds, and methods of treatment, prevention or amelioration of one or more of the symptoms of inflammation.

In one embodiment, the present invention provides compounds which are represented by structural Formula (I) or (II) above or a pharmaceutically acceptable salt, solvate, ester or isomer thereof, wherein the various moieties are as described above.

In another embodiment, the isomer referred to the in the preceding paragraph is a stereoisomer.

In another embodiment, in formula (I), X is selected from the group consisting of —(C($R^3$)$_2$)$_m$— and —N($R^3$)—.

In another embodiment, in formula (I), X is —(C($R^3$)$_2$)$_m$, wherein m is 1 or 2.

In another embodiment, in formula (I), X is —(C($R^3$)$_2$)$_m$, wherein m is 1.

In another embodiment, in formula (I), $R^3$ is H.

In another embodiment, in formula (I), at least one of T and V is present, and V is other than alkynyl; wherein said T or V is substituted with at least one $R^{10}$ moiety selected from the group consisting of cyano, —C(O)O$R^4$, —C(O)$R^4$, —C(O)N($R^4$)$_2$, —C(O)N($R^4$)C(O)$R^4$, —C(O)N($R^4$)C(O)N$R^4$, —S$R^4$, —S(O)$_2R^4$, —N($R^4$)—C(O)O$R^4$, —OC(O)N($R^4$)$_2$, —N($R^4$)C(O)N($R^4$)$_2$, —N($R^4$)—C(O)—$R^4$, —S(O)$_2$N($R^4$)$_2$, —S(O)$_2$N($R_4$)—C(O)—$R^4$, —N($R^4$)—C(=N$R^4$)—N($R^4$)$_2$, —N($R^4$)—C(=N—CN)—N($R^4$)$_2$, and —C($R^4$)=N—O$R^4$, wherein each $R^4$ independently is selected from the group consisting of H, alkyl, cycloalkyl, heterocyclyl, aryl, and heteroaryl, wherein when each of said $R^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)₂R⁴, V is other than piperidinyl, and when R¹⁰ is cyano, the compound of Formula (I) is other than

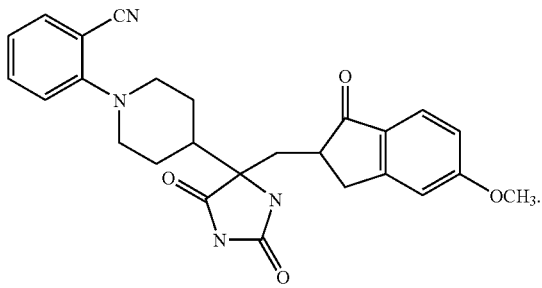

In another embodiment in formula (I), at least one of T and V is present, and V is other than alkynyl; wherein said T or V is substituted with at least one R¹⁰ moiety selected from the group consisting of cyano, —C(O)OR⁴, —C(O)R⁴, —C(O)N(R⁴)₂, —C(O)N(R⁴)C(O)R⁴, —C(O)N(R⁴)C(O)NR⁴, —SR⁴, —S(O)₂R⁴, —N(R⁴)—C(O)OR⁴, —OC(O)N(R⁴)₂, —N(R⁴)C(O)N(R⁴)₂, —N(R⁴)—C(O)—R⁴, —S(O)₂N(R⁴)₂, —S(O)₂N(R₄)—C(O)—R⁴, —N(R⁴)—C(=NR⁴)—N(R⁴)₂, —N(R⁴)—C(=N—CN)—N(R⁴)₂, and —C(R⁴)=N—OR⁴, wherein each R⁴ independently is selected from the group consisting of H, alkyl, cycloalkyl, heterocyclyl, aryl, and heteroaryl, wherein when each of said R⁴ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when R¹⁰ is —S(O)₂R⁴, V is other than piperidinyl, and when R¹⁰ is cyano, the compound of Formula (I) is other than

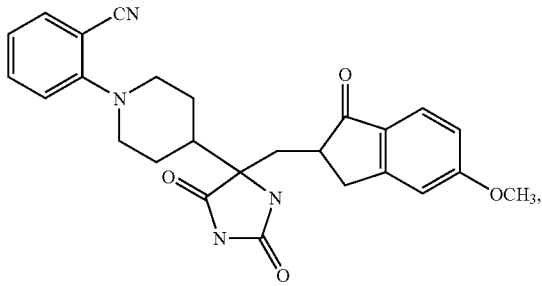

wherein said T or V is substituted with at least one R¹⁰ moiety selected from the group consisting of cyano, —C(O)OR⁴, —C(O)R⁴, —C(O)N(R⁴)₂, and —C(R⁴)=N—OR⁴.

In another embodiment in formula (I), at least one of T and V is present, and V is other than alkynyl; wherein said T or V is substituted with at least one R¹⁰ moiety selected from the group consisting of cyano, —C(O)OR⁴, —C(O)R⁴, —C(O)N(R⁴)₂, —C(O)N(R⁴)C(O)R⁴, —C(O)N(R⁴)C(O)NR⁴, —SR⁴, —S(O)₂R⁴, —N(R⁴)—C(O)OR⁴, —OC(O)N(R⁴)₂, —N(R⁴)C(O)N(R⁴)₂, —N(R⁴)—C(O)—R⁴, —S(O)₂N(R⁴)₂, —S(O)₂N(R₄)—C(O)—R⁴, —N(R⁴)—C(=NR⁴)—N(R⁴)₂, —N(R⁴)—C(=N—CN)—N(R⁴)₂, and —C(R⁴)=N—OR⁴, wherein each R⁴ independently is selected from the group consisting of H, alkyl, cycloalkyl, heterocyclyl, aryl, and heteroaryl, wherein when each of said R⁴ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when R¹⁰ is —S(O)₂R⁴, V is other than piperidinyl, and when R¹⁰ is cyano, the compound of Formula (I) is other than

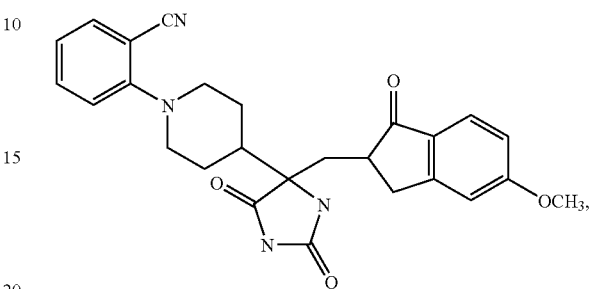

wherein said T or V is substituted with at least one R¹⁰ moiety that is cyano.

In another embodiment, in formula (I), at least one of T and V is present, and V is other than alkynyl; wherein said T or V is substituted with at least one R¹⁰ moiety selected from the group consisting of cyano, —C(O)OR⁴, —C(O)R⁴, —C(O)N(R⁴)₂, —C(O)N(R⁴)C(O)R⁴, —C(O)N(R⁴)C(O)NR⁴, —SR⁴, —S(O)₂R⁴, —N(R⁴)—C(O)OR⁴, —OC(O)N(R⁴)₂, —N(R⁴)C(O)N(R⁴)₂, —N(R⁴)—C(O)—R⁴, —S(O)₂N(R⁴)₂, —S(O)₂N(R₄)—C(O)—R⁴, —N(R⁴)—C(=NR⁴)—N(R⁴)₂, —N(R⁴)—C(=N—CN)—N(R⁴)₂, and —C(R⁴)=N—OR⁴, wherein each R⁴ independently is selected from the group consisting of H, alkyl, cycloalkyl, heterocyclyl, aryl, and heteroaryl, wherein when each of said R⁴ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when R¹⁰ is —S(O)₂R⁴, V is other than piperidinyl, and when R¹⁰ is cyano, the compound of Formula (I) is other than

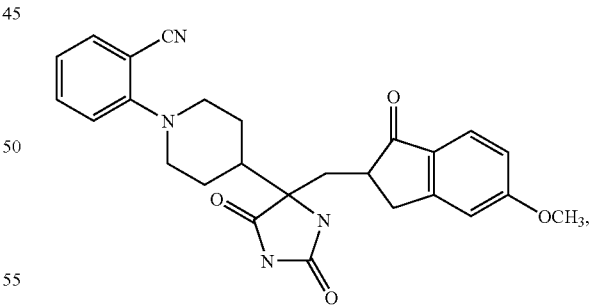

wherein said T or V is substituted with at least one R¹⁰ moiety that is —SR⁴.

In another embodiment, in formula (I), at least one of T and V is present, and V is other than alkynyl; wherein said T or V is substituted with at least one R¹⁰ moiety selected from the group consisting of cyano, —C(O)OR⁴, —C(O)R⁴, —C(O)N(R⁴)₂, —C(O)N(R⁴)C(O)R⁴, —C(O)N(R⁴)C(O)NR⁴, —SR⁴, —S(O)₂R⁴, —N(R⁴)—C(O)OR⁴, —OC(O)N(R⁴)₂, —N(R⁴)C(O)N(R⁴)₂, —N(R⁴)—C(O)—R⁴, —S(O)₂

N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when R$^{10}$ is —S(O)$_2$R$^4$, V is other than piperidinyl, and when R$^{10}$ is cyano, the compound of Formula (I) is other than

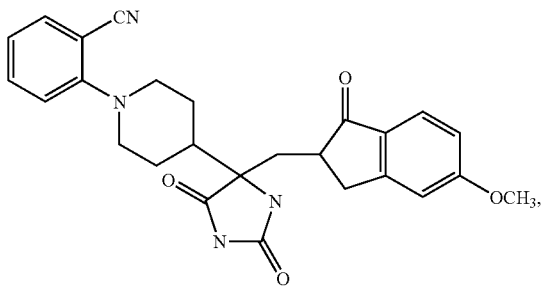

wherein said T or V is substituted with at least one R$^{10}$ moiety that is —S(O)$_2$R$^4$.

In another embodiment, in formula (I), at least one of T and V is present, and V is other than alkynyl; wherein said T or V is substituted with at least one R$^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when R$^{10}$ is —S(O)$_2$R$^4$, V is other than piperidinyl, and when R$^{10}$ is cyano, the compound of Formula (I) is other than

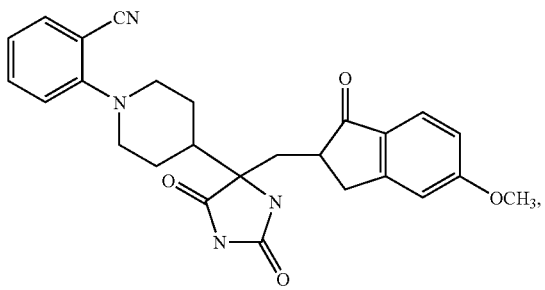

wherein said T or V is substituted with at least one R$^{10}$ moiety that —S(O)$_2$N(R$^4$)$_2$.

In another embodiment, in formula (I), at least one of T and V is present, and V is other than alkynyl; wherein said T or V is substituted with at least one R$^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when R$^{10}$ is —S(O)$_2$R$^4$, V is other than piperidinyl, and when R$^{10}$ is cyano, the compound of Formula (I) is other than

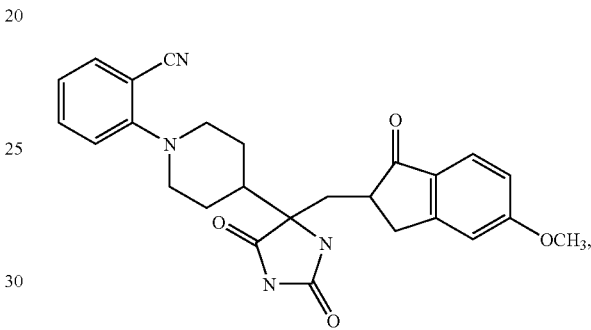

wherein ring A is selected from the group consisting of phenyl, thiophenyl, pyridyl, pyrimidyl, and

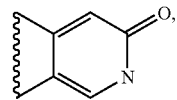

each of which is substituted with —Y—R$^1$ and -Z-R$^2$ as shown.

In another embodiment, in Formula (I), at least one of T and V is present, and V is other than alkynyl; wherein said T or V is substituted with at least one R$^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when R$^{10}$ is —S(O)$_2$R$^4$, V is other than piperidinyl, and when R$^{10}$ is cyano, the compound of Formula (I) is other than

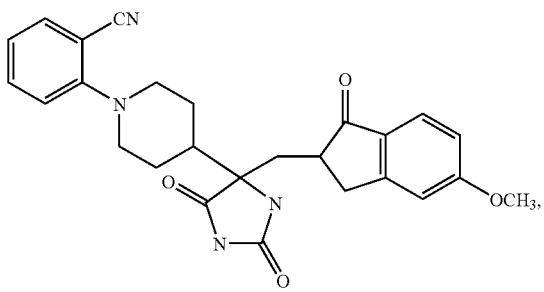

wherein ring A is phenyl.

In another embodiment, in Formula (I), at least one of T and V is present, and V is other than alkynyl; wherein said T or V is substituted with at least one $R^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)$_2$R$^4$, V is other than piperidinyl, and when $R^{10}$ is cyano, the compound of Formula (I) is other than

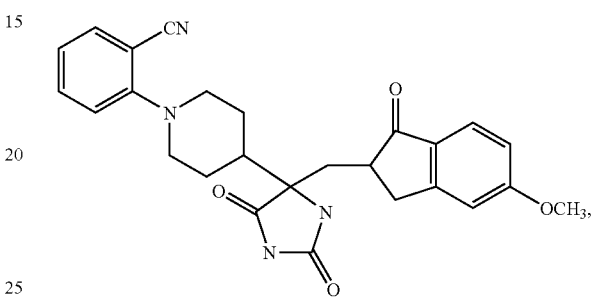

wherein T is selected from the group consisting of alkyl, aryl, heteroaryl, wherein when each of said T aryl and heteroaryl contains two radicals on adjacent carbon atoms, said radicals may optionally be taken together with the carbon atoms to which they are attached to form a five- to eight-membered aryl or heteroaryl ring; wherein each of the aforementioned T aryl, and heteroaryl, optionally with said five- to eight-membered aryl or heteroaryl is independently unsubstituted or substituted with one to four $R^{10}$ moieties which can be the same or different.

In another embodiment, in Formula (I), at least one of T and V is present, and V is other than alkynyl; wherein said T or V is substituted with at least one $R^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)$_2$R$^4$, V is other than piperidinyl, and when $R^{10}$ is cyano, the compound of Formula (I) is other than

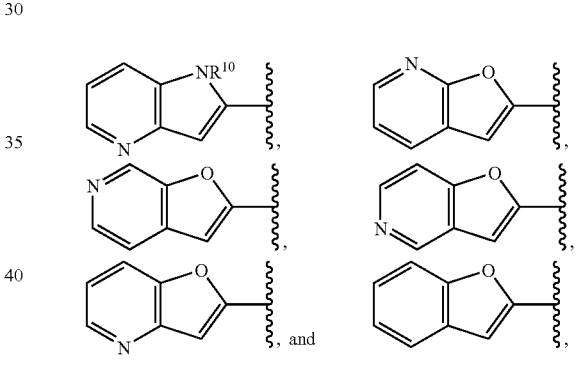

wherein T is selected from the group consisting of —CH$_2$—, phenyl, each of which except —CH$_2$— is optionally substituted with one to four $R^{10}$ moieties such that the number of $R^{10}$ moieties per each T does not exceed four.

In another embodiment, in Formula (I), at least one of T and V is present, and V is other than alkynyl; wherein said T or V is substituted with at least one $R^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)$_2$R$^4$, V is other than piperidinyl, and when $R^{10}$ is cyano, the compound of Formula (I) is other than

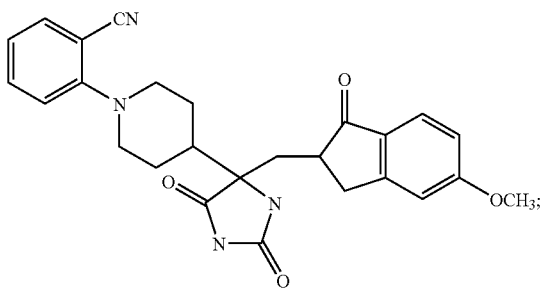

wherein U is absent or present, and if present is selected from the group consisting of —C(O)—, and —C(O)O—.

In another embodiment, in Formula (I), at least one of T and V is present, and V is other than alkynyl; wherein said T or V is substituted with at least one $R^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)$_2$R$^4$, V is other than piperidinyl, and when $R^{10}$ is cyano, the compound of Formula (I) is other than

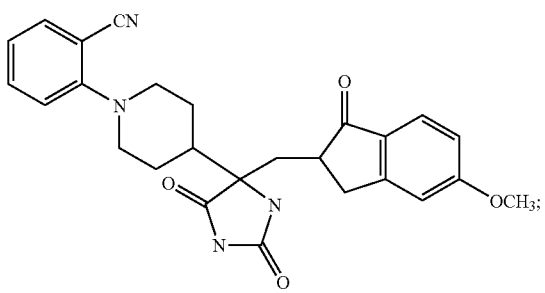

wherein V is absent or present, and if present is selected from the group consisting of aryl, and heteroaryl, wherein when each of said V aryl and heteroaryl contains two radicals on adjacent carbon atoms, said radicals may optionally be taken together with the carbon atoms to which they are attached to form a five- to eight-membered aryl or heteroaryl ring; wherein each of the aforementioned V aryl, and heteroaryl, optionally with said five- to eight-membered aryl or heteroaryl is independently unsubstituted or substituted with one to four $R^{10}$ moieties which can be the same or different.

In another embodiment, in Formula (I), at least one of T and V is present, and V is other than alkynyl; wherein said T or V is substituted with at least one $R^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)$_2$R$^4$, V is other than piperidinyl, and when $R^{10}$ is cyano, the compound of Formula (I) is other than

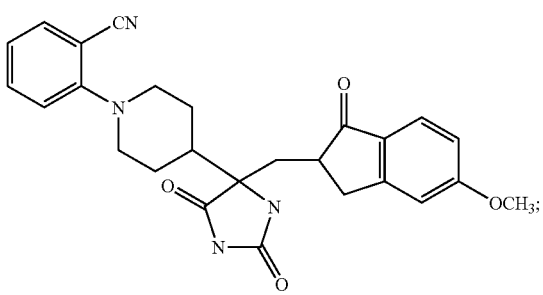

wherein V is selected from the group consisting of phenyl, pyridyl, pyrazinyl, indazolyl,

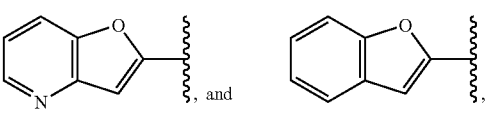

each of which is optionally substituted with one to four $R^{10}$ moieties which can be the same or different.

In another embodiment, in Formula (I), at least one of T and V is present, and V is other than alkynyl; wherein said T or V is substituted with at least one $R^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)$_2$R$^4$, V is other than piperidinyl, and when $R^{10}$ is cyano, the compound of Formula (I) is other than

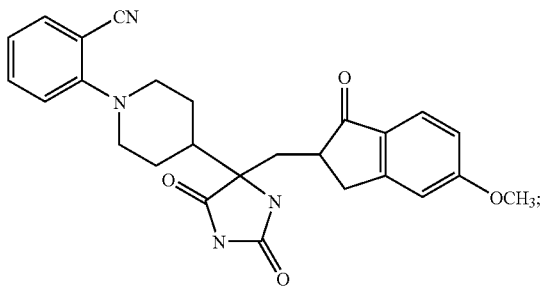

wherein each of Y and Z is independently selected from the group consisting of a covalent bond and —O—.

In another embodiment, in Formula (I), at least one of T and V is present, and V is other than alkynyl; wherein said T or V is substituted with at least one $R^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)$_2$R$^4$, V is other than piperidinyl, and when $R^{10}$ is cyano, the compound of Formula (I) is other than

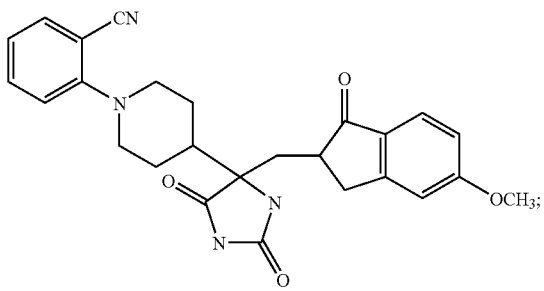

wherein Y is —O— and Z is a covalent bond.

In another embodiment, in Formula (I), at least one of T and V is present, and V is other than alkynyl; wherein said T or V is substituted with at least one $R^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)$_2$R$^4$, V is other than piperidinyl, and when $R^{10}$ is cyano, the compound of Formula (I) is other than

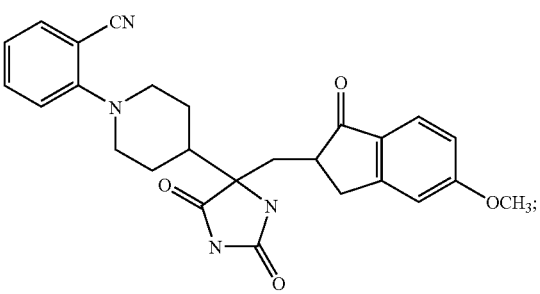

wherein each of $R^1$ and $R^2$ is independently selected form the group consisting of H and alkyl.

In another embodiment, in Formula (I), at least one of T and V is present, and V is other than alkynyl; wherein said T or V is substituted with at least one $R^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when $R^{10}$ is —S(O)$_2$R$^4$, V is other than piperidinyl, and when $R^{10}$ is cyano, the compound of Formula (I) is other than

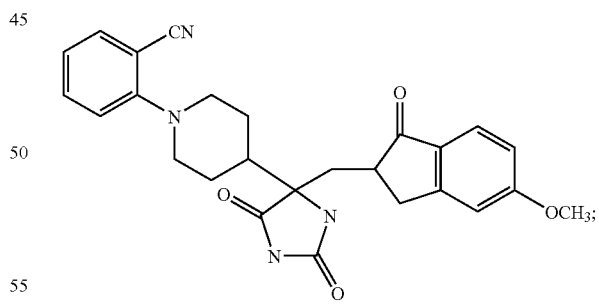

wherein $R^1$ is alkyl and $R^2$ is H.

In another embodiment, in Formula (I), at least one of T and V is present, and V is other than alkynyl; wherein said T or V is substituted with at least one $R^{10}$ moiety selected from the group consisting of cyano, —C(O)OR$^4$, —C(O)R$^4$, —C(O)N(R$^4$)$_2$, —C(O)N(R$^4$)C(O)R$^4$, —C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C (=NR⁴)—N(R⁴)₂, —N(R⁴)—C(=N—CN)—N(R⁴)₂, and —C(R⁴)=N—OR⁴, wherein each R⁴ independently is selected from the group consisting of H, alkyl, cycloalkyl, heterocyclyl, aryl, and heteroaryl, wherein when each of said R⁴ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when R¹⁰ is —S(O)₂R⁴, V is other than piperidinyl, and when R¹⁰ is cyano, the compound of Formula (I) is other than

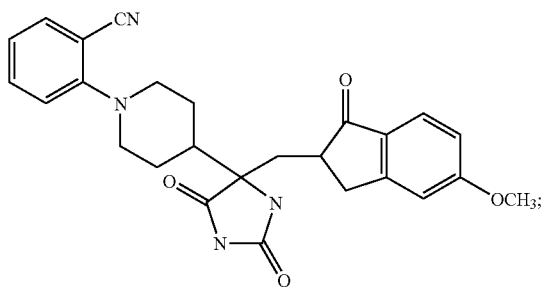

wherein R¹ is methyl.

In another embodiment, in Formula (I), at least one of T and V is present, and V is other than alkynyl; wherein said T or V is substituted with at least one R¹⁰ moiety selected from the group consisting of cyano, —C(O)OR⁴, —C(O)R⁴, —C(O)N(R⁴)₂, —C(O)N(R⁴)C(O)R⁴, —C(O)N(R⁴)C(O)NR⁴, —SR⁴, —S(O)₂R⁴, —N(R⁴)—C(O)OR⁴, —OC(O)N(R⁴)₂, —N(R⁴)C(O)N(R⁴)₂, —N(R⁴)—C(O)—R⁴, —S(O)₂N(R⁴)₂, —S(O)₂N(R₄)—C(O)—R⁴, —N(R⁴)—C(=NR⁴)—N(R⁴)₂, —N(R⁴)—C(=N—CN)—N(R⁴)₂, and —C(R⁴)=N—OR⁴, wherein each R⁴ independently is selected from the group consisting of H, alkyl, cycloalkyl, heterocyclyl, aryl, and heteroaryl, wherein when each of said R⁴ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; with the proviso that when R¹⁰ is —S(O)₂R⁴, V is other than piperidinyl, and when R¹⁰ is cyano, the compound of Formula (I) is other than

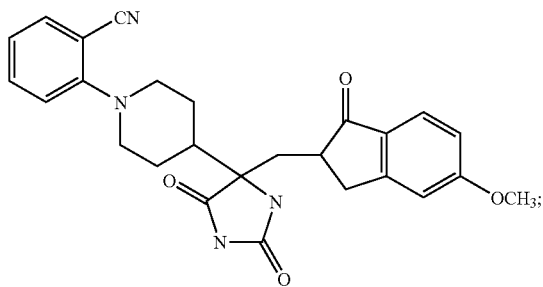

wherein the compound of Formula (I) is selected from the group consisting of:

| Compound ID | Structures |
|---|---|
| 2 | 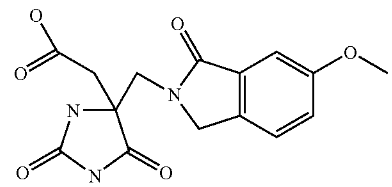 |
| 23 | 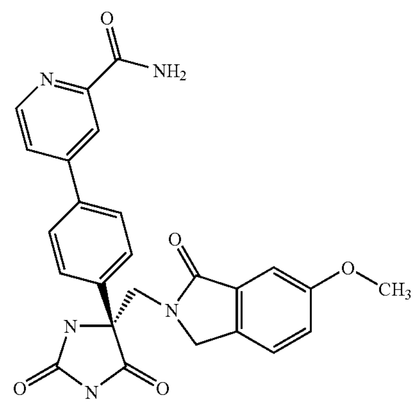 |
| 24 | 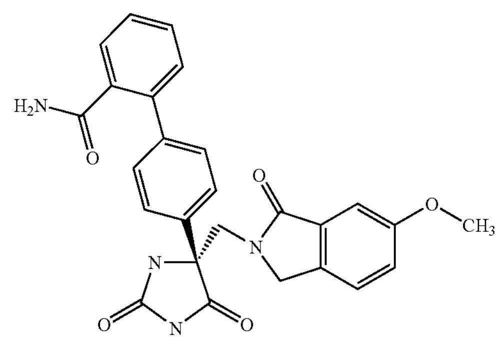 |
| 32 | 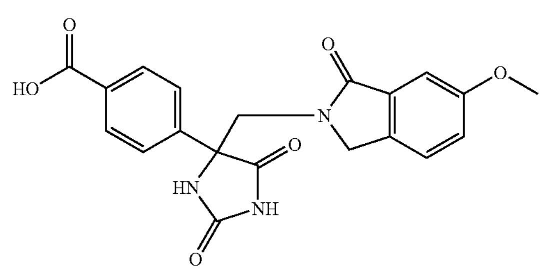 |
| 33 | 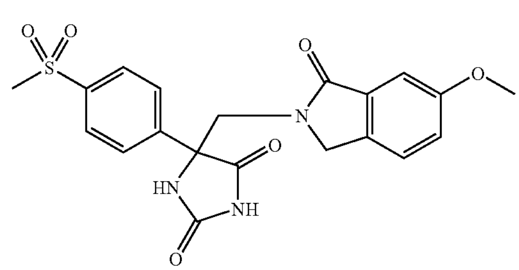 |

-continued
| Compound ID | Structures |
|---|---|
| 38 | 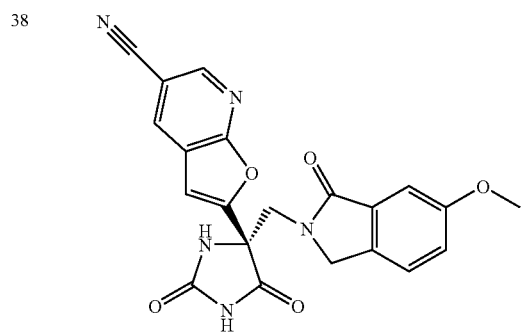 |
| 39 | 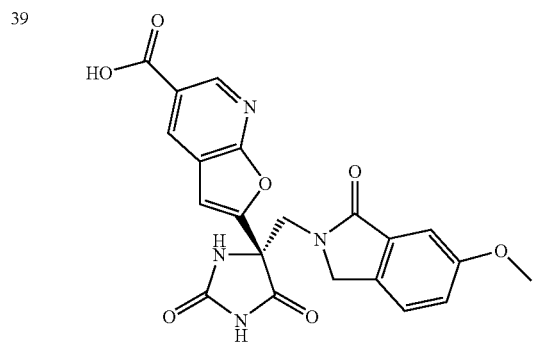 |
| 40 | 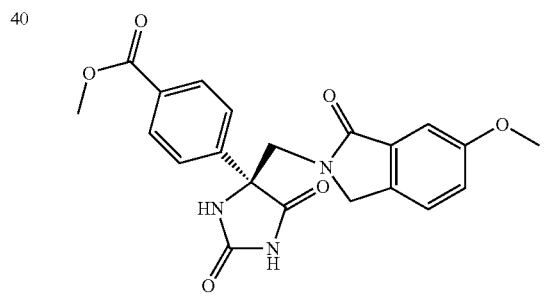 |
| 41 | 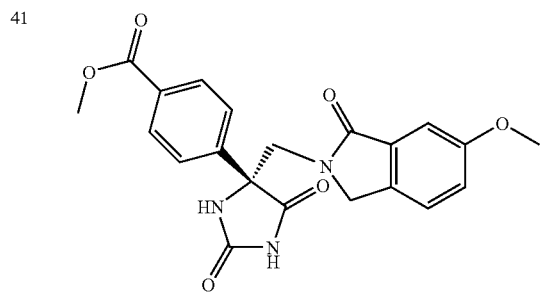 |
-continued
| Compound ID | Structures |
|---|---|
| 42 | 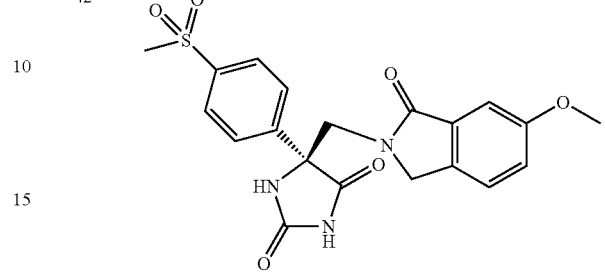 |
| 43 | 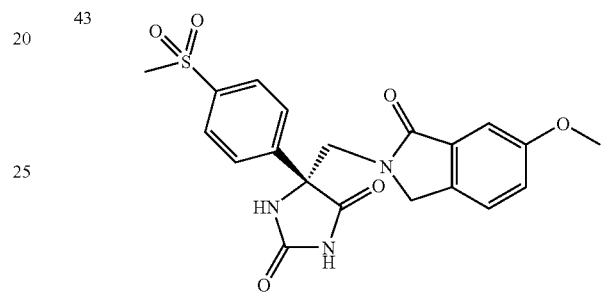 |
| 44 | 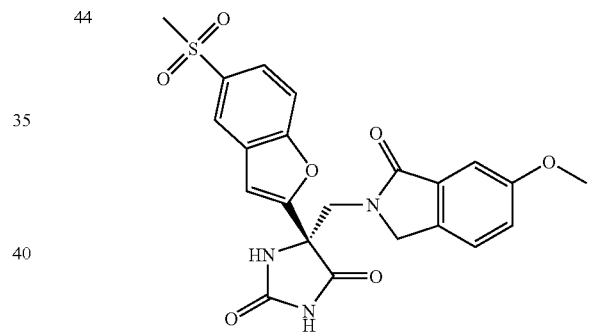 |
| 45 | 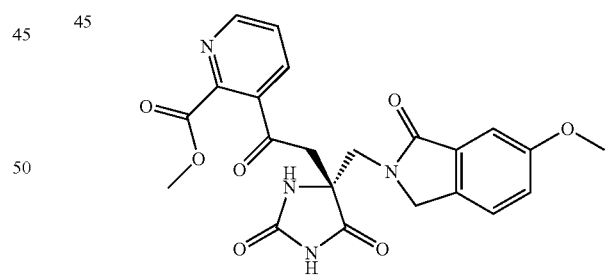 |
| 46 | 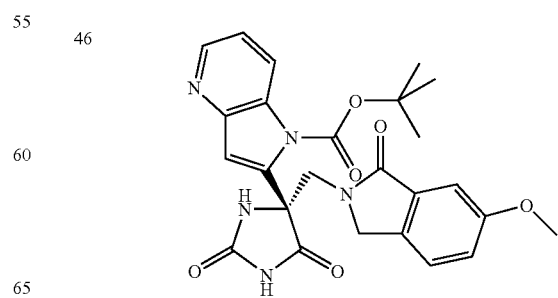 |

-continued
| Compound ID | Structures |
|---|---|
| 47 | 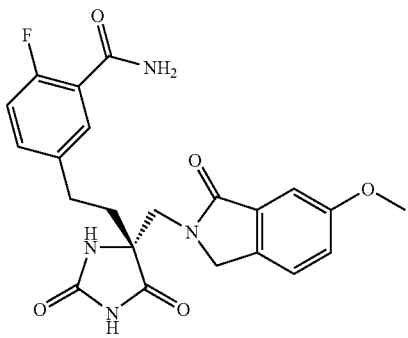 |
| 49 | 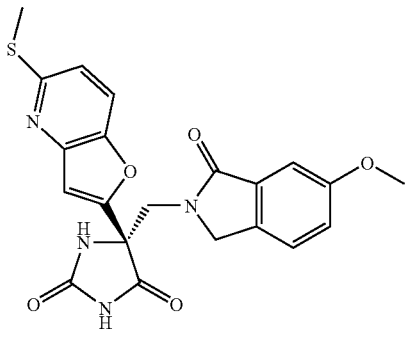 |
| 50 | 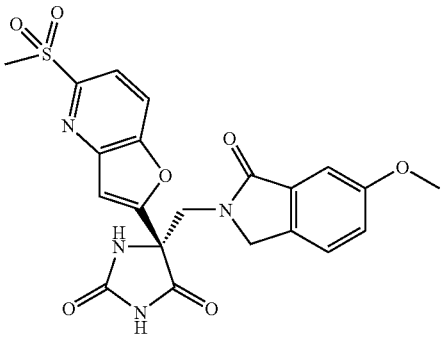 |
| 51 | 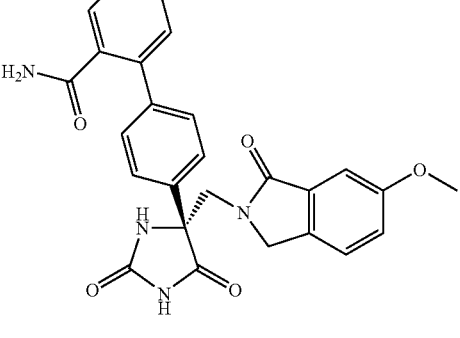 |
-continued
| Compound ID | Structures |
|---|---|
| 52 | 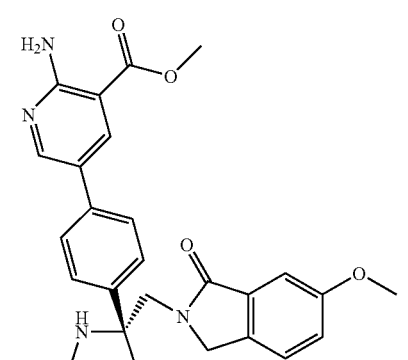 |
| 53 | 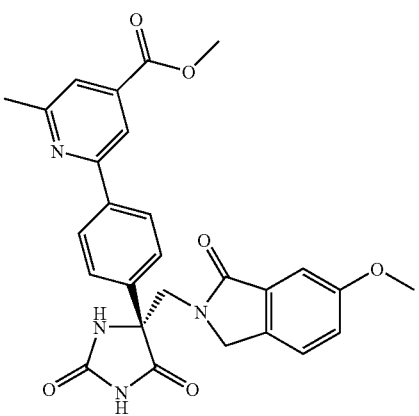 |
| 54 | 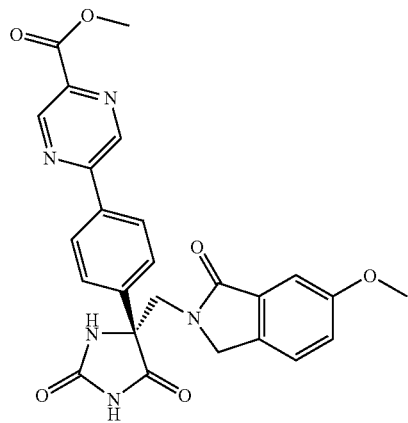 |

-continued
| Compound ID | Structures |
|---|---|
| 55 | 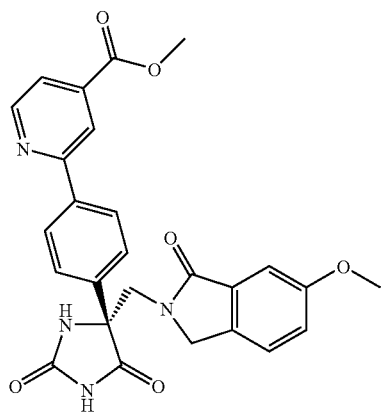 |
| 56 | 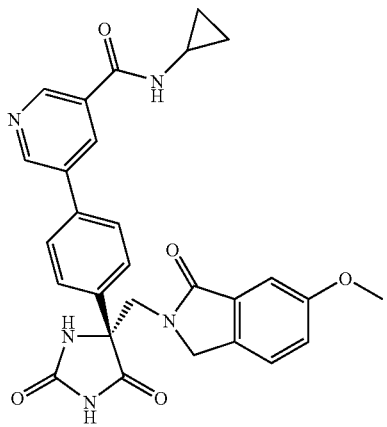 |
| 57 | 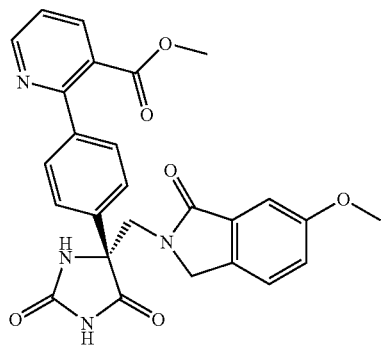 |
-continued
| Compound ID | Structures |
|---|---|
| 58 | 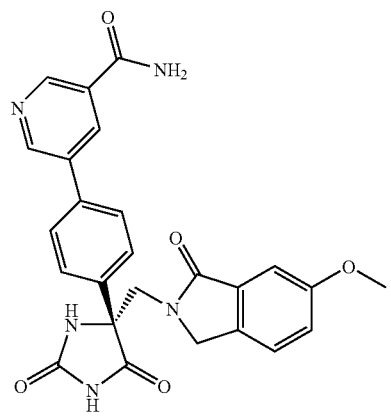 |
| 59 | 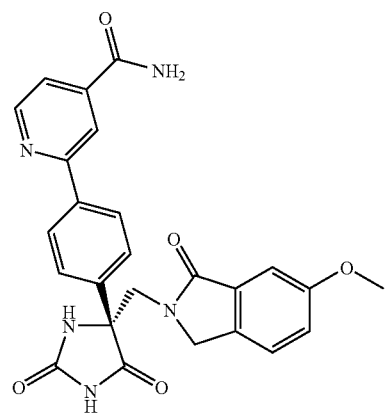 |
| 60 | 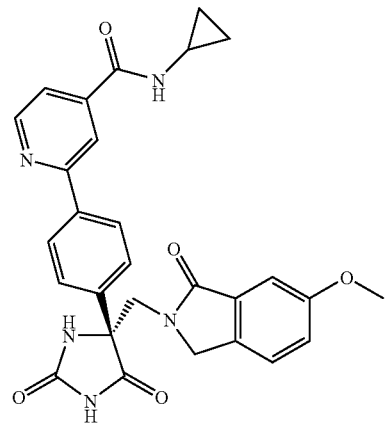 |

-continued
| Compound ID | Structures |
|---|---|
| 61 | 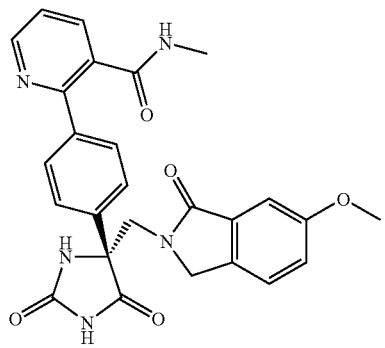 |
| 62 | 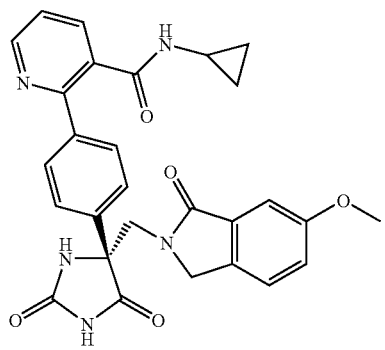 |
| 63 | 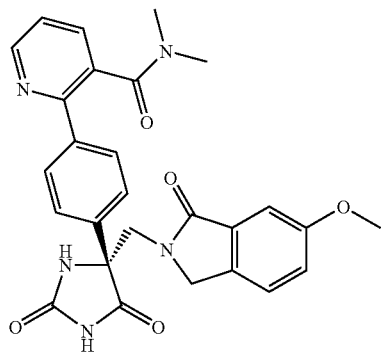 |
| 64 | 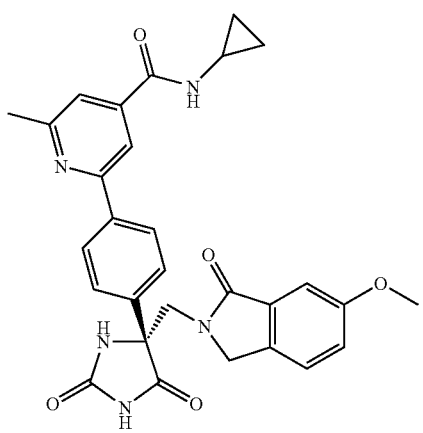 |
-continued
| Compound ID | Structures |
|---|---|
| 65 | 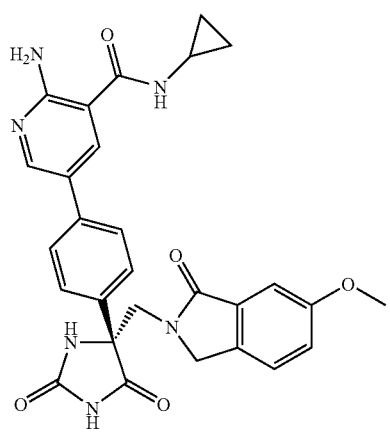 |
| 66 | 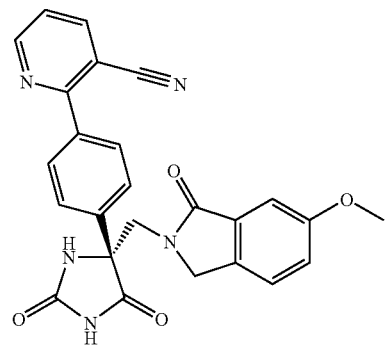 |
| 67 | 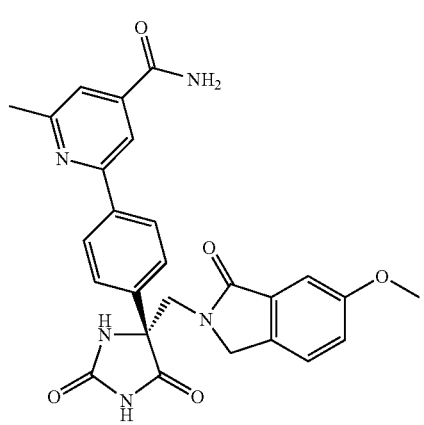 |

-continued
| Compound ID | Structures |
|---|---|
| 68 | 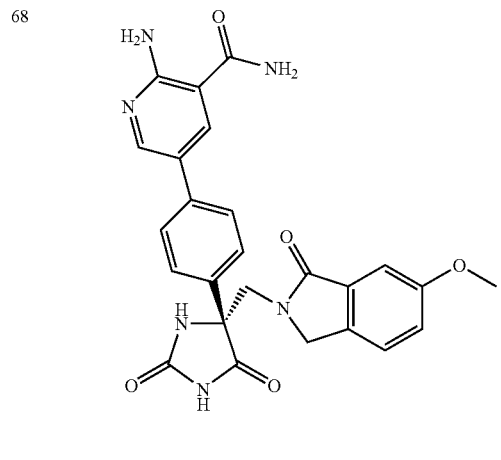 |
| 69 | 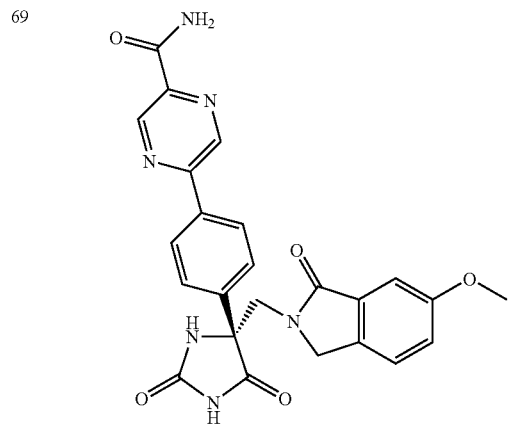 |
| 70 | 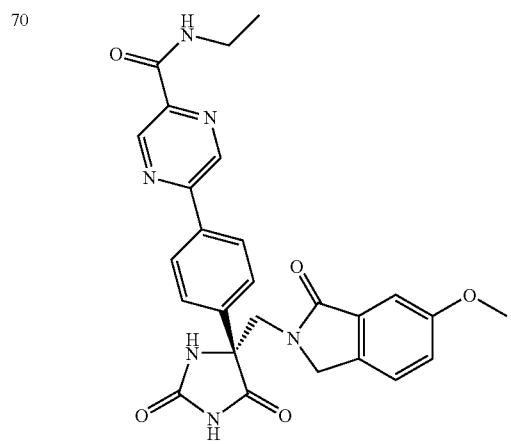 |
-continued
| Compound ID | Structures |
|---|---|
| 71 | 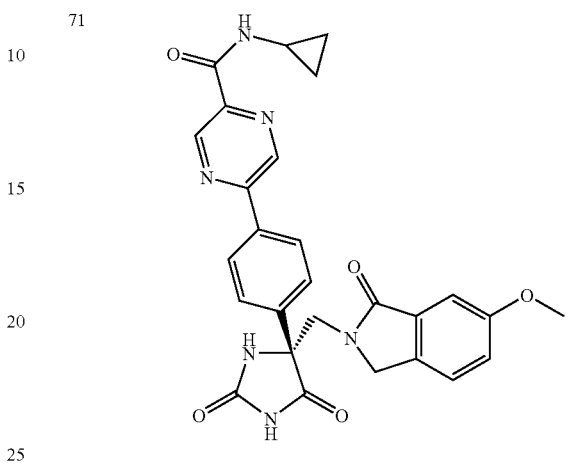 |
| 72 | 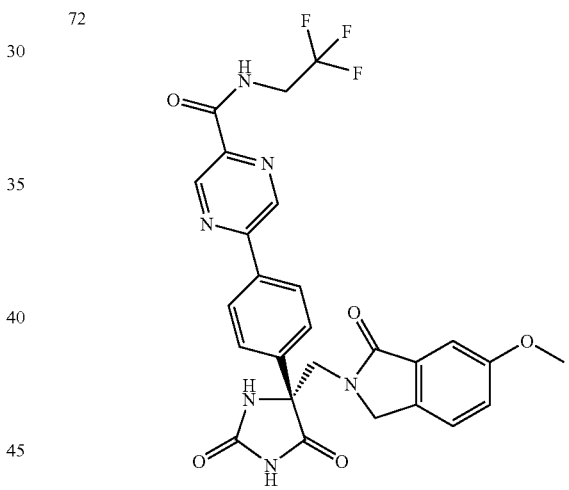 |
| 73 | 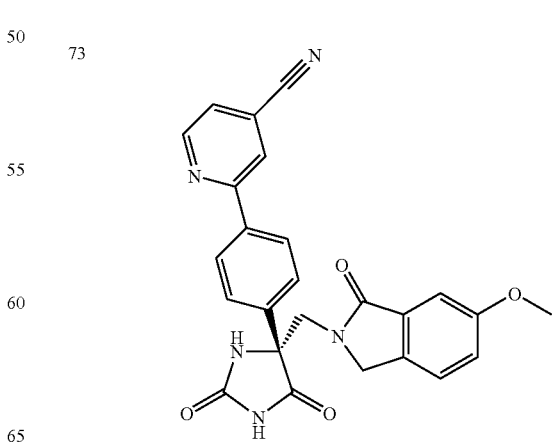 |

-continued
| Compound ID | Structures |
|---|---|
| 74 | 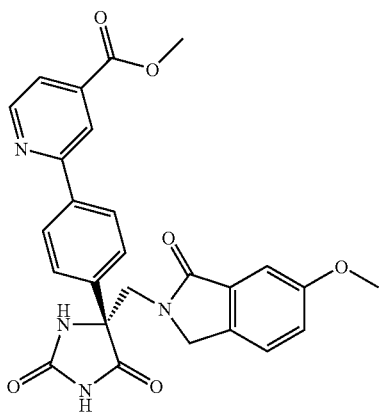 |
| 75 | 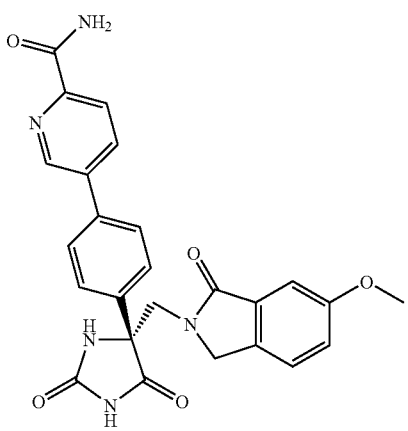 |
| 76 | 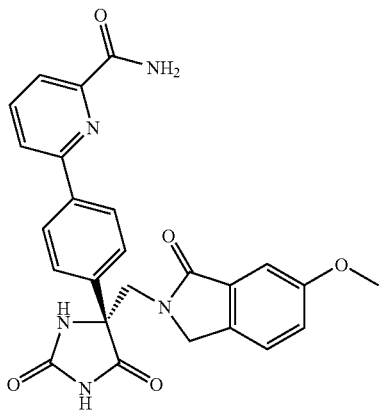 |
-continued
| Compound ID | Structures |
|---|---|
| 77 | 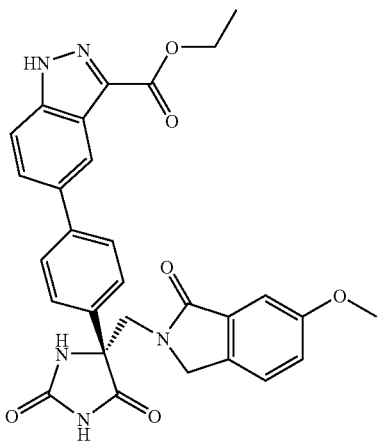 |
| 78 | 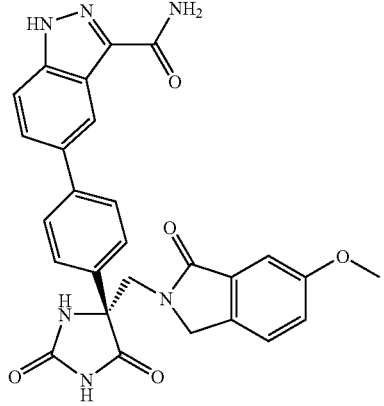 |
| 79 | 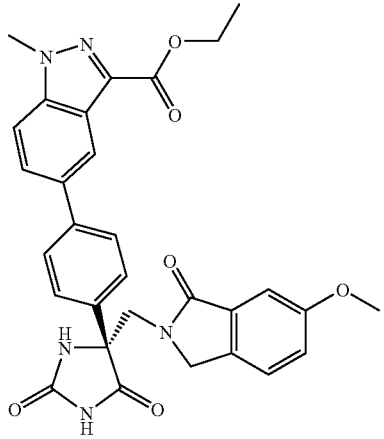 |

| Compound ID | Structures |
|---|---|
| 80 | 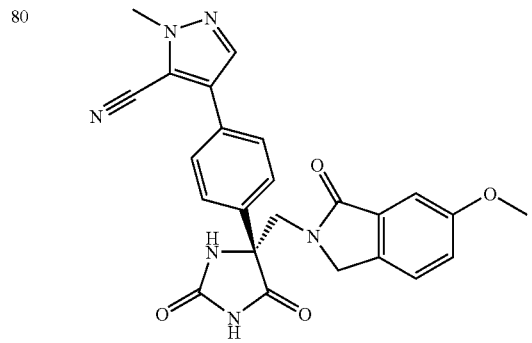 |
| 81 | 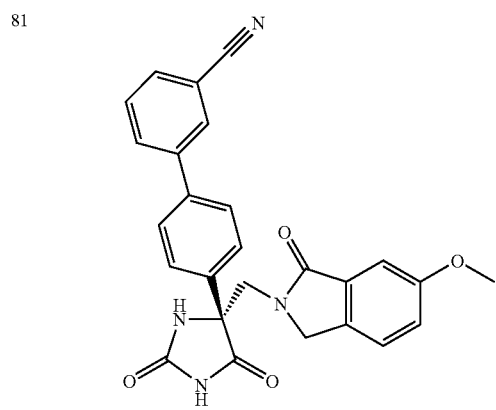 |
| 82 | 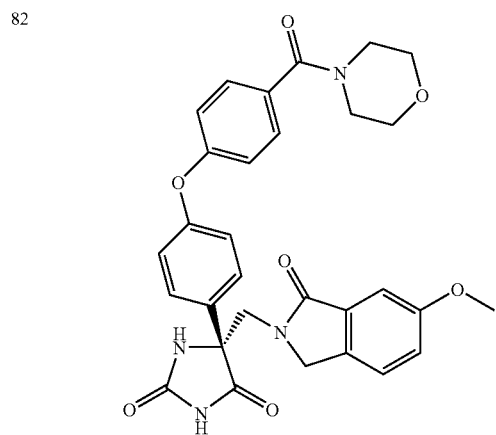 |
| Compound ID | Structures |
|---|---|
| 83 | 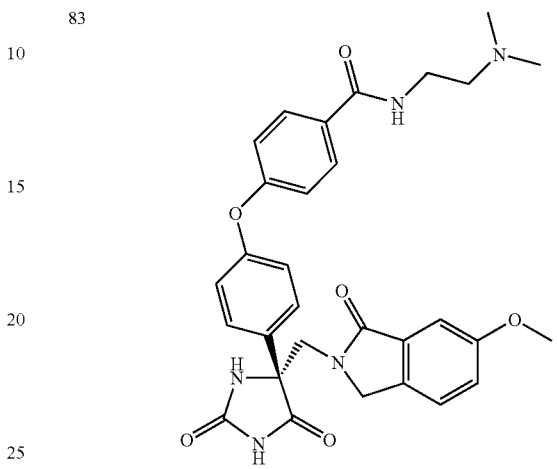 |
| 84 | 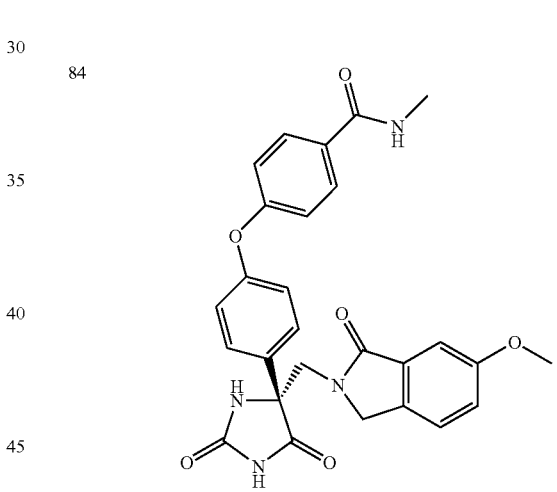 |
| 85 | 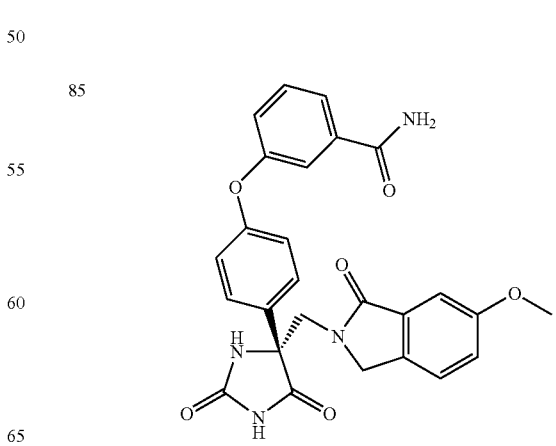 |

| Compound ID | Structures |
|---|---|
| 86 | |
| 87 | |
| 88 | |
| 89 | |
| 90 | |
| 97 | |
| 105 | | or a pharmaceutically acceptable salt, solvate or ester thereof.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-;

wherein ring A is selected from the group consisting of phenyl, thiophenyl, pyridyl, pyrimidyl, and

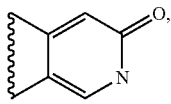

each of which is substituted with —Y—R$^1$ and -Z—R$^2$ as shown.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-; wherein ring A is phenyl.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-; and wherein T is absent or present, and when present, is selected from the group consisting of alkyl, and aryl, each of which is unsubstituted or substituted with one to four R$^{10}$ moieties which can be the same or different.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-; and wherein T is absent or present, and when present is selected from the group consisting of —CH$_2$—, and phenyl.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-; and wherein V is selected from the group consisting of alkyl, heterocyclyl, and cycloalkyl, wherein when each of said V heterocyclyl or cycloalkyl contains two radicals on adjacent carbon atoms, said radicals may optionally be taken together with the carbon atoms to which they are attached to form a five- to eight-membered cycloalkyl, heterocyclyl, aryl or heteroaryl ring; wherein each of aforementioned V alkyl, heterocyclyl, and cycloalkyl, optionally with said five- to eight-membered cycloalkyl, heterocyclyl, aryl or heteroaryl ring is independently unsubstituted or substituted with one to four R$^{10}$ moieties which can be the same or different.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=O—N—O-alkyl)-alkyl-; and wherein V is selected from the group consisting of methyl, ethyl, isopropyl, morpholinyl, cyclohexyl, piperidinyl optionally substituted with cyano or phenyl, —CH$_2$— substituted with tetrahydrofuranyl and

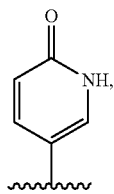

—CH(CH$_3$)— substituted with phenyl, piperazinyl substituted with methyl, pyrrolidinyl substituted with —CH$_2$-phenyl,

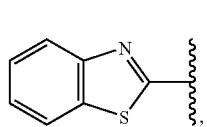 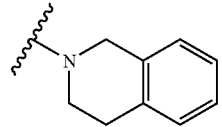

substituted with cyclopropyl, and

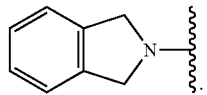

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-; and wherein each of Y and Z is independently selected from the group consisting of a covalent bond and —O—.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-; and wherein Y is —O— and Z is a covalent bond.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-; and wherein each of R$^1$ and R$^2$ is independently selected form the group consisting of H and alkyl.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-; and wherein R$^1$ is alkyl and R$^2$ is H.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-; and wherein R$^1$ is methyl.

In another embodiment, in Formula (I), U and V are present; and U is selected from the group consisting of —O—C(O)NH—, —OC(O)N(alkyl)-, —C(O)—, —C(O)O—, —C(O)NH—, —C(O)N(alkyl)-, —C(=N—OH)-alkyl-, and —C(=N—O-alkyl)-alkyl-; and wherein the compound of Formula (I) is selected from the group consisting of:

| Compound ID | Structures |
|---|---|
| 1 | 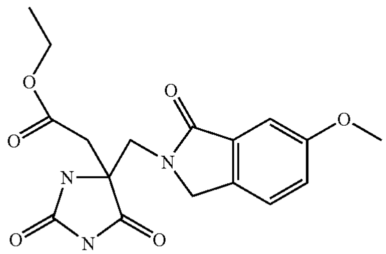 |
| 2 | 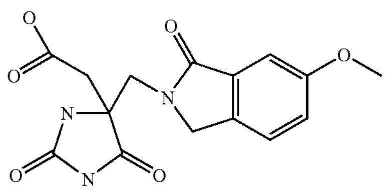 |
| 3 | 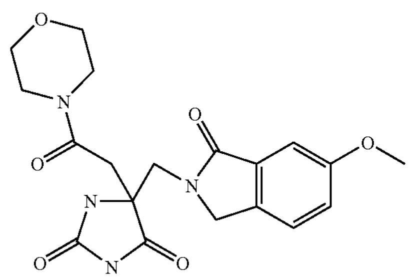 |
| 4 | 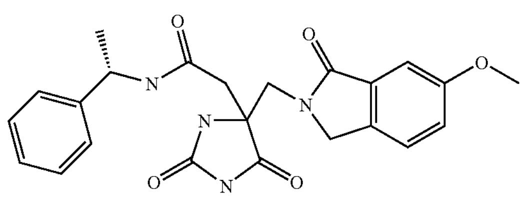 |
| 5 | 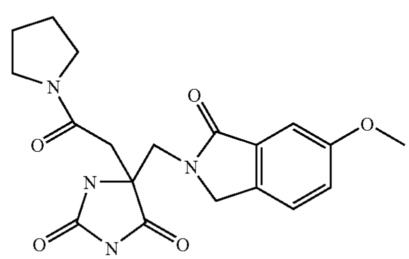 |
| 6 | 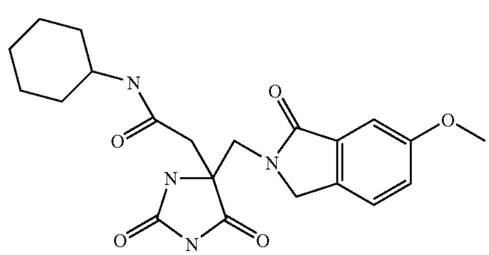 |

-continued

| Compound ID | Structures |
|---|---|
| 7 | 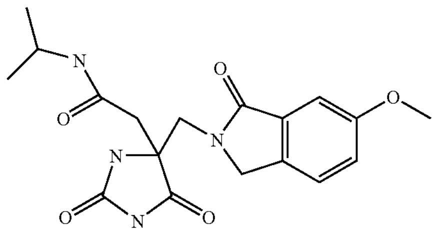 |
| 8 | 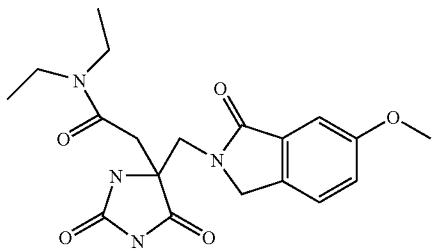 |
| 9 | 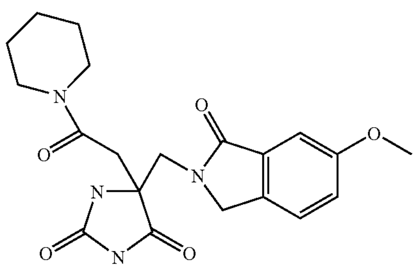 |
| 10 | 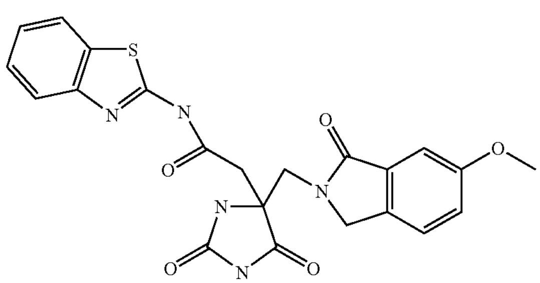 |
| 11 | 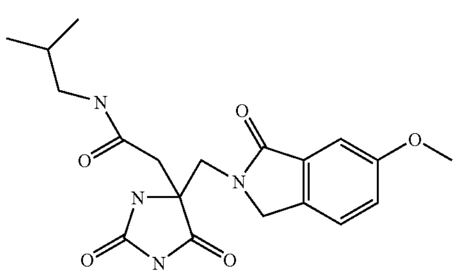 |

-continued
| Compound ID | Structures |
|---|---|
| 12 | 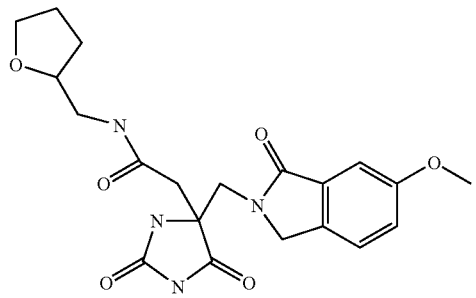 |
| 13 | 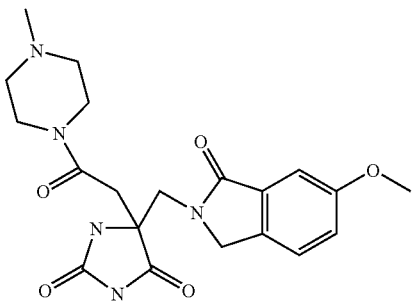 |
| 14 | 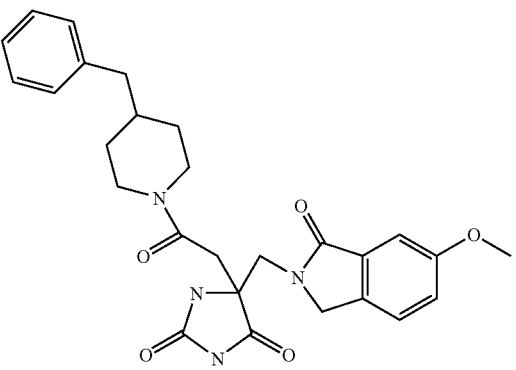 |
| 15 | 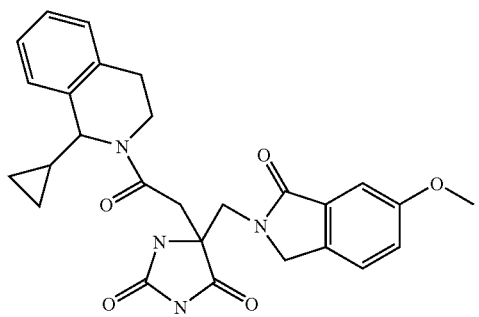 |

-continued

| Compound ID | Structures |
|---|---|
| 16 | |
| 17 | |
| 30 | |
| 31 | | or a pharmaceutically acceptable salt, solvate or ester thereof.

In another embodiment, in Formula (I), at least one T and V is present, and each of —Y—$R^1$ and -Z-$R^2$ is independently selected from the group consisting of cyano, —(C($R^4$)$_2$)$_n$—C(O)OH, —(C($R^4$)$_2$)$_n$—C(O)O-alkyl, —(C($R^4$)$_2$)$_n$—C(O)NH$_2$, —(C($R^4$)$_2$)$_n$—C(O)NH(alkyl), and —(C($R^4$)$_2$)$_n$—C(O)N(alkyl)$_2$, wherein each $R^4$ independently is H or alkyl; and n is 1-3.

In another embodiment, in Formula (I), at least one T and V is present, and each of —Y—$R^1$ and -Z-$R^2$ is independently selected from the group consisting of cyano, —(C($R^4$)$_2$)$_n$—C(O)OH, —(C($R^4$)$_2$)$_n$—C(O)O-alkyl, —(C($R^4$)$_2$)$_n$—C(O)NH$_2$, —(C($R^4$)$_2$)$_n$—C(O)NH(alkyl), and —(C($R^4$)$_2$)$_n$—C(O)N(alkyl)$_2$, wherein each $R^4$ independently is H or alkyl; and n is 1-3; wherein ring A is selected from the group consisting of phenyl, thiophenyl, pyridyl, pyrimidyl, and

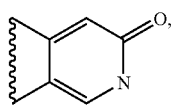

each of which is substituted with —Y—R$^1$ and -Z-R$^2$ as shown.

In another embodiment, in Formula (I), at least one T and V is present, and each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein said ring A is phenyl.

In another embodiment, in Formula (I), at least one T and V is present, and each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein T or V is aryl which is unsubstituted or substituted with one to four R$^{10}$ moieties.

In another embodiment, in Formula (I), at least one T and V is present, and each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein said T or V is phenyl which is unsubstituted or substituted with one to four R$^{10}$ moieties.

In another embodiment, in Formula (I), at least one T and V is present, and each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein R$^{10}$ is fluoro.

In another embodiment, in Formula (I), at least one T and V is present, and each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein only one of T and V is present.

In another embodiment, in Formula (I), at least one T and V is present; each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein U is absent.

In another embodiment, in Formula (I), at least one T and V is present; each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3, wherein n is 1.

In another embodiment, in Formula (I), at least one T and V is present; each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein each of Y and Z is independently selected from the group consisting of a covalent bond and —CH$_2$—, and each of R$^1$ and R$^2$ is independently selected from the group consisting of cyano, —C(O)OH or —C(O)NH$_2$.

In another embodiment, in Formula (I), at least one T and V is present, each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein Y is a covalent bond, and R$^1$ is H.

In another embodiment, in Formula (I), at least one T and V is present; each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein Z is a covalent bond, and R$^2$ is cyano.

In another embodiment, in Formula (I), at least one T and V is present; each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein Z is —CH$_2$—, and R$^2$ is —C(O)OH or —C(O)NH$_2$.

In another embodiment, in Formula (I), at least one T and V is present; each of —Y—R$^1$ and -Z-R$^2$ is independently selected from the group consisting of cyano, —(C(R$^4$)$_2$)$_n$—C(O)OH, —(C(R$^4$)$_2$)$_n$—C(O)O-alkyl, —(C(R$^4$)$_2$)$_n$—C(O)NH$_2$, —(C(R$^4$)$_2$)$_n$—C(O)NH(alkyl), and —(C(R$^4$)$_2$)$_n$—C(O)N(alkyl)$_2$, wherein each R$^4$ independently is H or alkyl; and n is 1-3; wherein the compound of Formula (I) is selected from the group consisting of:

| Compound ID | Structures |
|---|---|
| 35 | [structure of compound 35] |
| 36 | [structure of compound 36] |
| 37 | [structure of compound 37] | or a pharmaceutically acceptable salt or solvate thereof.

In another embodiment, in Formula (I), T is aryl or heteroaryl, each of which is optionally substituted with one to four independently selected $R^{10}$ moieties, and V is alkynyl which is optionally substituted with one or two independently selected $R^{10}$ moieties.

In another embodiment, in Formula (I), T is aryl or heteroaryl, each of which is optionally substituted with one to four independently selected $R^{10}$ moieties, and V is alkynyl which is optionally substituted with one or two independently selected $R^{10}$ moieties; wherein ring A is selected from the group consisting of phenyl, thiophenyl, pyridyl, pyrimidyl, and

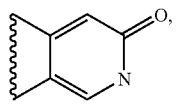

each of which is substituted with —Y—$R^1$ and -Z-$R^2$ as shown.

In another embodiment, in Formula (I), T is aryl or heteroaryl, each of which is optionally substituted with one to four independently selected $R^{10}$ moieties, and V is alkynyl which is optionally substituted with one or two independently selected $R^{10}$ moieties; wherein said ring A is phenyl.

In another embodiment, in Formula (I), T is aryl or heteroaryl, each of which is optionally substituted with one to four independently selected $R^{10}$ moieties, and V is alkynyl which is optionally substituted with one or two independently selected $R^{10}$ moieties; wherein T is aryl, U is —O— or absent, and V is alkynyl which is unsubstituted or substituted with one or two $R^{10}$ moieties selected from the group consisting of —$OR^4$—$N(R^4)_2$, and heteroaryl; wherein when said heteroaryl contains two radicals on adjacent carbon atoms, said radicals may optionally be taken together with the carbon atoms to which they are attached to form a five- to eight-membered aryl, heterocyclyl, heteroaryl or cycloalkyl ring; wherein each $R^4$ independently is H or alkyl, and said $R^{10}$ heteroaryl is optionally independently substituted with one to four $R^{30}$ moieties which can be the same or different.

In another embodiment, in Formula (I), T is aryl or heteroaryl, each of which is optionally substituted with one to four independently selected $R^{10}$ moieties, and V is alkynyl which is optionally substituted with one or two independently selected $R^{10}$ moieties; wherein T is phenyl.

In another embodiment, in Formula (I), T is aryl or heteroaryl, each of which is optionally substituted with one to four independently selected $R^{10}$ moieties, and V is alkynyl which is optionally substituted with one or two independently selected $R^{10}$ moieties; wherein said V alkynyl is selected from the group consisting of —$CH_2$—C≡C—$CH_3$, and $R^{10}$ substituted —C≡C—, and —$CH_2$—C≡C—$CH_2$—.

In another embodiment, in Formula (I), T is aryl or heteroaryl, each of which is optionally substituted with one to four independently selected $R^{10}$ moieties, and V is alkynyl which is optionally substituted with one or two independently selected $R^{10}$ moieties; wherein said $R^{10}$ substituents are selected from the group consisting of —N(alkyl)$_2$, —OH, —$OCH_3$, and pyridyl.

In another embodiment, in Formula (I), T is aryl or heteroaryl, each of which is optionally substituted with one to four independently selected $R^{10}$ moieties, and V is alkynyl which is optionally substituted with one or two independently selected $R^{10}$ moieties; wherein the compound of Formula (I) is selected from the group consisting of:

| Compound ID | Structures |
|---|---|
| 18 | ![structure 18] |
| 19 | ![structure 19] |
| 20 | ![structure 20] |

-continued

| Compound ID | Structures |
|---|---|
| 21 | 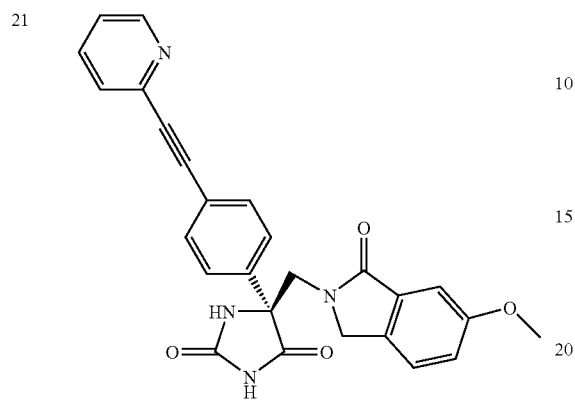 |
| 22 | 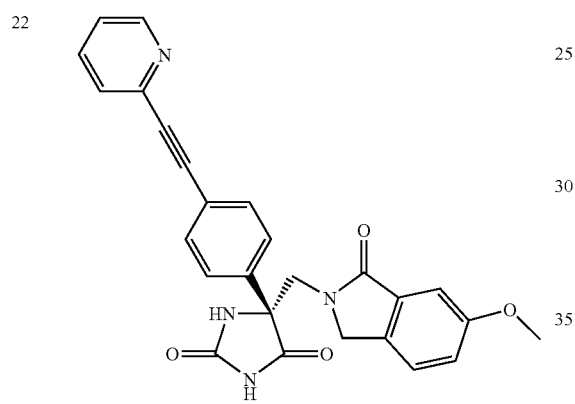 |
| 91 | 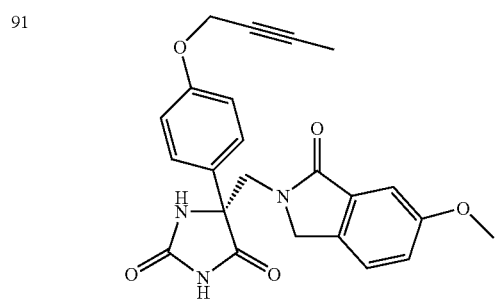 |
| 92 | 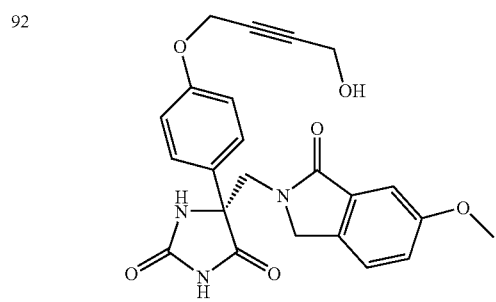 |

-continued

| Compound ID | Structures |
|---|---|
| 94 | 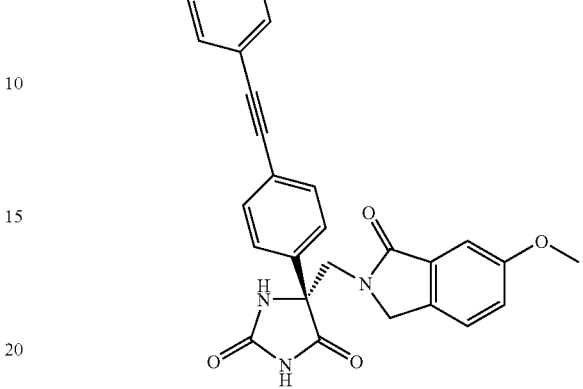 |
| 95 | 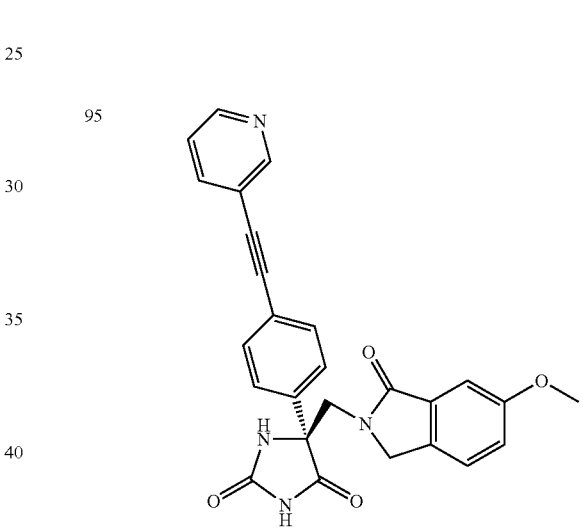 | or a pharmaceutically acceptable salt, solvate, or ester thereof.

In another embodiment, in Formula (I), at least one of T and V is present, ring A is heteroaryl, and V is other than alkynyl.

In another embodiment, in Formula (I), at least one of T and V is present, ring A is heteroaryl, and V is other than alkynyl; wherein ring A is selected from the group consisting of thiophenyl, pyridyl, pyrimidyl, and

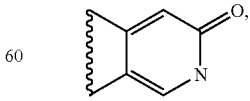

each of which is substituted with —Y—$R^1$ and -Z-$R^2$ as shown.

In another embodiment, in Formula (I), at least one of T and V is present, ring A is heteroaryl, and V is other than alkynyl; wherein T is selected from the group consisting of alkyl, and halo-substituted aryl.

In another embodiment, in Formula (I), at least one of T and V is present, ring A is heteroaryl, and V is other than alkynyl; wherein U and V are absent.

In another embodiment, in Formula (I), at least one of T and V is present, ring A is heteroaryl, and V is other than alkynyl; wherein Y is selected from the group consisting of a covalent bond and —O—, and Z is a covalent bond.

In another embodiment, in Formula (I), at least one of T and V is present, ring A is heteroaryl, and V is other than alkynyl; wherein $R^1$ is selected from the group consisting of H and —CH$_3$; and $R^2$ is H.

In another embodiment, in Formula (I), at least one of T and V is present, ring A is heteroaryl, and V is other than alkynyl; wherein Y is a covalent bond $R^1$ is H.

In another embodiment, in Formula (I), at least one of T and V is present, ring A is heteroaryl, and V is other than alkynyl; wherein Y is —O— and $R^1$ is —CH$_3$.

In another embodiment, in Formula (I), at least one of T and V is present, ring A is heteroaryl, and V is other than alkynyl; wherein Z is a covalent bond and $R^2$ is H.

In another embodiment, in Formula (I), at least one of T and V is present, ring A is heteroaryl, and V is other than alkynyl; wherein the compound of Formula (I) is selected from the group consisting of:

| Compound ID | Structures |
|---|---|
| 25 | |
| 26 | 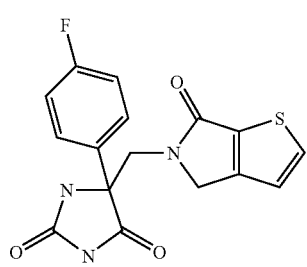 |
| 27 | |
| 28 | |
| 29 | | or a pharmaceutically acceptable salt or solvate thereof.

In another embodiment, the compound of Formula (I) is selected from the group consisting of compounds listed in the table below (Table 1), or a pharmaceutically acceptable salt, solvate, ester or isomer thereof. This table also lists the mass spectroscopy data and the Ki rating for each compound. Those compounds having a Ki value of less than 10 nM (<10 nM) are designated with letter "A"; those with a Ki value of from 10 to less than 100 nM (10-<100 nM) are designated with letter "B"; those with a Ki value of from 100 to 1000 nM are designated with letter "C"; and those with a Ki value of more than 1000 nM (>1000 nM) are designated with letter "D". The synthesis and characterization of these compounds is described hereinbelow in the "EXAMPLES" section of the present application.

TABLE 1

| Compound ID | Structures | Exact Mass | Mass Obsvd | Ki Rating |
|---|---|---|---|---|
| 1 | 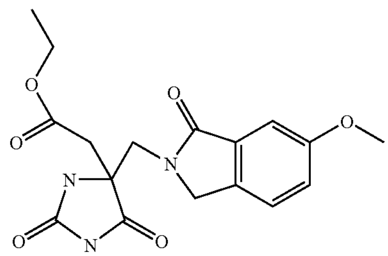 | 361.13 | 362.2[M + H]+ | B |
| 2 | 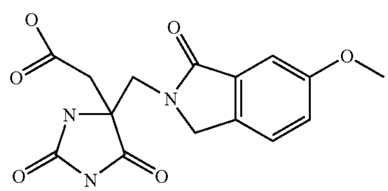 | 333.10 | 334.2[M + H]+ | C |
| 3 | 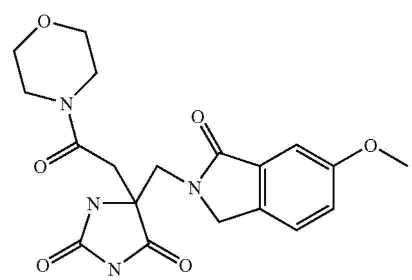 | 402.15 | 403.2[M + H]+ | B |
| 4 | 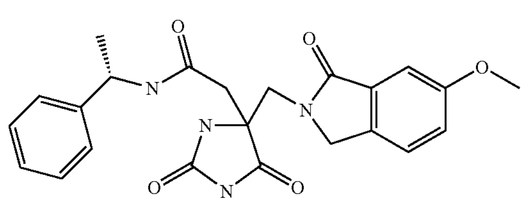 | 436.2 | 437.2[M + H]+ | B |
| 5 | 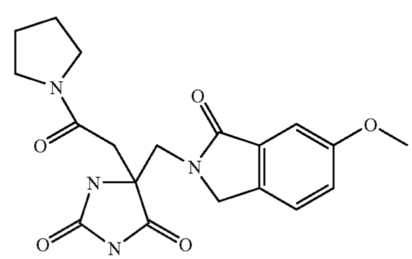 | 386.2 | 387.2[M + H]+ | A |
| 6 | 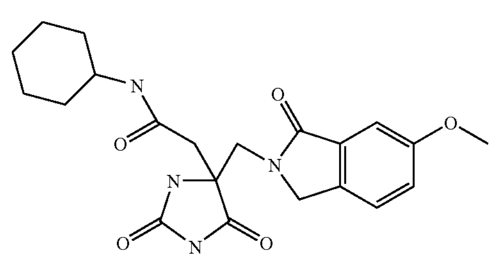 | 414.19 | 415.2[M + H]+ | B |

TABLE 1-continued

| Compound ID | Structures | Exact Mass | Mass Obsvd | Ki Rating |
|---|---|---|---|---|
| 7 | 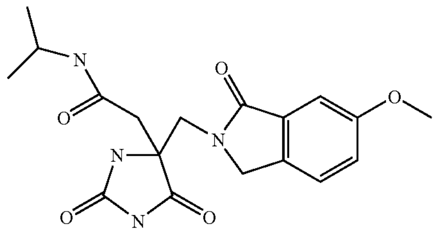 | 374.16 | 375.2[M + H]+ | B |
| 8 | 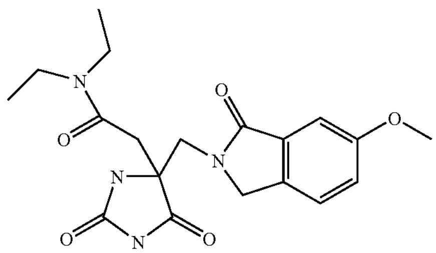 | 388.17 | 389.2[M + H]+ | B |
| 9 | 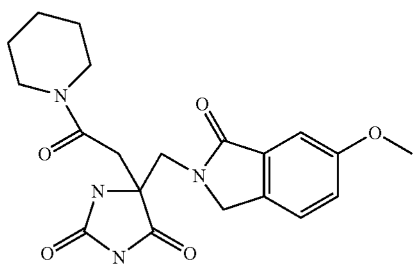 | 400.17 | 401.2[M + H]+ | A |
| 10 | 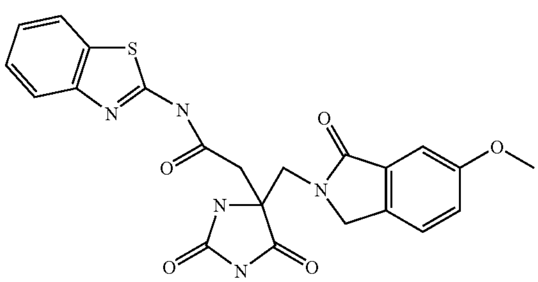 | 465.11 | 466.3[M + H]+ | A |
| 11 | 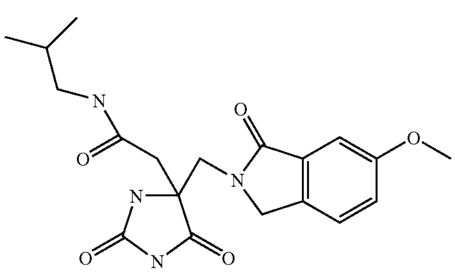 | 388.17 | 389.2[M + H]+ | B |

TABLE 1-continued

| Compound ID | Structures | Exact Mass | Mass Obsvd | Ki Rating |
|---|---|---|---|---|
| 12 | 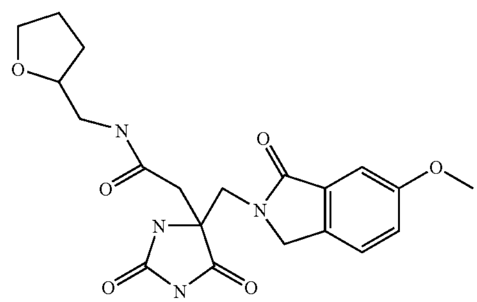 | 416.17 | 417.2[M + H]+ | B |
| 13 | 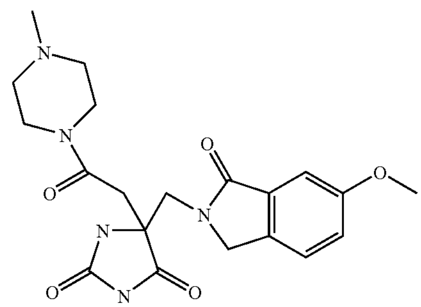 | 415.19 | 416.2[M + H]+ | B |
| 14 | 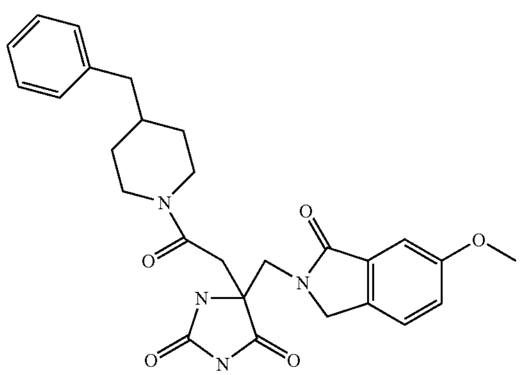 | 490.22 | 491.3[M + H]+ | A |
| 15 | 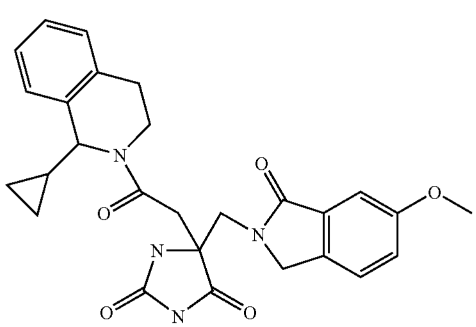 | 488.21 | 489.3[M + H]+ | A |

TABLE 1-continued
| Compound ID | Structures | Exact Mass | Mass Obsvd | Ki Rating |
|---|---|---|---|---|
| 16 | 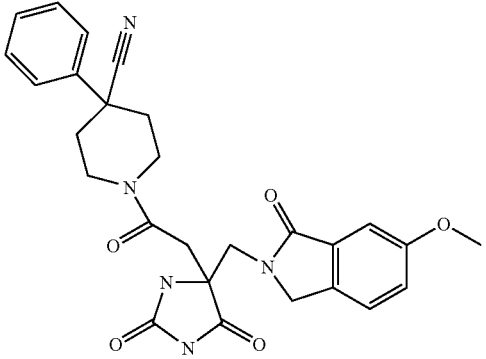 | 501.20 | 502.3[M + H]+ | B |
| 17 | 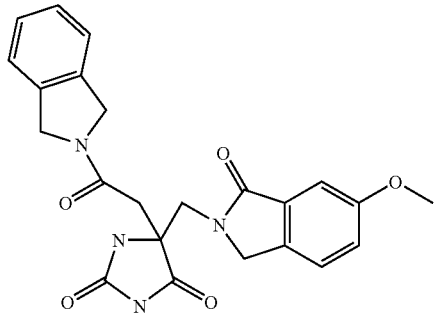 | 434.16 | 435.07[M + H]+ | B |
| 18 | 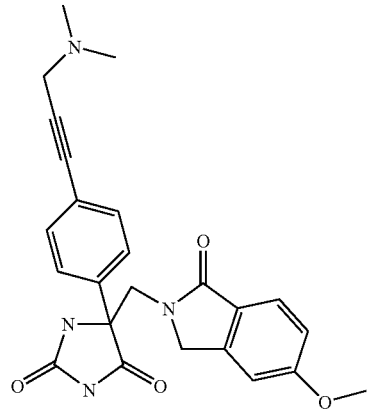 | 432.18 | 433.2[M + H]+ | A |
| 19 | 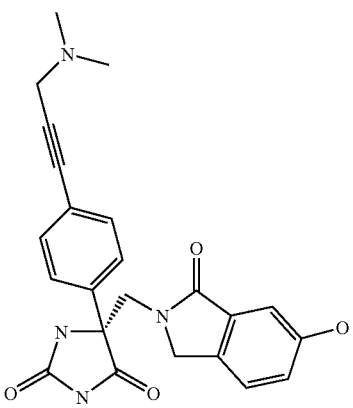 | 418.16 | 419.2[M + H]+ | B |

TABLE 1-continued

| Compound ID | Structures | Exact Mass | Mass Obsvd | Ki Rating |
|---|---|---|---|---|
| 20 | 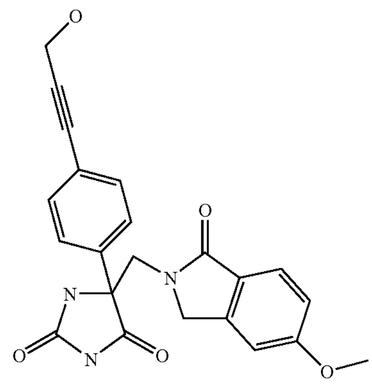 | 405.13 | 406.2[M + H]+ | A |
| 21 | 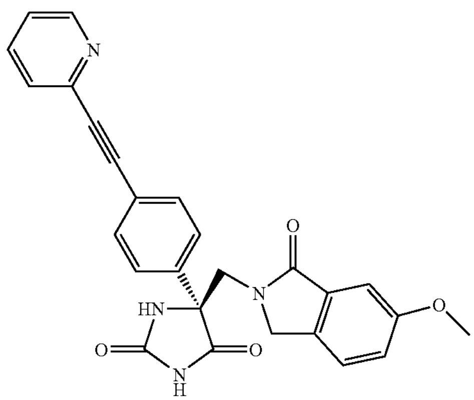 | 452.15 | 453.2[M + H]+ | B |
| 22 | 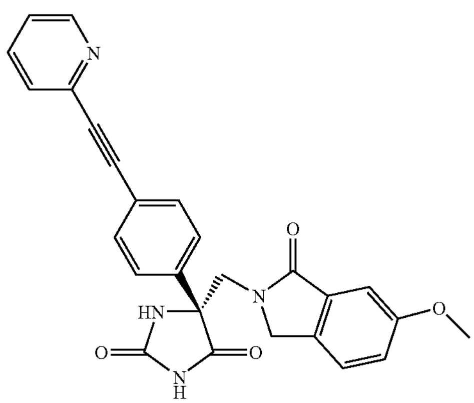 | 452.15 | 453.2[M + H]+ | A |
| 23 | 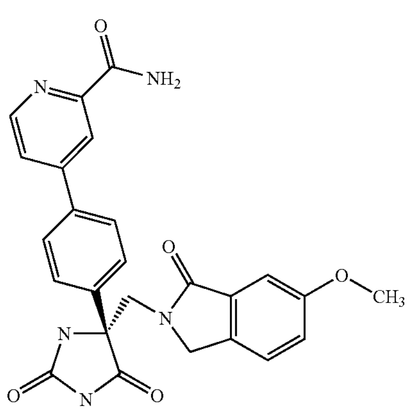 | 471.15 | 472.3[M + H]+ | A |

TABLE 1-continued

| Compound ID | Structures | Exact Mass | Mass Obsvd | Ki Rating |
|---|---|---|---|---|
| 24 | 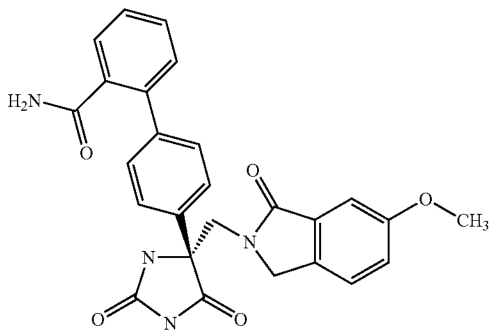 | 470.16 | 471.3[M + H]+ | A |
| 25 | 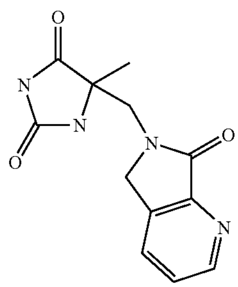 | 260.09 | 261.1[M + H]+ | D |
| 26 | 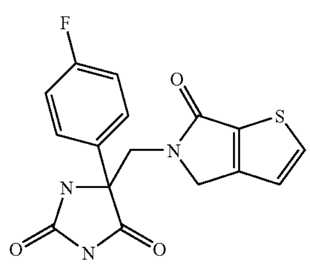 | 345.35 | 346.2[M + H]+ | B |
| 27 | 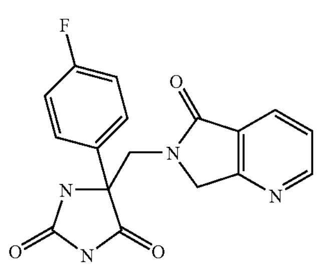 | 340.31 | 341.2[M + H]+ | D |
| 28 | 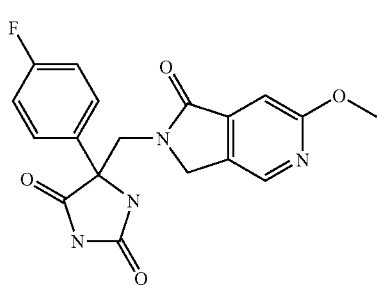 | 370.11 | 371.1[M + H] | A |

TABLE 1-continued

| Compound ID | Structures | Exact Mass | Mass Obsvd | Ki Rating |
|---|---|---|---|---|
| 29 | 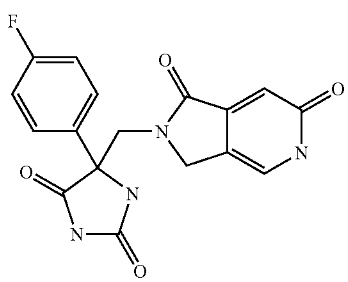 | 356.09 | 357.1[M + H] | B |
| 30 | 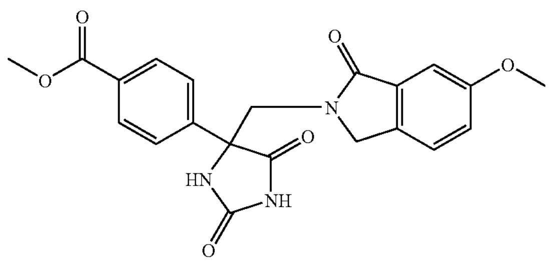 | 409.13 | 410.1[M + H]$^+$ | A |
| 31 | 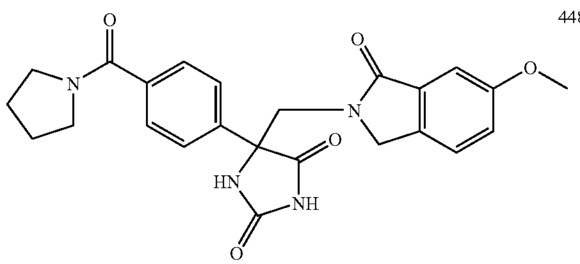 | 448.17 | 449.2[M + H]$^+$ | A |
| 32 | 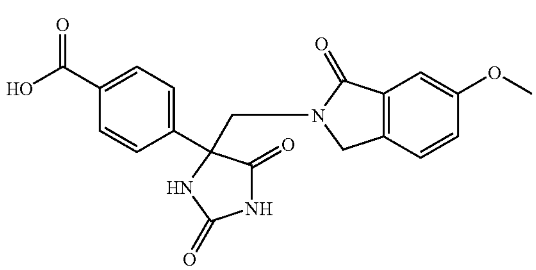 | 395.11 | 396.1[M + H]$^+$ | A |
| 33 | 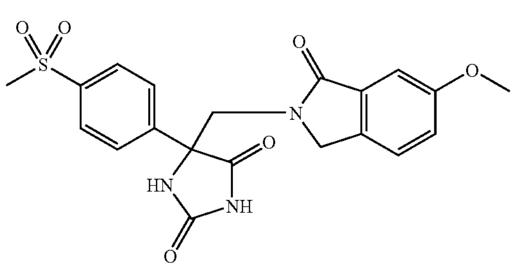 | 429.10 | 430.0[M + H]$^+$ | A |

TABLE 1-continued

| Compound ID | Structures | Exact Mass | Mass Obsvd | Ki Rating |
|---|---|---|---|---|
| 34 | 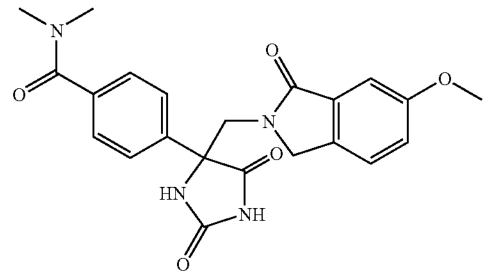 | 422.16 | 423.0[M + H]+ | B |
| 35 | 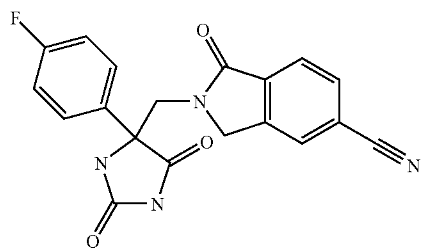 | 364.10 | 365.0[M + H]+ | B |
| 36 | 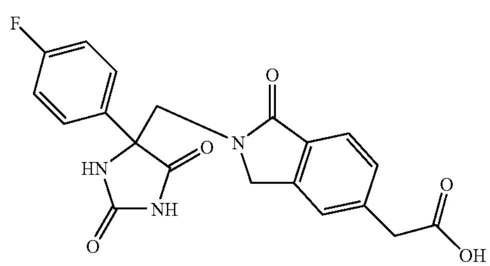 | 397.11 | 398.0[M + H]+ | C |
| 37 | 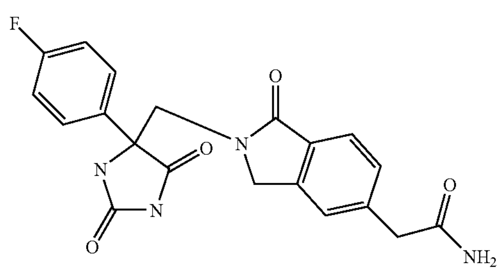 | 396.12 | 397.1[M + H]+ | B |
| 38 | 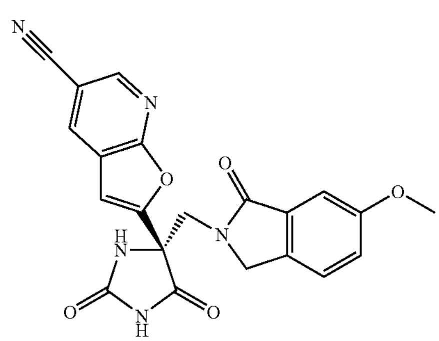 | 417.11 | 418.1[M + H]+ | A |

TABLE 1-continued

| Compound ID | Structures | Exact Mass | Mass Obsvd | Ki Rating |
|---|---|---|---|---|
| 39 | 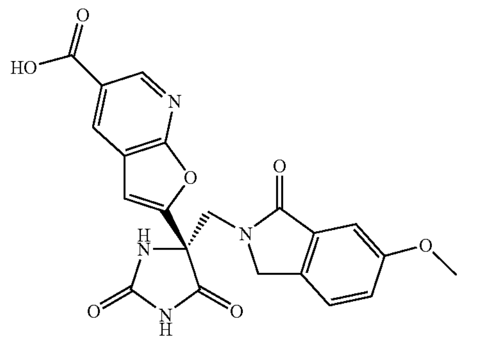 | 436.10 | 437.0[M + H]+ | A |
| 40 | 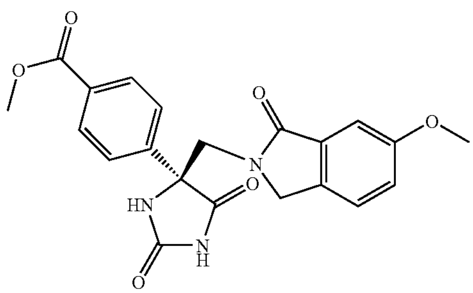 | 409.13 | 410.1[M + H]+ | B |
| 41 | 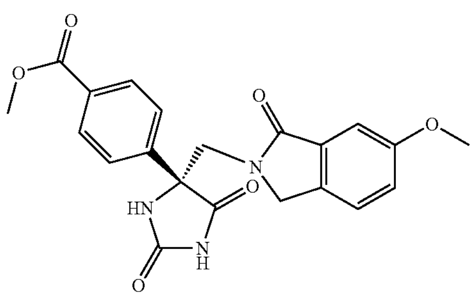 | 409.13 | 410.1[M + H]+ | A |
| 42 | 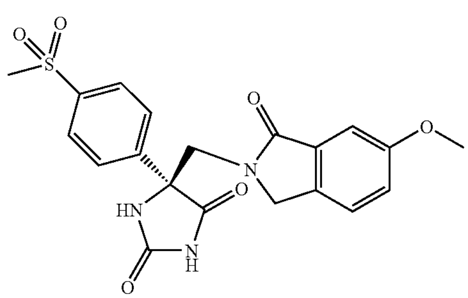 | 429.10 | 430.1[M + H]+ | C |
| 43 | 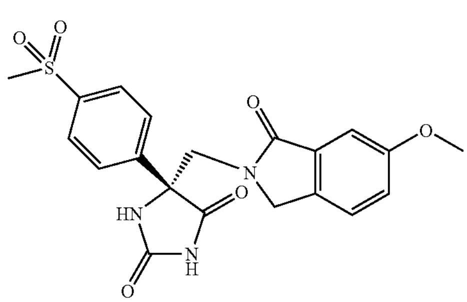 | 429.10 | 430.1[M + H]+ | A |

TABLE 1-continued

| Compound ID | Structures | Exact Mass | Mass Obsvd | Ki Rating |
|---|---|---|---|---|
| 44 | 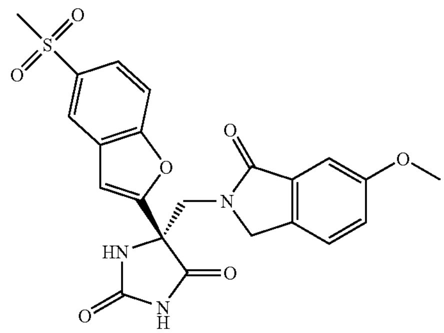 | 469.09 | 470.0[M + H]+ | A |
| 45 | 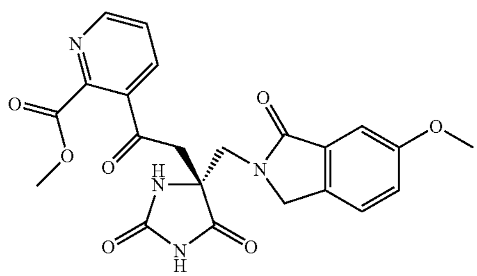 | 452.13 | 453.2[M + H]+ | B |
| 46 | 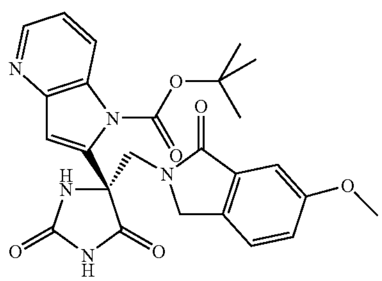 | 491.184 | 492.3[M + H]+ | A |
| 47 | 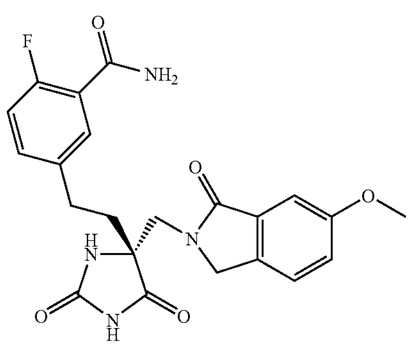 | 440.1 | 441.2[M + H]+ | B |
| 48 | 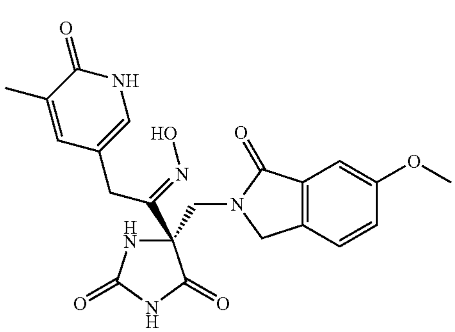 | 439.15 | 440.4[M + H]+ | B |

TABLE 1-continued

| Compound ID | Structures | Exact Mass | Mass Obsvd | Ki Rating |
| --- | --- | --- | --- | --- |
| 49 | 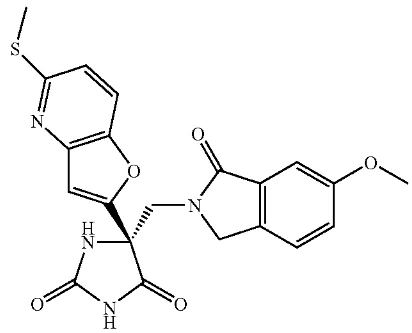 | 438.10 | 439.5[M + H]+ | A |
| 50 | 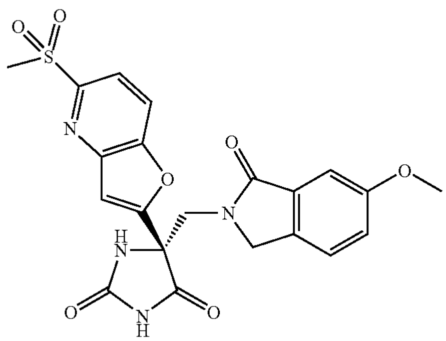 | 470.09 | 471.5[M + H]+ | A |
| 51 | 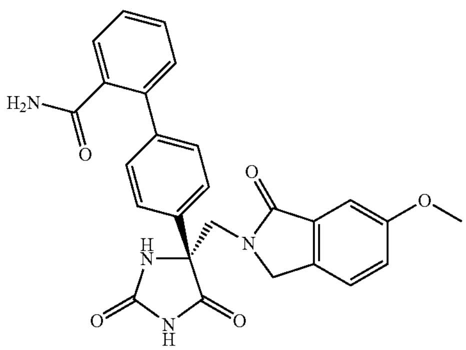 | 470.47 | 471.3[M + H]+ | A |
| 52 | 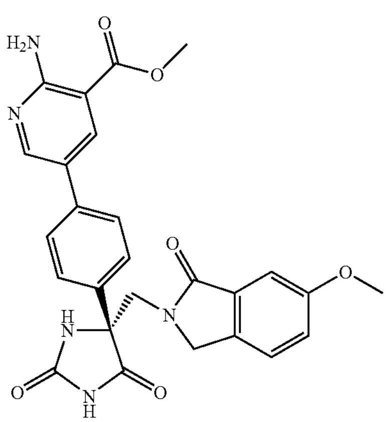 | 501.49 | 502.7[M + H]+ | A |

TABLE 1-continued

| Compound ID | Structures | Exact Mass | Mass Obsvd | Ki Rating |
|---|---|---|---|---|
| 53 | 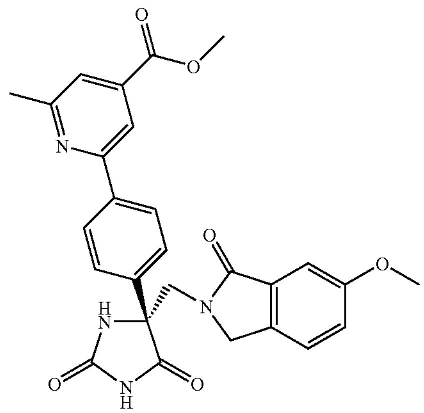 | 500.50 | 501.3[M + H]+ | A |
| 54 | 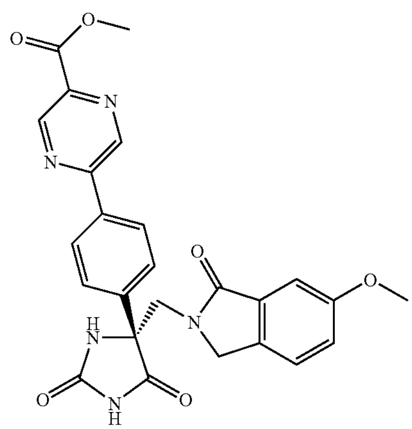 | 487.46 | 488.3[M + H]+ | A |
| 55 | 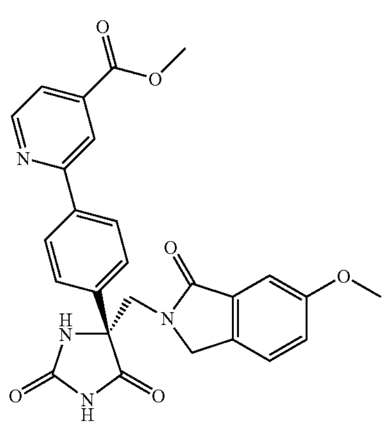 | 486.48 | 487.3[M + H]+ | A |

TABLE 1-continued
| Compound ID | Structures | Exact Mass | Mass Obsvd | Ki Rating |
|---|---|---|---|---|
| 56 | 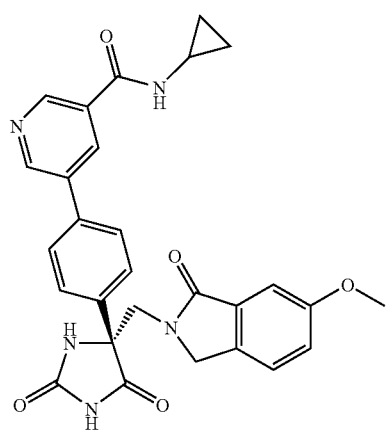 | 511.53 | 512.3[M + H]+ | A |
| 57 | 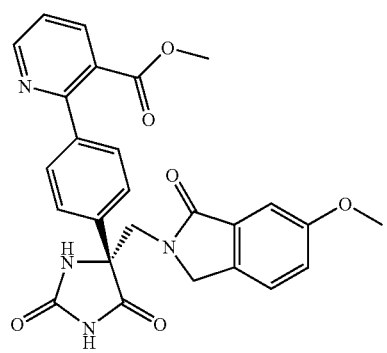 | 486.48 | 487.3[M + H]+ | A |
| 58 | 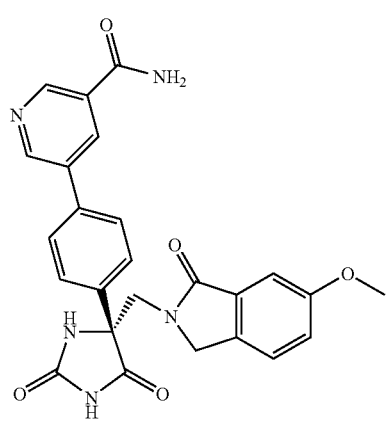 | 471.46 | 472.3[M + H]+ | A |

TABLE 1-continued

| Compound ID | Structures | Exact Mass | Mass Obsvd | Ki Rating |
|---|---|---|---|---|
| 59 | 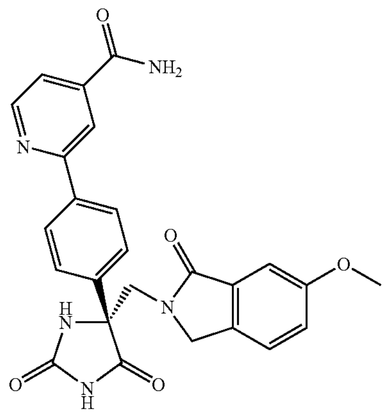 | 471.46 | 472.3[M + H]+ | A |
| 60 | 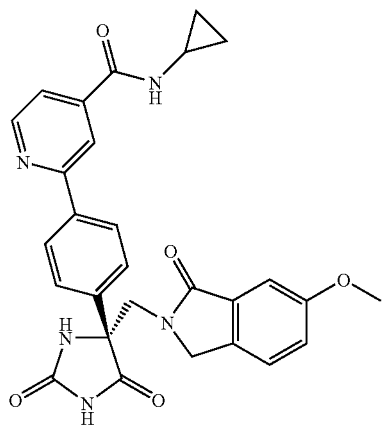 | 511.53 | 512.3[M + H]+ | A |
| 61 | 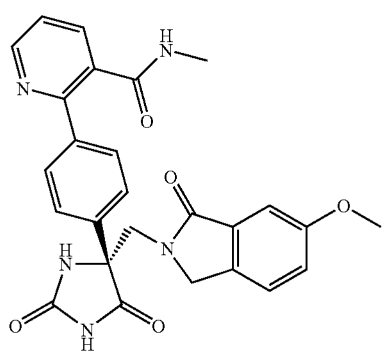 | 485.49 | 486.3[M + H]+ | A |
| 62 | 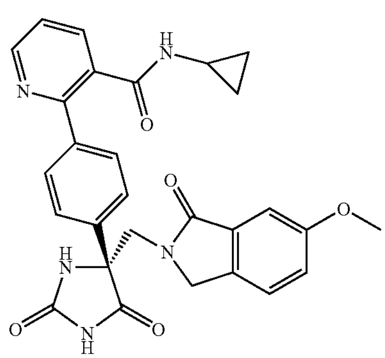 | 511.53 | 512.3[M + H]+ | A |

TABLE 1-continued

| Compound ID | Structures | Exact Mass | Mass Obsvd | Ki Rating |
|---|---|---|---|---|
| 63 | 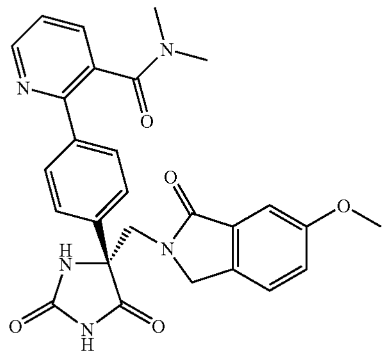 | 499.52 | 500.3[M + H]+ | A |
| 64 | 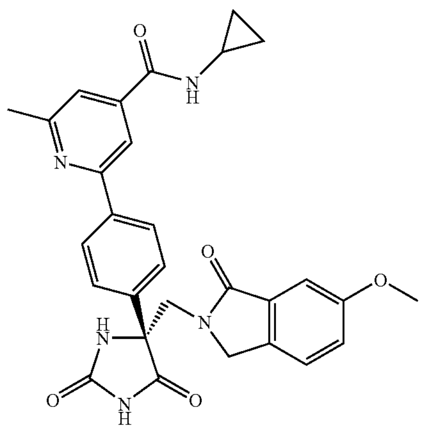 | 525.56 | 526.3[M + H]+ | A |
| 65 | 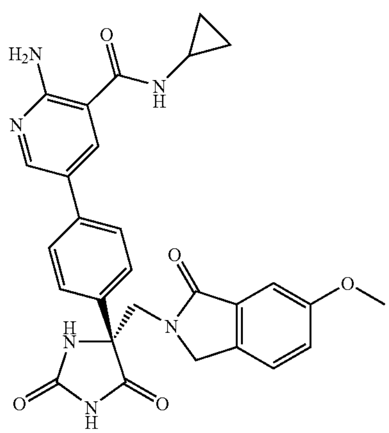 | 526.54 | 527.3[M + H]+ | A |
| 66 | 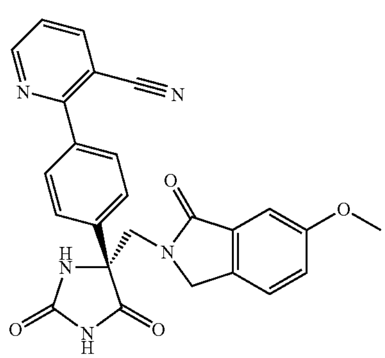 | 453.45 | 454.2[M + H]+ | A |

TABLE 1-continued

| Compound ID | Structures | Exact Mass | Mass Obsvd | Ki Rating |
|---|---|---|---|---|
| 67 | 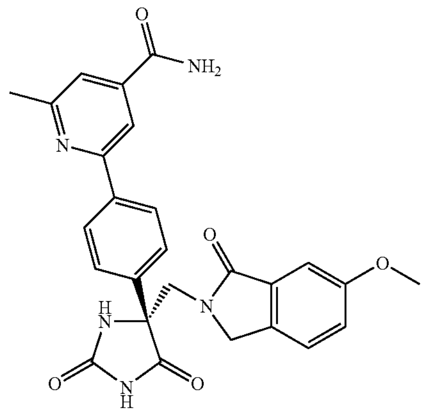 | 485.49 | 486.3[M + H]⁺ | A |
| 68 | 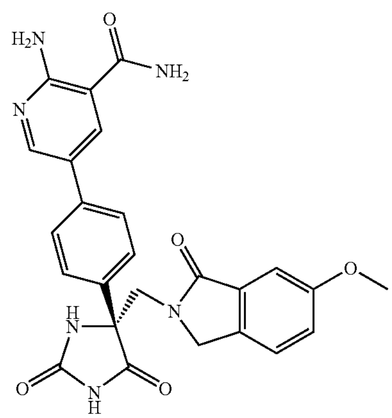 | 486.48 | 487.3[M + H]⁺ | A |
| 69 | 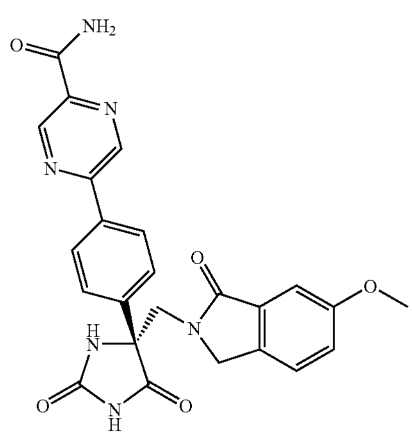 | 472.45 | 473.1[M + H]⁺ | A |

TABLE 1-continued

| Compound ID | Structures | Exact Mass | Mass Obsvd | Ki Rating |
|---|---|---|---|---|
| 70 | 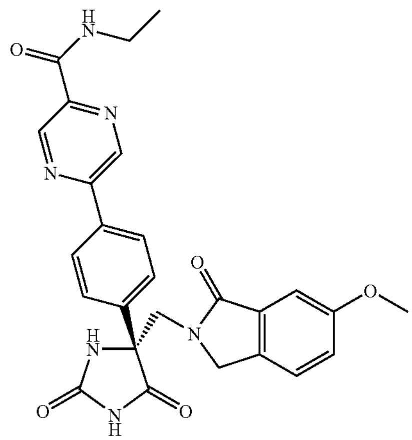 | 500.51 | 501.3[M + H]+ | A |
| 71 | 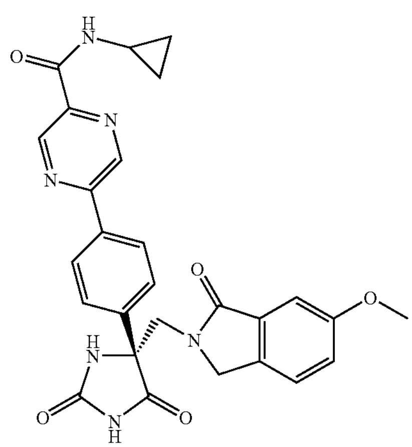 | 512.52 | 513.3[M + H]+ | A |
| 72 | 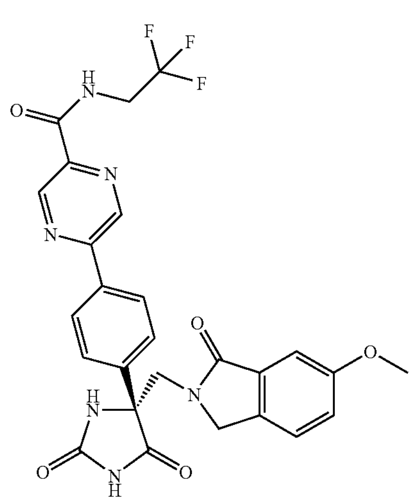 | 554.48 | 555.3[M + H]+ | A |

TABLE 1-continued
| Compound ID | Structures | Exact Mass | Mass Obsvd | Ki Rating |
|---|---|---|---|---|
| 73 | 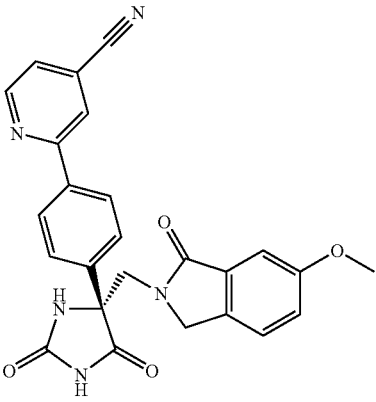 | 453.45 | 454.2[M + H]+ | A |
| 74 | 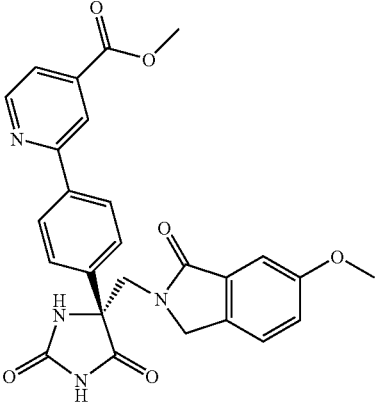 | 486.48 | 487.3[M + H]+ | A |
| 75 | 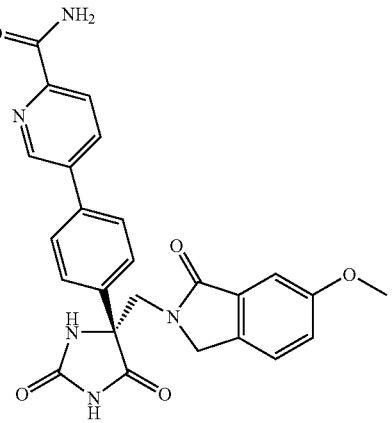 | 471.15 | 472.3[M + H]+ | A |

TABLE 1-continued

| Compound ID | Structures | Exact Mass | Mass Obsvd | Ki Rating |
|---|---|---|---|---|
| 76 | 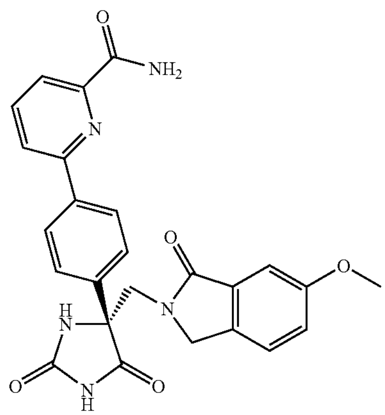 | 471.15 | 472.3[M + H]+ | A |
| 77 | 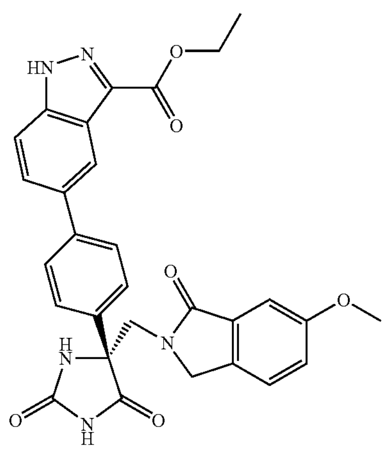 | 539.18 | 540.5[M + H]+ | A |
| 78 | 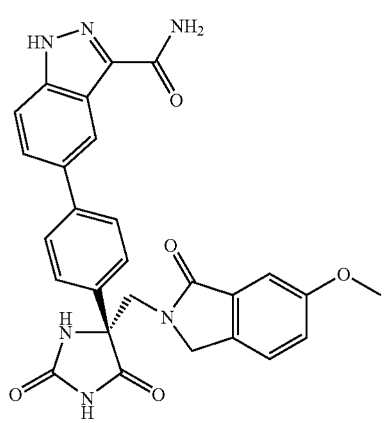 | 510.17 | 511.5[M + H]+ | A |

TABLE 1-continued

| Compound ID | Structures | Exact Mass | Mass Obsvd | Ki Rating |
|---|---|---|---|---|
| 79 | 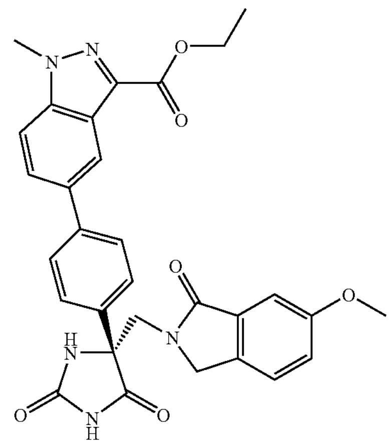 | 553.20 | 554.5[M + H]+ | TBD |
| 80 | 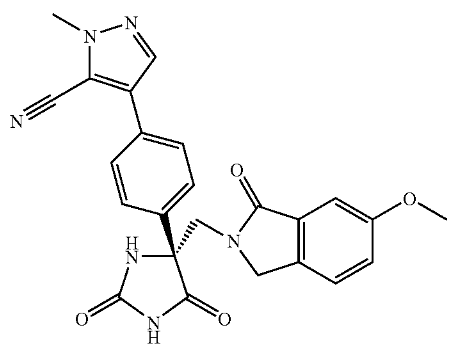 | 456.15 | 457.5[M + H]+ | A |
| 81 | 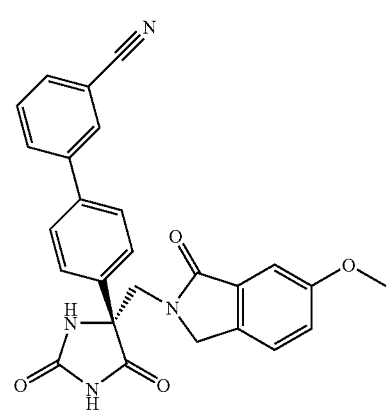 | 452.46 | 453.2[M + H]+ | A |

TABLE 1-continued

| Compound ID | Structures | Exact Mass | Mass Obsvd | Ki Rating |
|---|---|---|---|---|
| 82 | 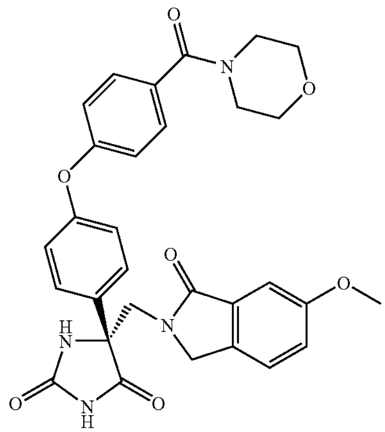 | 556.2 | 557.3[M + H]⁺ | A |
| 83 | 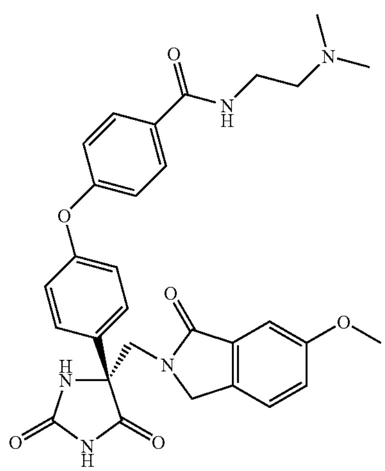 | 557.2 | 558.3[M + H]⁺ | A |
| 84 | 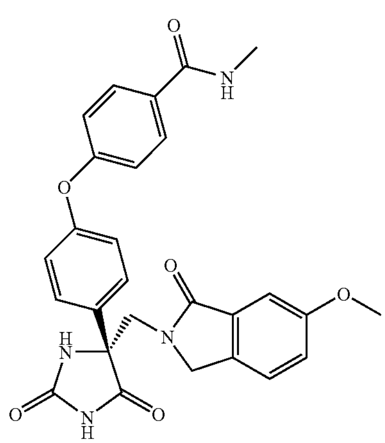 | 500.2 | 501.3[M + H]⁺ | A |

TABLE 1-continued

| Compound ID | Structures | Exact Mass | Mass Obsvd | Ki Rating |
|---|---|---|---|---|
| 85 | 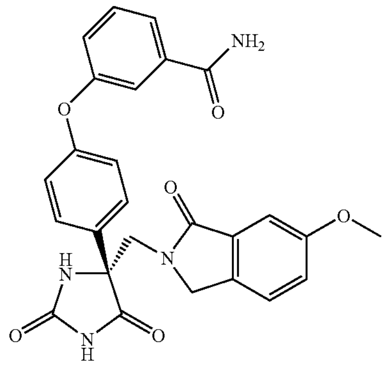 | 486.1 | 487.3[M + H]+ | A |
| 86 | 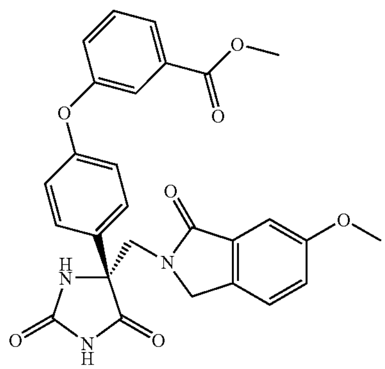 | 501.2 | 502.3[M + H]+ | A |
| 87 | 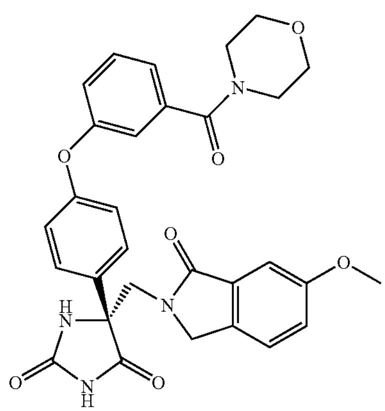 | 556.2 | 557.3[M + H]+ | A |
| 88 | 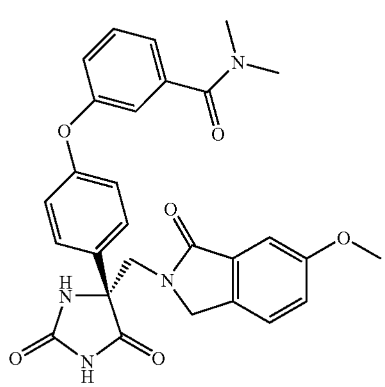 | 514.2 | 515.3[M + H]+ | A |

TABLE 1-continued

| Compound ID | Structures | Exact Mass | Mass Obsvd | Ki Rating |
|---|---|---|---|---|
| 89 | 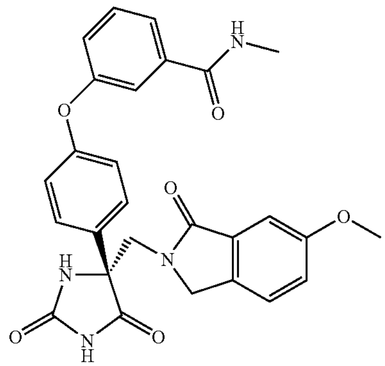 | 500.2 | 501.3[M + H]+ | A |
| 90 | 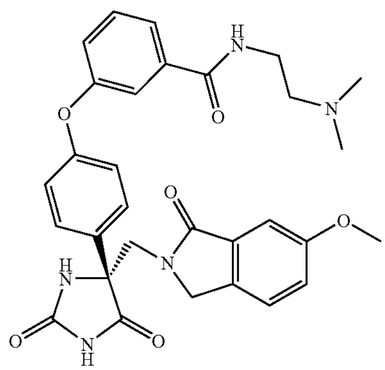 | 557.2 | 558.3[M + H]+ | A |
| 91 | 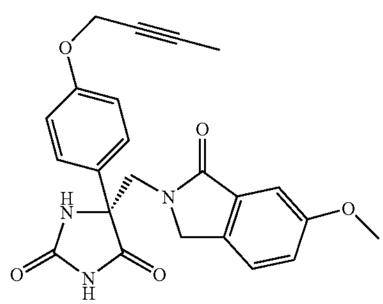 | 419.2 | 420.2[M + H]+ | A |
| 92 | 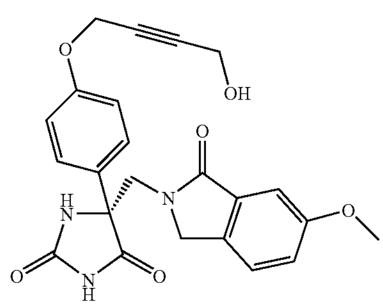 | 435.1 | 436.2[M + H]+ | A |

TABLE 1-continued

| Compound ID | Structures | Exact Mass | Mass Obsvd | Ki Rating |
|---|---|---|---|---|
| 93 | 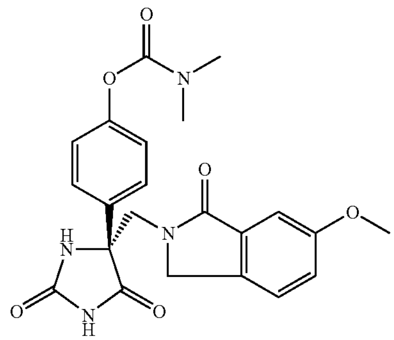 | 438.2 | 439.2[M + H]+ | A |
| 94 | 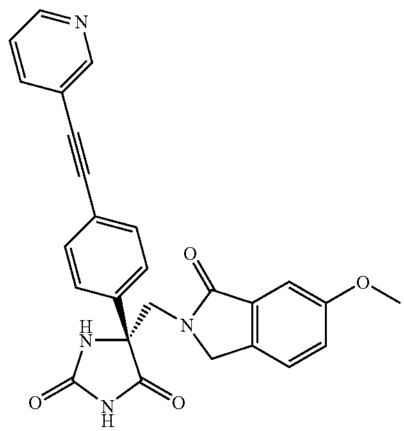 | 452.15 | 453.2[M + H]+ | A |
| 95 | 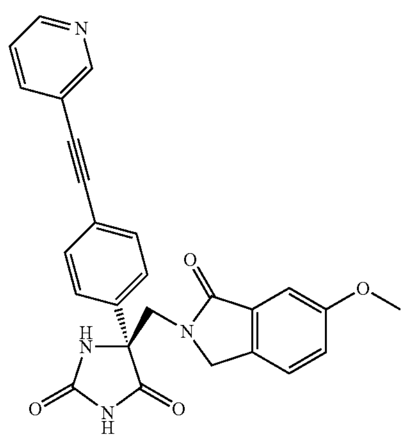 | 452.15 | 453.2[M + H]+ | B |
| 96 | 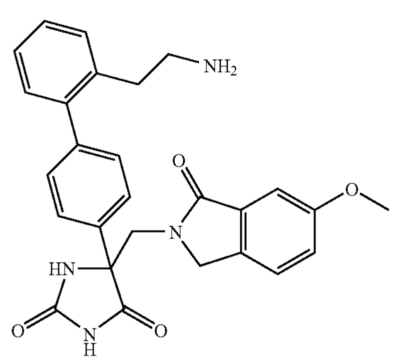 | 470.20 | 471.3[M + H]+ | B |

TABLE 1-continued

| Compound ID | Structures | Exact Mass | Mass Obsvd | Ki Rating |
|---|---|---|---|---|
| 97 | 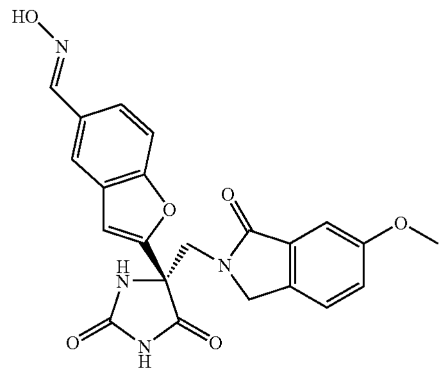 | 434.12 | 435.2[M + H]+ | A |
| 98 | 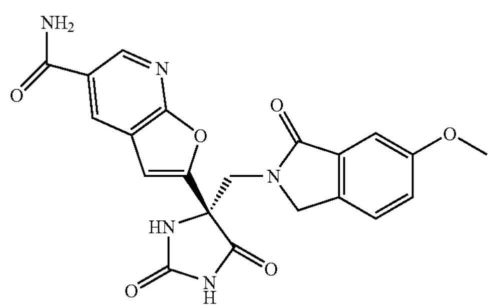 | 435.12 | 436.1[M + H]+ | A |
| 99 | 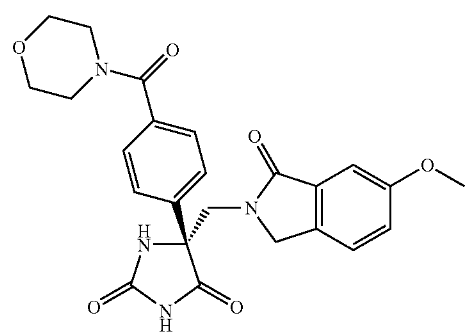 | 464.17 | 465.3[M + H]+ | A |
| 100 | 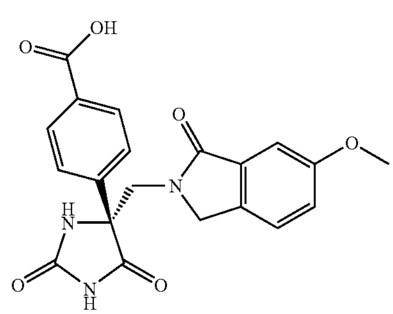 | 395.11 | 396.2[M + H]+ | A |

TABLE 1-continued

| Compound ID | Structures | Exact Mass | Mass Obsvd | Ki Rating |
|---|---|---|---|---|
| 101 | 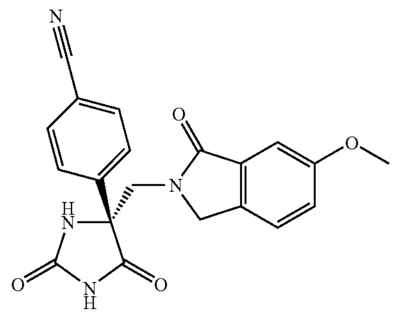 | 376.12 | 377.2[M + H]+ | A |
| 102 | 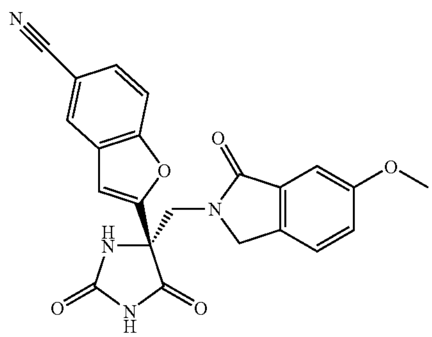 | 416.11 | 417.2[M + H]+ | A |
| 103 | 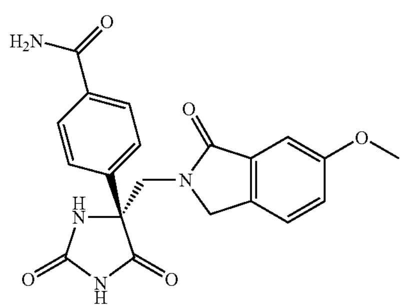 | 394.13 | 395.2[M + H]+ | A |
| 104 | 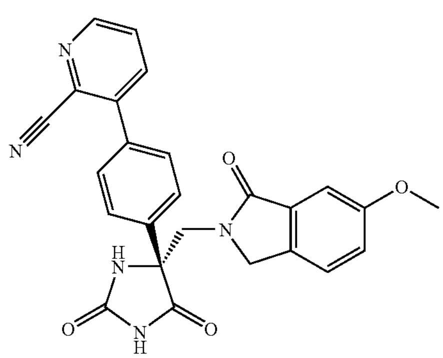 | 453.14 | 454.2[M + H]+ | A |

TABLE 1-continued

| Compound ID | Structures | Exact Mass | Mass Obsvd | Ki Rating |
|---|---|---|---|---|
| 105 | 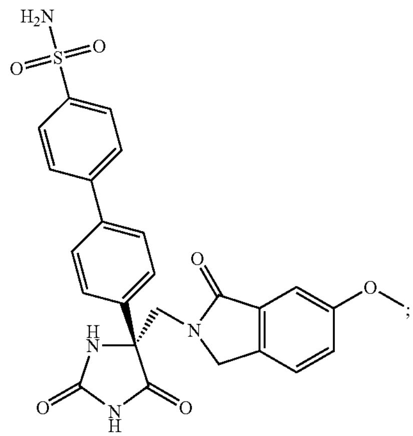 | 506.13 | 507.3[M + H]⁺ | A |

In another embodiment, the compound of Formula (I) is selected from the group consisting of:

| Compound ID | Structures |
|---|---|
| 98 | 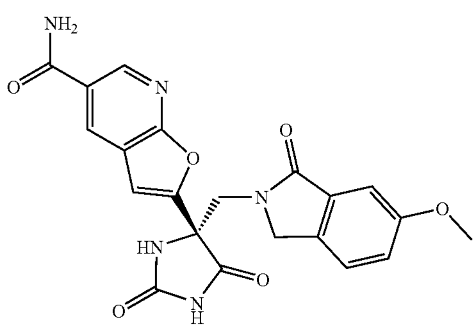 |
| 68 | 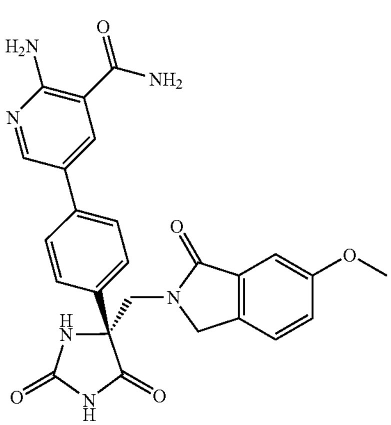 |

| Compound ID | Structures |
|---|---|
| 85 | 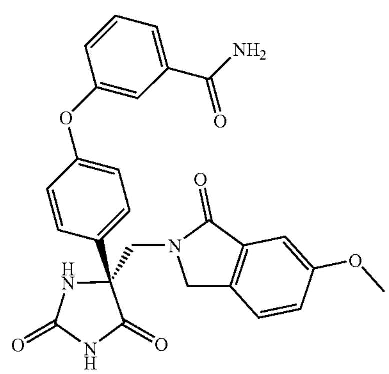 |
| 84 | 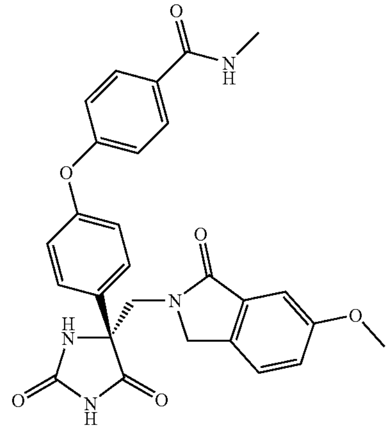 |

| Compound ID | Structures |
|---|---|
| 43 | 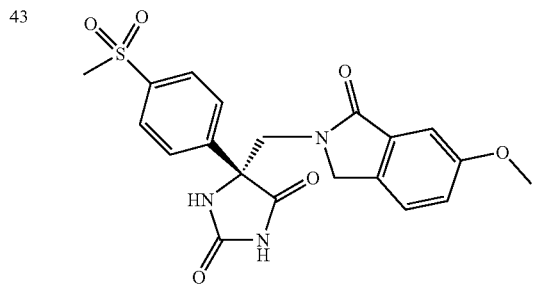 |
| 97 | 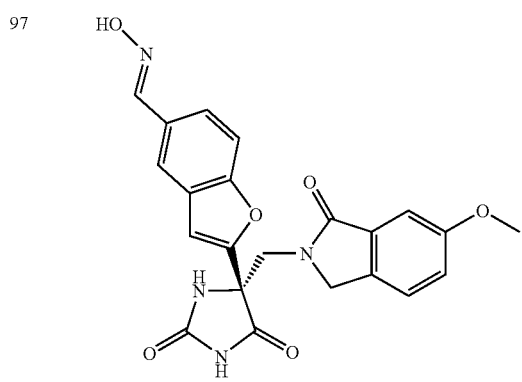 |
| 66 | 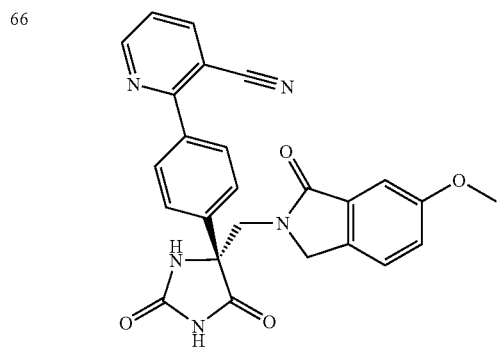 |
| Compound ID | Structures |
|---|---|
| 64 | 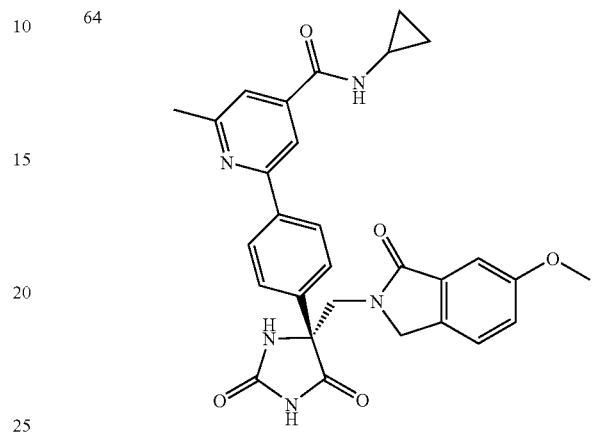 |
| 50 | 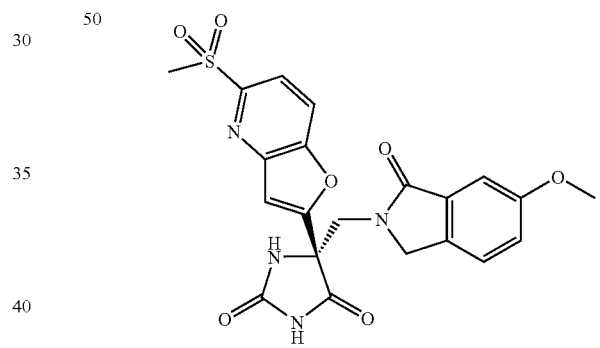 |
| 76 | 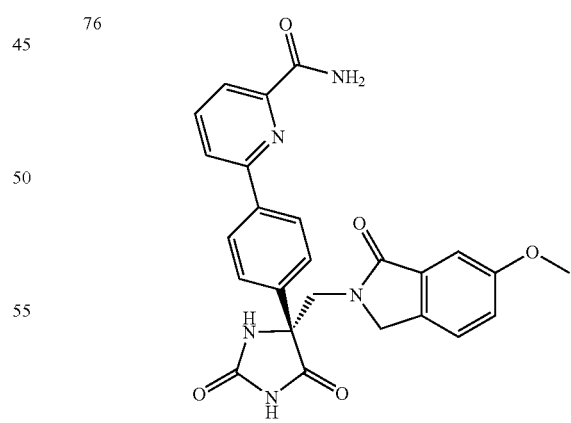 |
or a pharmaceutically acceptable salt, solvate, or ester thereof.
Specific TACE inhibitory activity (Ki values) of some representative compounds of the present invention are set forth below.

| Compound ID | Structures | Exact Mass | Mass Obsvd | Ki (nM) |
|---|---|---|---|---|
| 98 | 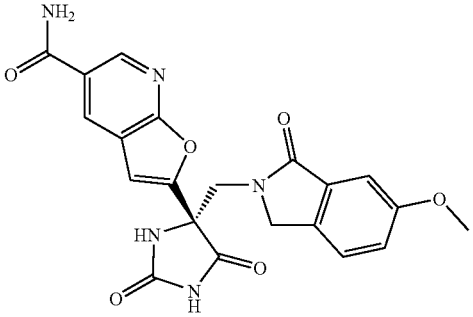 | 435.12 | 436.1 [M + H]+ | 0.71 |
| 68 | 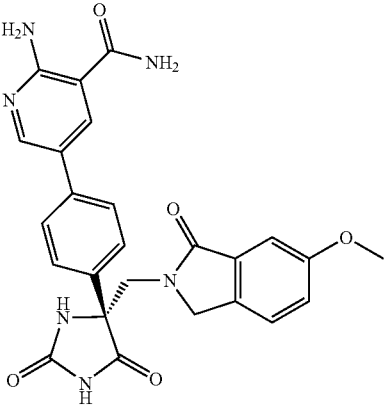 | 486.48 | 487.3 [M + H]+ | 0.23 |
| 85 | 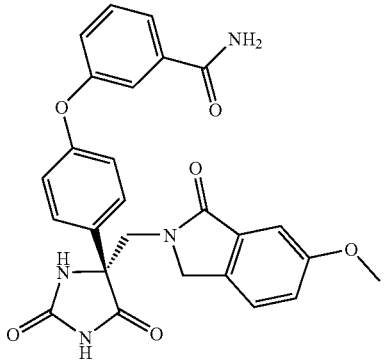 | 486.1 | 487.3 [M + H]+ | 0.46 |
| 84 | 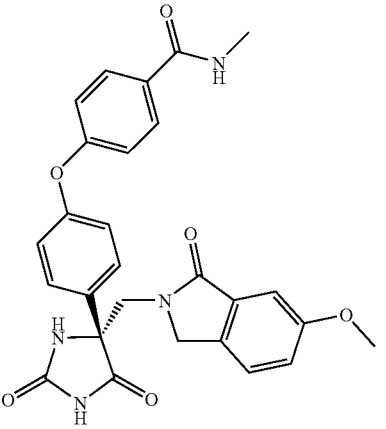 | 500.2 | 501.3 [M + H]+ | 4.0 |

-continued
| Compound ID | Structures | Exact Mass | Mass Obsvd | Ki (nM) |
|---|---|---|---|---|
| 43 | 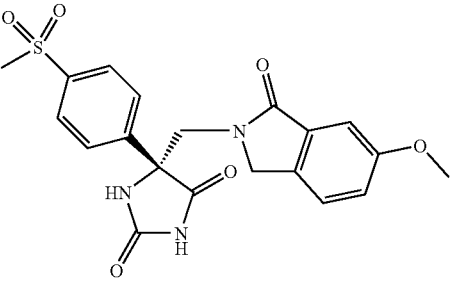 | 429.10 | 430.1 [M + H]+ | 0.26 |
| 97 | 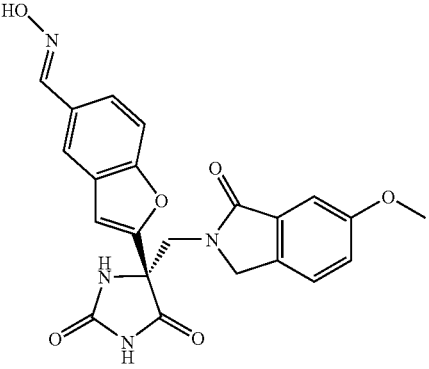 | 434.12 | 435.2 [M + H]+ | 0.39 |
| 66 | 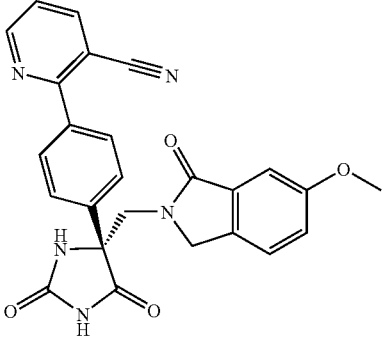 | 453.45 | 454.2 [M + H]+ | 0.09 |
| 64 | 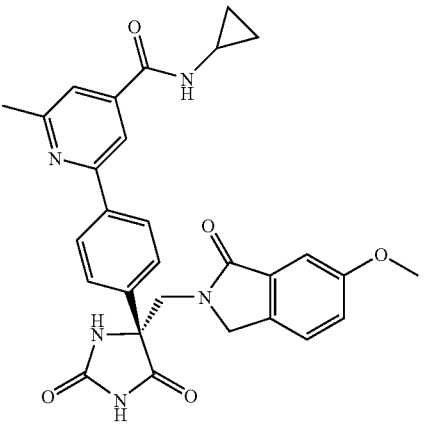 | 525.56 | 526.3 [M + H]+ | 0.15 |

-continued

| Compound ID | Structures | Exact Mass | Mass Obsvd | Ki (nM) |
|---|---|---|---|---|
| 50 | 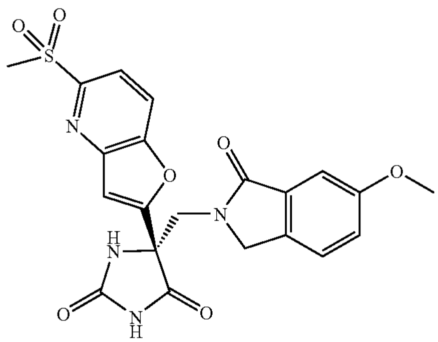 | 470.09 | 471.5 [M + H]⁺ | 1.04 |
| 76 | 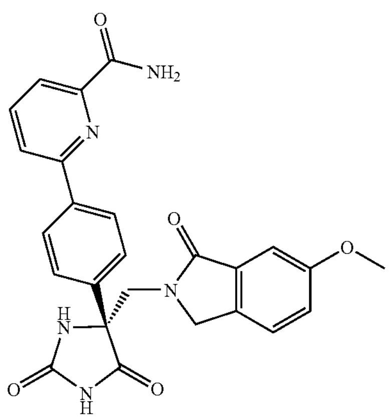 | 471.15 | 472.3 [M + H]⁺ | 0.66 |

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain.

"Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Halogen" (or "halo") means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylhet- eroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), G$_1$G$_2$N—, G$_1$G$_2$N-alkyl-, G$_1$G$_2$NC(O)—, G$_1$G$_2$NSO$_2$— and —SO$_2$NG$_1$G$_2$, wherein G$_1$ and G$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

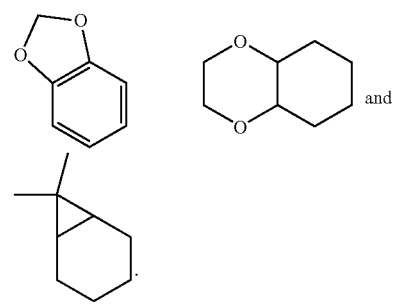

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

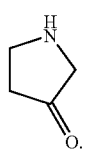

It should be noted that tautomeric forms such as, for example, the moieties:

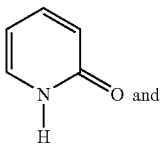 and 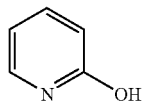

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems,"Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and Q-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino $(C_1-C_4)$alkyl or mono-N- or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting TACE, the production of TNF-α, MMPs, ADAMS or any combination thereof and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I, and of the salts, solvates and prodrugs of the compounds of Formula I, are intended to be included in the present invention.

The compounds according to the invention have pharmacological properties; in particular, the compounds of Formula I can be inhibitors of TACE, aggrecanase, TNF-α and/or MMP activity.

In one aspect, the invention provides a pharmaceutical composition comprising as an active ingredient at least one compound of formula (I).

In another aspect, the invention provides a pharmaceutical composition of formula (I) additionally comprising at least one pharmaceutically acceptable carrier.

In another aspect, the invention provides a method of treating disorders associated with TACE, aggrecanase, TNF-α, MMPs, ADAMs or any combination thereof, said method comprising administering to a patient in need of such treatment an effective amount of at least one compound of formula (I).

In another aspect, the invention provides a use of a compound of formula (I) for the manufacture of a medicament to treat disorders associated with TACE, aggrecanase, TNF-α, MMPs, ADAMs or any combination thereof.

The compounds of Formula (I) can have anti-inflammatory activity and/or immunomodulatory activity and can be useful in the treatment of diseases including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, OA and RA, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

In another aspect, the invention provides a method of preparing a pharmaceutical composition for treating the disorders associated with TACE, aggrecanase, TNF-α, MMPs, ADAMs or any combination thereof, said method comprising bringing into intimate contact at least one compound of formula (I) and at least one pharmaceutically acceptable carrier.

In another aspect, the invention provides a compound of formula (I) exhibiting TACE, TNF-α, MMPs, ADAMs or any combination thereof inhibitory activity, including enantiomers, stereoisomers and tautomers of said compound, and pharmaceutically acceptable salts, solvates, or esters of said compound, said compound being selected from the compounds of structures listed in Table 1 set forth above.

In another aspect, the invention provides a pharmaceutical composition for treating disorders associated with TACE, aggrecanase, TNF-α, MMP, ADAM or any combination thereof in a subject comprising, administering to the subject in need of such treatment a therapeutically effective amount of at least one compound of formula (I) or a pharmaceutically acceptable salt, solvate, ester, or isomer thereof.

In another aspect, the invention provides a compound of formula (I) in purified form.

In another aspect, the invention provides a method of treating a condition or disease mediated by TACE, MMPs, TNF-α, aggrecanase, or any combination thereof in a subject comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection in a subject comprising administering to the subject in need of such treatment a therapeutically effective amount of at least one compound of formula (I) or a pharmaceutically acceptable salt, solvate, ester, or isomer thereof.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with COPD, comprising: administering to the subject in need of such treatment a therapeutically effective amount of at least one compound of Formula (I) or a pharmaceutically acceptable salt, solvate, ester or isomer thereof.

In another aspect, the invention provides a method of treating a condition or disease associated with rheumatoid arthritis, comprising: administering to the subject in need of such treatment a therapeutically effective amount of at least one compound of formula (I) or a pharmaceutically acceptable salt, solvate, ester, or isomer thereof.

In another aspect, the invention provides a method of treating a condition or disease associated with Crohn's disease, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with psoriasis, comprising: administering to the subject in need of such treatment a therapeutically effective amount of at least one compound of formula (I) or a pharmaceutically acceptable salt, solvate, ester, or isomer thereof.

In another aspect, the invention provides a method of treating a condition or disease associated with ankylosing spondylitis, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with sciatica, comprising: administering to the subject in need of such treatment a therapeutically effective amount of at least one compound of formula (I) or a pharmaceutically acceptable salt, solvate, ester or isomer thereof.

In another aspect, the invention provides a method of treating a condition or disease associated with complex regional pain syndrome, comprising: administering to the subject in need of such treatment a therapeutically effective amount of at least one compound of formula (I) or a pharmaceutically acceptable salt, solvate, ester, or isomer thereof.

In another aspect, the invention provides a method of treating a condition or disease associated with psoriatic arthritis, comprising: administering to the subject in need of such treatment a therapeutically effective amount of at least one compound of formula (I), or a pharmaceutically acceptable salt, solvate, ester, or isomer thereof.

In another aspect, the invention provides a method of treating a condition or disease associated with multiple sclerosis, comprising: administering to the subject in need of such treatment a therapeutically effective amount of at least one compound of formula (I) or a pharmaceutically acceptable salt, solvate, ester or isomer thereof, in combination with a compound selected from the group consisting of Avonex□, Betaseron, Copaxone or other compounds indicated for the treatment of multiple sclerosis.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with non-steroidal anti-inflammatory drugs (NSAIDs) such as piroxicam, naproxen, indomethacin, ibuprofen and the like; cycloxygenase-2 selective (COX-2) inhibitors such as Vioxx□ and Celebrex□; immunosuppressives such as steroids, cyclosporin, Tacrolimus, rapamycin and the like; biological response modifiers (BRMs) such as Enbrel□, Remicade□, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors, chemokine receptor antagonists, Thalidomide and other small molecule inhibitors of pro-inflammatory cytokine production.

Also, a compound of the present invention may be co-administered or used in combination with an $H_1$ antagonist for the treatment of seasonal allergic rhinitis and/or asthma. Suitable $H_1$ antagonists may be, for example, Claritin®, Clarinex®, Allegra®, or Zyrtec®.

In another aspect, the invention provides a method of treating a condition or disease mediated by TACE, MMPs, TNF-α, aggrecanase, or any combination thereof in a subject comprising: administering to the subject in need of such treatment a therapeutically effective amount of at least one compound of formula (I) or a pharmaceutically acceptable salt, solvate or isomer thereof in combination with a therapeutically effective amount of at least one medicament selected from the group consisting of disease modifying anti-rheumatic drugs (DMARDS), NSAIDs, COX-2 inhibitors, COX-1 inhibitors, immunosuppressives, biological response modifiers (BRMs), anti-inflammatory agents and $H_1$ antagonists.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one compound of Formula (I) or a pharmaceutically acceptable salt, solvate, ester, or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one compound of Formula (I), or a pharmaceutically acceptable salt, solvate, ester or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method for treating RA comprising administering a compound of the formula I in combination with compound selected from the class consisting of a COX-2 inhibitor e.g. Celebrex® or Vioxx®); a COX-1 inhibitor e.g. Feldene®; an immunosuppressive e.g. methotrexate or cyclosporin; a steroid e.g. □-methasone; and anti-TNF-α compound, e.g. Enbrel® or Remicade®; a PDE IV inhibitor, or other classes of compounds indicated for the treatment of RA.

In another aspect, the invention provides a method for treating multiple sclerosis comprising administering a compound of the formula (I) in combination with a compound selected from the group consisting of Avonex®, Betaseron, Copaxone or other compounds indicated for the treatment of multiple sclerosis.

TACE activity is determined by a kinetic assay measuring the rate of increase in fluorescent intensity generated by TACE catalyzed cleavage of an internally quenched peptide substrate (SPDL-3). The purified catalytic domain of recombinant human TACE (rhTACEc, Residue 215 to 477 with two mutation (S266A and N452Q) and a 6×His tail) is used in the assay. It is purified from the baculovirus/Hi5 cells expression system using affinity chromatography. The substrate SPDL-3 is an internally quenched peptide (MCA-Pro-Leu-Ala-Gln-Ala-Val-Arg-Ser-Ser-Ser-Dpa-Arg-NH2), with its sequence derived from the pro-TNF□ cleavage site. MCA is (7-Methoxycoumarin-4-yl)acetyl. Dpa is N-3-(2,4-Dinitrophenyl)-L-2,3-diaminopropionyl.

A 50 µl assay mixture contains 20 mM HEPES, pH 7.3, 5 mM $CaCl_2$, 100 □M $ZnCl_2$, 2% DMSO, 0.04% Methylcellulose, 30 µM SPDL-3, 70 µM rhTACEc and a test compound. RhTACEc is pre-incubated with the testing compound for 90 min. at 25° C. Reaction is started by addition of the substrate. The fluorescent intensity (excitation at 320 nm, emission at 405 nm) was measured every 45 seconds for 30 min. using a fluorospectrometer (GEMINI XS, Molecular Devices). Rate of enzymatic reaction is shown as Units per second. Effect of a test compound is shown as % of TACE activity in the absence of the compound.

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release.

The term pharmaceutical composition is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsion. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of Formula I useful in the method of the present invention range from 0.01 to 1000 mg per day. More preferably, dosages range from 0.1 to 1000 mg/day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

The following abbreviations may be used in the procedures and schemes below:
ACN Acetonitrile
AcOH Acetic acid
Aq Aqueous
BOC tert-Butoxycarbonyl
$BOC_2O$ BOC Anhydride
C degrees Celsius
CBZCl Benzyl chloroformate
DBU 1,8-Diazabicyclo[5.4.0]undec-7-ene DCM Dichloromethane
DEAD Diethyl azodicarboxylate
(DHQ)2PHAL Hydroquinine 1,4-phthalazinediyl diether
DIAD Diisopropylazodicarboxylate
DIPEA Diisopropylethylamine
DMA N,N-Dimethylacetamide
DMAP 4-Dimethylaminopyridine
DME Dimethoxyethane
DMF Dimethylformamide
DMPU 1,3-Dimethyl-3,4,5,6-tetrahydro-2(1 h)-pyrimidinone
DMSO Dimethyl sulfoxide
EDCl 1-(3-Dimethylaminopropyl)-3-ethylcarbodiimide hydrochloride
EI Electron impact
eq Equivalents
EtOAc Ethyl acetate
EtOH Ethanol
g grams
h hours
hr hours
$^1$H proton
HATU N,N, N',N'-Tetramethyl-O-(7-Azabenzotriazol-1-yl) Uronium hexafluorophosphate
Hex hexanes
HOBT 1-Hydroxybenzotriazole
HMPA Hexamethyl phosphoramide
HPLC High pressure liquid chromatography
HPLC/MS High pressure liquid chromatography/Mass spectroscopy
LC/MS Liquid chromatorgraphy/mass spectroscopy
LAH Lithium aluminum hydride
LDA Lithium diisopropylamide
M Molar
mmol millimoles
mCPBA meta-Chloroperoxybenzoic acid
Me Methyl
MeCN Acetonitrile
MeOH Methanol
min Minutes
mg Milligrams
MHz Megahertz
mL Milliliter
MPLC Medium Pressure Liquid Chromatography
NMR Nuclear Magnetic Resonance
MS Mass Spectroscopy
NBS N-Bromosuccinimide
NMM N-Methylmorpholine
NMP 1-methyl-2-pyrrolidone
ON Overnight
PCC Pyridinium Chlorochromate
PTLC Preparative thin layer chromatography
PyBrOP Bromo-tris-pyrrolidino-phosphonium hexafluorophosphate
Pyr Pyridine
RT Room temperature
SEM 2-(Trimethylsilyl)-ethoxymethyl
sgc Silica gel 60 chromatography
tBOC tert-Butoxycarbonyl
TACE Tumor Necrosis Factor-alpha converting enzyme
TEA Triethylamine
TFA Trifluoroacetic acid
THF Tetrahydrofuran
TLC Thin layer chromatography
$T_R$ Retention time
X-PHOS 2-dicyclohexylphosphino-2',4',6'-tri-isopropyl-1',1-biphenyl

SYNTHETIC ROUTES AND EXAMPLES

Example 1

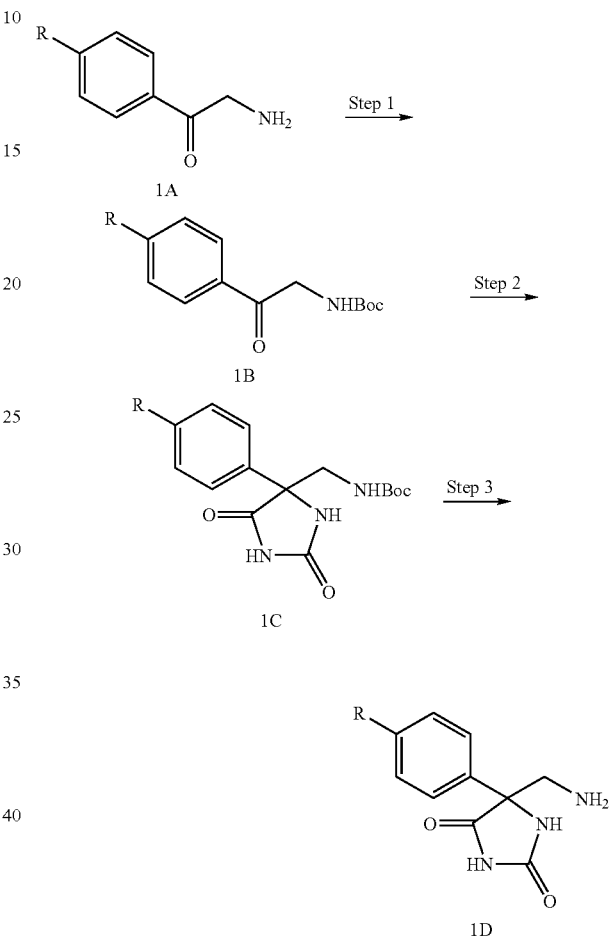

General Procedures for Example 1:

In step 1, Compound 1A (either commercially available, or prepared by a procedure similar to that described by Abdalla, G. M. and Sowell, J. W. *Journal of Heterocyclic Chemistry*, 1987, 24(2), 297-301) was treated with one equivalent of Di-tert-butyl dicarbonate in polar solvent, such as DMF, for 30 minutes to 12 hours. The solvent was removed and compound 1B could be used without further purification or purified by silica gel chromatography.

In step 2, compound 1 B was reacted with potassium cyanide and ammonium carbonate in an alcohol and water solution, at 50° C. to 90° C., for 5 hours to 48 hours. After cooling down, water was added and compound 1C could be collected by filtration.

In step 3, compound 1C was stirred with 2 to 20 equivalents of hydrogen chloride in methanol for 5 to 48 hours. After ethyl ether was added, compound 1 D could be collected by filtration.

Example 2

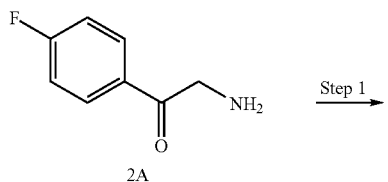
2A

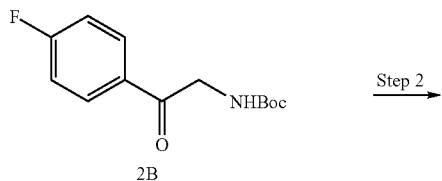
2B

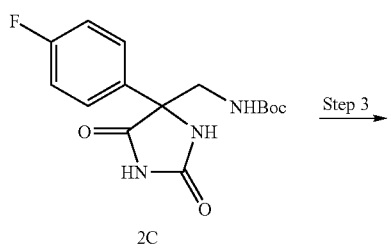
2C

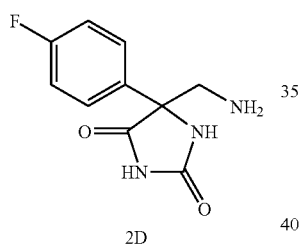
2D

Step 1

Compound 2A (Abdalla, G. M. and Sowell, J. W. *Journal of Heterocyclic Chemistry,* 1987, 24(2), 297-301) (Hydrochloride salt, 8.60 g, 45.4 mmol), triethyl amine (19.0 mL, 136 mmol), and di-tert-butyl dicarbonate (11.9 g, 54.4 mmol) were stirred in methylene chloride (100 mL) at 25° C. for 16 hours. Saturated aqueous $NaHCO_3$ (150 mL) was added. The aqueous layer was extracted with $CH_2Cl_2$ (100 mL) twice. The organic phase was washed with brine (100 mL) and dried over $Na_2SO_4$. The solvent was removed by rotary evaporator to give compound 2B which was used without further purification.

Step 2

Compound 2B (9.06 g, 35.8 mmol), KCN (3.49 g, 53.7 mmol), and $(NH_4)_2CO_3$ (12.0 g, 125.2 mmol) were suspended in a mixture of EtOH (35 mL) and water (35 mL). The solution was stirred at 70° C. for three days. After cooling down, water (35 mL) was added. The solid was filtered and washed with water three times. The solid was dried under vacuum at 40° C. for 16 hours to give compound 2C (7.9 g, 68%).

Step 3

Compound 2C (4.0 g) was suspended in methanol (50 mL) and HCl (4M in dioxane, 20 mL) was added. The solution was stirred at 25° C. for 3 hours. Ethyl ether (50 ml) was added. The solid was filtered, washed with ethyl ether twice, and dried under vacuum for 12 hours to give compound 2D (2.7 g, 84%).

Example 3

3A

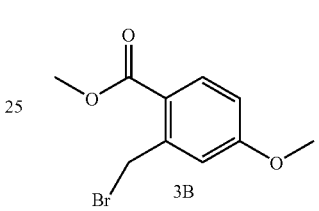
3B

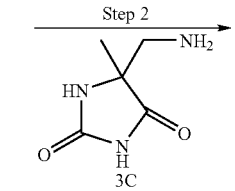
3C

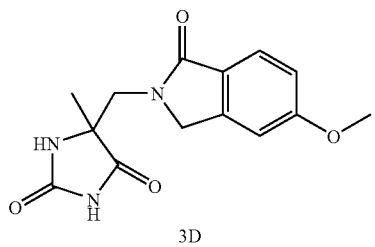
3D

Step 1

Compound 3A (prepared according to the procedure described by Wyrick, S. D. et al. *Journal of Medicinal Chemistry,* 1987, 30(10), 1798-806) (3.33 g, 18.5 mmol) was dissolved in dry benzene (40 mL). NBS (3.45 g, 19.4 mmol) and benzoyl peroxide (134 mg, 0.55 mmol) were added. The solution was stirred in a 75° C. oil bath for about 2 hours. After cooling down, the solid was filtered and washed with $Et_2O$ (150 mL). The organic solution was then washed with water (50 mL) twice, dried over $Na_2SO_4$ or $MgSO_4$, filtered, and concentrated by rotary evaporator. The crude product was dried under vacuum to give compound 3B which was used without further purification. $^1$H-NMR appeared to indicate that approximately 75% of this material was compound 3B.

Step 2

Compound 3B (4.62 mmol), Compound 3C (824 mg, 4.62 mmol), and $K_2CO_3$ (1.28 g, 9.24 mmol) were mixed in DMF (30 mL). The solution was stirred at room temperature for 20 hours. DMF (15 mL) was added and the solid was filtered and washed with DMF. All the DMF solution was combined and concentrated to 25 mL. The resulting solution was purified via reverse phase MPLC($CH_3CN$/water, 5% to 90%, containing 0.1% $HCO_2H$) to give compound 3D (198 mg, 15%).

Example 4

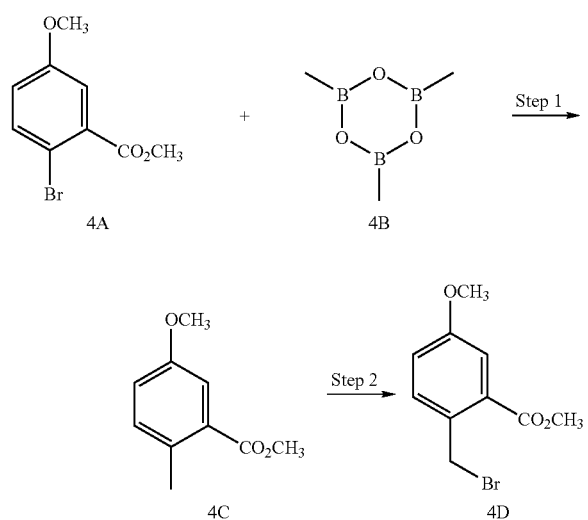

Step 1

Compound 4A (20 g, 81.61 mmol), 4B (13.36 mL, 97.93 mmol), Pd(dppf)Cl$_2$ (1.0 g, 1.36 mmol), dioxane (350 mL), water (50 mL), and Cs$_2$CO$_3$ (22.5 g, 163 mmol) were stirred at 110° C. (oil bath) under nitrogen for 16 hours. After cooling, the solid was removed by filtration. The solution was concentrated and purified by sgc (Hexane/EtOAc, 10:1) to give 4C (12.1 g, 80%).

Step 2

Compound 4C was converted to Compound 4D using a procedure similar to that described in Example 3.

Example 5

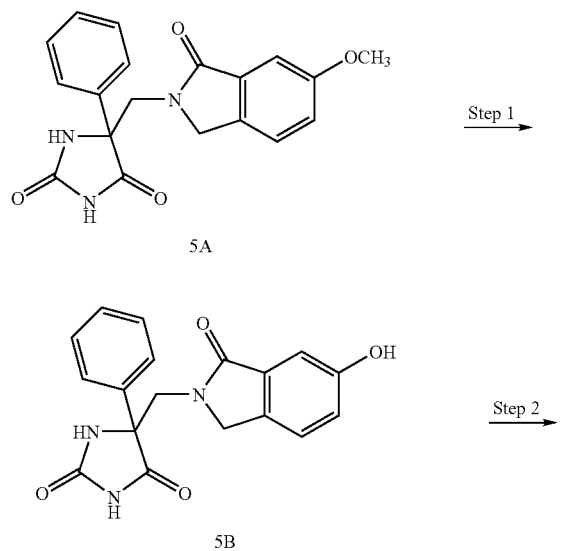

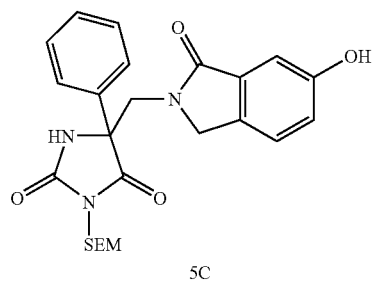

Compound 5A was prepared using chemistry similar to that described in Examples 1, 2, 3 and 4.

Step 1

Compound 5A (1.18 g, 3.36 mmol) and pyridine hydrochloride (2.33 g, 20.17 mmol) were added into a 20 mL microwave reactor tube and reacted at 200° C. for 1 hour. After cooling down, the solid was dissolved in DMF and purified by reverse phase chromatography on a C-18 cartridge (CH$_3$CN/water 5% to 90%, with 0.1% HCO$_2$H) to give compound 5B (0.87 g, 77%).

Step 2

Compound 5B (0.75 g, 2.22 mmol) was dissolved in DMF (12 mL). SEMCl (0.48 mL, 2.44 mmol) and DIPEA (0.775 mL, 4.44 mmol) were added and the solution was stirred at 25° C. for 4 hours. DMF was removed under vacuum and the product was purified by sgc (Hexane/EtOAc: 3:1 to 1:1) to give compound 5C (0.81 g, 78%).

Example 6

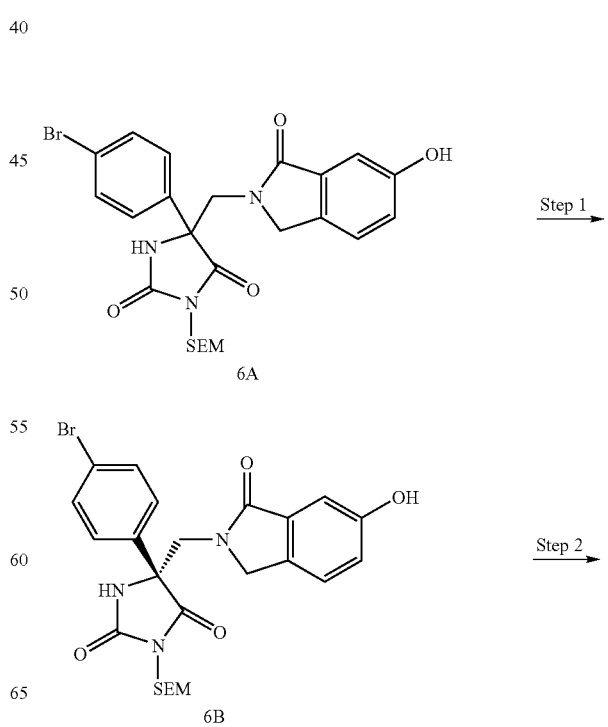

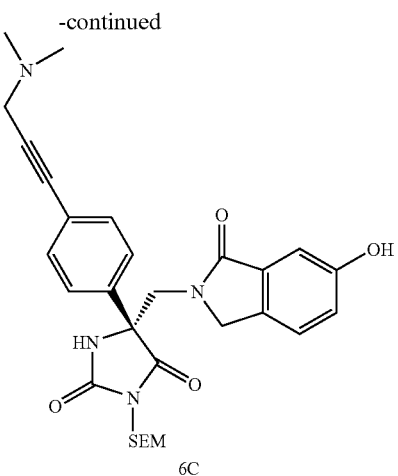

6C

↓ Step 3

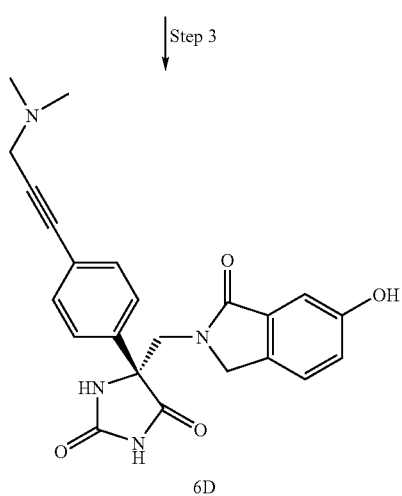

6D

Compound 6A was prepared using chemistry similar to that described in Examples 1, 2, 3 4, and 5.

Step 1

Compound 6A was resolved by Chiralcel OD column (Mobile phase: Hexane:2-propanol 4:1). The first peak was collected and concentrated to give compound 6B.

Step 2

Compound 6B (0.2 g, 0.36 mmol), allyl palladium chloride dimer (3 mg, 0.008 mmol), and DMF (3 mL) were added to a round bottomed flask and cycled between vacuum and nitrogen three times. Tri-tert-butyl phosphine (30 microliters of 10% solution in hexanes-Strem), piperidine (61 mg, 0.7 mmol), and 3-dimethylamino-1-propyne were added via syringe. The reaction was left stirring overnight at rt. The following morning, the reaction was stirred for 1 hr at 50° C. The resulting material was diluted with EtOAc, washed with water, dried with $MgSO_4$, and concentrated to dryness. The crude product was purified via flash silica gel chromatography using a gradient elution of 70% (5% Methanol in EtOAC) in hexanes to 100% (5% Methanol in EtOAc) giving 55 mg of compound 6C.

Step 3

Compound 6C (55 mg) was dissolved in 10 mL of 4 M HCl in dioxane (Aldrich) and 10 ml of methanol and the solution was added to a pressure tube. The tube was capped and heated to 90° C. The reaction mixture was stirred at 90° C. for 4 hr, then allowed to cool to room temperature. The reaction mixture was concentrated to dryness. Methanol was added and the reaction mixture was reconcentrated to dryness. Methanol (5 ml) and triethylamine (1 mL) were added and the reaction mixture was stirred at rt for 2 hr. The resulting solution was concentrated to dryness. The crude product was purified on a C-18 Isco cartridge using an (acetonitrile:water (+0.1% formic acid)) gradient as the mobile phase to give 6D.

Chemistry similar to the procedures described in Examples 6, 8, 1, 2, 3, 4, and 5 was used to prepare compounds 18, 19, 20, 21, and 22 in Table 1.

Example 7

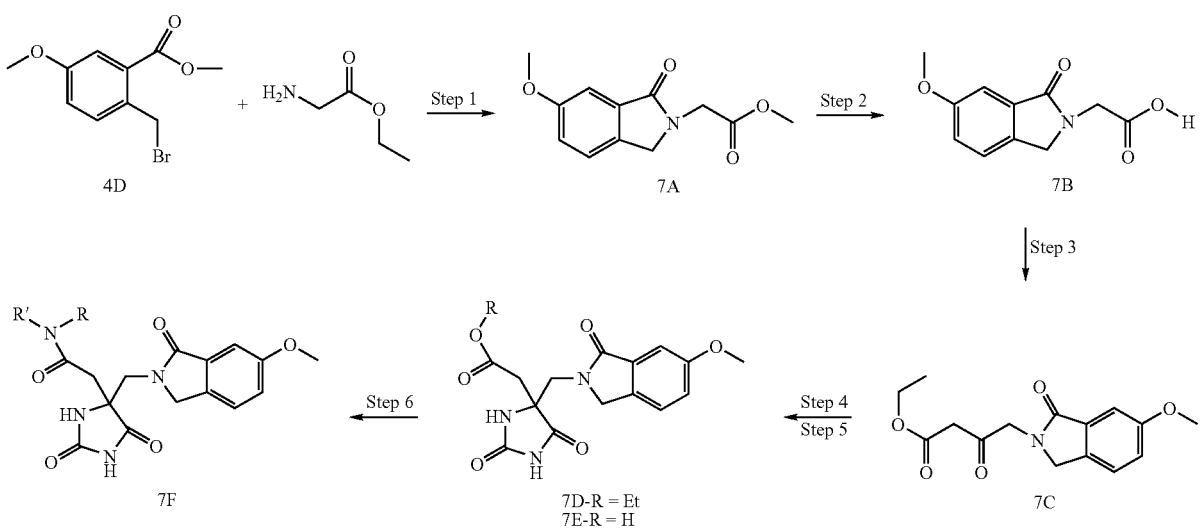

Step 1

Compound 4D (16.26 g, 62.77 mmol) was dissolved in 100 mL of DMF and glycine ethyl ester hydrochloride (9.68 g, 69.35 mmol) was added. Diisopropylethylamine (21 mL, 15.6 mmol) was added and the reaction mixture was placed in a 70° C. oil bath. The reaction mixture was stirred overnight at 70° C. After 17 hr, the reaction mixture was allowed to cool to rt. EtOAc, water, and 5 mL of 1M aq $NaHSO_4$ were added and the layers were separated. The organic layer was washed with water and brine, dried with $MgSO_4$, filtered and concentrated to an orange oil (14.8 g). The crude product was purified via flash silica gel chromatography using a 20% to 60% EtOAc:Hexanes gradient as the mobile phase to give 6.8 g of 7A as product.

Step 2

Compound 7A (6.31 g, 25.3 mmol) was dissolved in dioxane (88 mL). A 1.0 M aq soln of LiOH (28 mL, 28 mmol) was added followed by 10 mL of absolute ethanol. The reaction mixture was stirred at rt for 3 hr, then partially concentrated on the rotary evaporator. Dichloromethane and 1M aq $NaHSO_4$ were added and the layers were separated. The aq layer was extracted with $CH_2Cl_2$. The combined organic layer was filtered, dried with $MgSO_4$, filtered again, and concentrated to dryness giving 4.04 g of 7B.

Step 3

Compound 7B (2.02 g, 9.13 mmol) was suspended in 15 mL of THF. Carbonyl diimidazole was added in one portion. After 10 min, acetonitrile (10 mL) was also added. The reaction mixture was stirred at rt for 1 hr. Magnesium chloride and ethyl potassium malonate were added. The reaction mixture was left stirring overnight at room temperature under a drying tube. The reaction mixture was concentrated to near dryness. EtOAc and 1.0 M pH 5.5 sodium phosphate buffer were added. The layers were separated. The organic layer was washed with water and brine, dried with $MgSO_4$, filtered, and concentrated to dryness. An off white solid was obtained. The crude product was purified via silica gel chromatography using a 50% to 100% EtOAc: Hexanes gradient as the mobile phase to give 1.87 g of 7C.

Step 4

Compound 7C was dissolved in 18 mL of absolute ethanol and 8 mL of water. The solution was added to a thick walled glass pressure bottle and ammonium carbonate (2.21 g, 23.0 mmol) was added. The bottle was capped and the reaction mixture was stirred at rt for 15 min. Potassium cyanide was added, the bottle was recapped, and the reaction mixture was stirred at 70° C. for 16 hr. The resulting mixture was poured into 250 mL of water and suction filtered to give 7D (1.86 g) as a white solid.

Step 5

Compound 7D (0.83 g, 2.29 mmol) was suspended in 9 mL of dioxane. Aq 1.0 M LiOH (4.6 mL, 4.6 mmol) was added, causing the material to dissolve. The reaction mixture was stirred at rt for 5.5 hr. Additional LiOH was added (1.0 mL. 1.0 mmol) and the reaction mixture was stirred for 1 hr. The reaction mixture was concentrated to near dryness. The resulting mixture was acidified with aq 1 M $NaHSO_4$ causing a precipitate to form. The flask was placed in an ice water bath and stirred for 30 min. The resulting mixture was suction filtered to give 7E (0.70 g) as a white solid.

Step 6

Compound 7E (31 mg, 0.093 mmol) was dissolved in DMF (400 μL). Carbonyl diimidazole (18 mg, 0.11 mmole) was added and the reaction mixture was stirred at rt for 30 min. Pyrrolidine (20 μL) was added and the reaction mixture was stirred at rt for 5 hr. Aq 1 M $NaHSO_4$ was added (7 mL) followed by EtOAc. The layers were separated. The organic layer was dried with $MgSO_4$, filtered, and concentrated to dryness. the crude product was purified via reverse phase (C-18 Isco cartridge) chromatography using a 10% to 60% acetonitrile:water+(0.1% formic acid) gradient as the mobile phase. A white solid was obtained as product giving compound 5 in Table 1, which is one embodiment of the class of compounds 7F.

The procedures described in Example 7 were used to prepare compounds 1 through 17 in Table 1.

Example 8

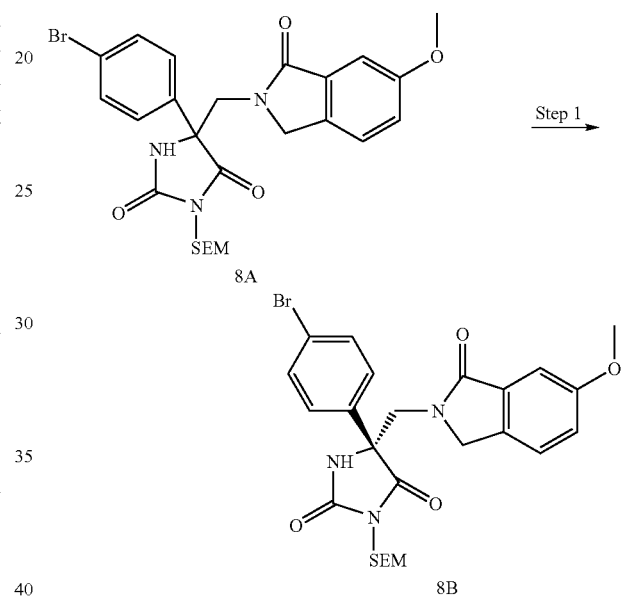

Compound 8A was prepared using chemistry similar to that described in Examples 1, 2, 3, 4 and 5.

Step 1

Compound 8A was resolved by Chiralcel OD column (Mobile phase: Hexane:2-propanol 4:1). The first peak was collected and concentrated to give compound 8B.

Example 9

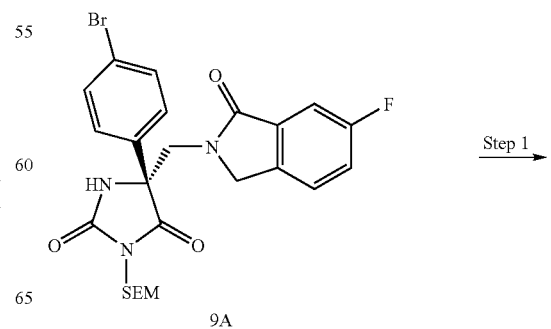

-continued

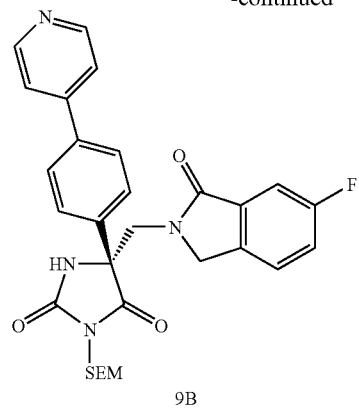
9B

Chemistry similar to that described in Examples 8 and 9 was used to prepare compound 24 in Table 1.

Example 10

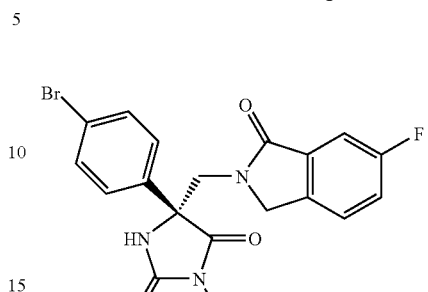
9A

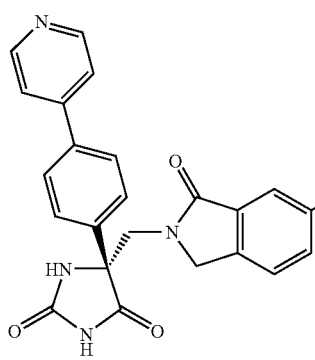
9C

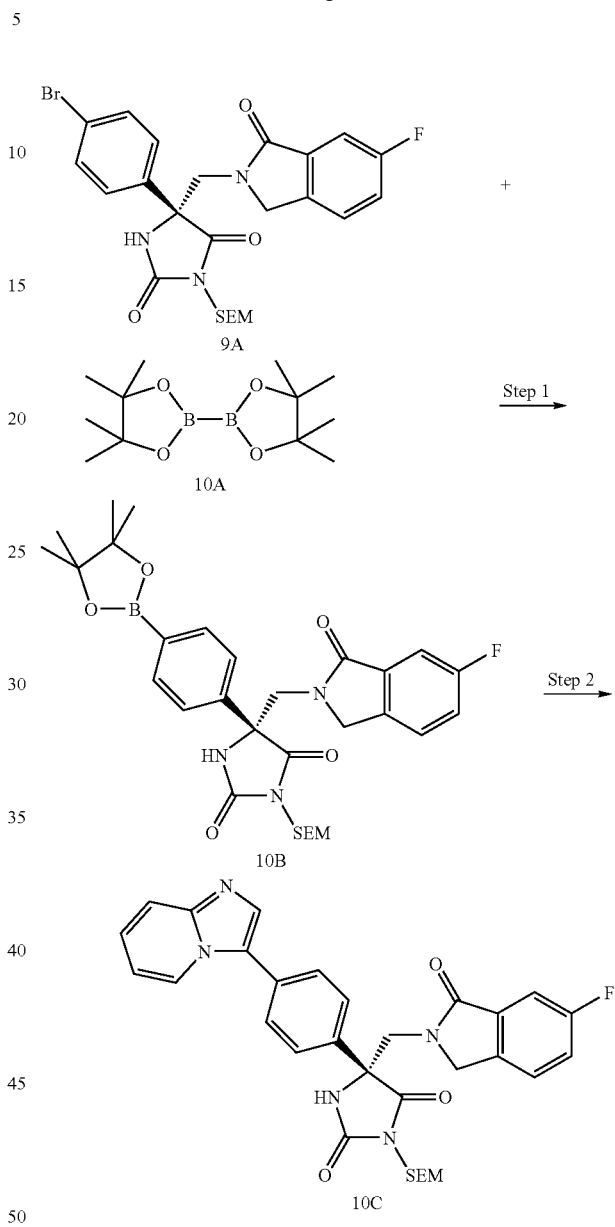

Racemic compound 9A was prepared using chemistry similar to that described in Examples 1, 2, 3, 4 and 5. The enantiomers were resolved by Chiralcel OD column (Mobile phase: Hexane/2-propanol 3:1). The first peak was collected and concentrated to give compound 9A in its enantiomerically pure form.

Step 1

To a dry flask was added compound 9A (1.5 g, 2.73 mmol) and 4-pyridyl boronic acid (670 mg, 5.50 mmol). The flask was subjected to vacuum and refilled with nitrogen three times. Pd(dppf)Cl$_2$ (220 mg, 0.30 mmol) was added and followed by addition of CH$_3$CN (20 mL) and aq. K$_2$CO$_3$ (1 M, 15 mL). The solution was stirred at 80° C. (oil bath) for 16 hours. After cooling down, CH$_3$CN (100 mL) was added and the solid was removed by filtration. The aqueous layer was separated and extracted with EtOAc (20 mL) once. The organic solution was combined and concentrated. The product was purified by SGC(CH$_2$Cl$_2$/MeOH/NH$_4$OH: 20:1:0.1) to give compound 9B.

Step 2

Compound 9B was dissolved in a mixture of methanol and HCl (4M in dioxane) (2:1, 30 mL) and was stirred overnight in a sealed pressure flask at 90° C. (oil bath). After the solution was cooled, the solution was transferred into a 250 mL round bottom flask. It was concentrated and dried under vacuum. The crude mixture was dissolved in methanol (50 mL) and Et$_3$N (0.5 mL) was added and stirred overnight at 25° C. The solvent was then removed and the product was purified by C18 reverse phase chromatography (CH$_3$CN/water 5% to 90%, with addition of 0.1% HCO$_2$H) to give compound 9C (815 mg).

Step 1

A mixture of compound 9A (0.3 g, 0.55 mmol), bis(pinacolato)diboron (10A; 170 mg, 0.65 mmol), potassium acetate (170 mg, 1.70 mmol), and [PdCl$_2$(dppf)]CH$_2$Cl$_2$ (50 mg, 0.05 mmol) in 1,4-dioxane (10 mL) was cycled between vacuum and argon three times. The reaction mixture was stirred at 100° C. (oil bath) for 1.5 hours. After cooling down, the mixture was diluted in EtOAc (50 mL) and filtered through a Celite pad. The filtrate was concentrated in vacuo and the residual material was purified by silica gel column chromatography (2% MeOH in CH$_2$Cl$_2$) to afford compound 10B (300 mg, 91% yield).

Step 2

A solution of compound 10B (60 mg, 0.10 mmol), 3-bromoimidazo[1,2-a]pyridine (30 mg, 0.15 mmol), and [PdCl$_2$ (dppf)]CH$_2$Cl$_2$ (8.2 mg, 0.01 mmol) in CH$_3$CN (3 mL) was treated with potassium carbonate (0.6 mL, 0.6 mmol, 1M in H$_2$O). The mixture was subjected to vacuum and refilled with argon three times. The reaction mixture was stirred at 90° C. (oil bath) for 17 hours. After cooling, the mixture was diluted in EtOAc (20 mL) and filtered through a Celite pad. The filtrate was concentrated in vacuo and the residual material was purified by preparative TLC (10% MeOH in CH$_2$Cl$_2$) to afford compound 10° C. (42 mg, 71% yield).

Example 11

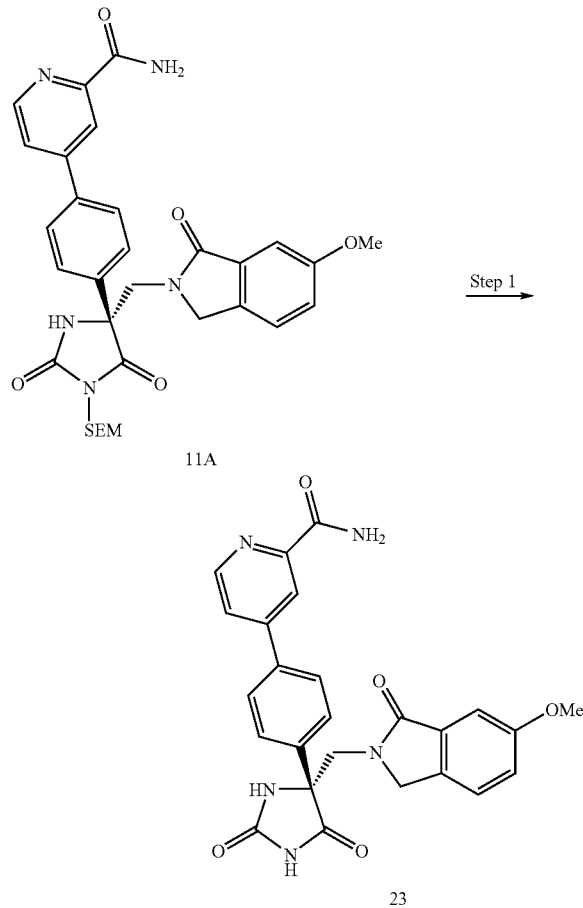

Compound 11A was prepared via procedure similar to those described in Examples 8 and 10.

Step 1

Compounds 11A (53 mg) was dissolved in 2 mL methanol in a 15 mL pressure tube. HCl (4M in dioxane, 1 mL) was added. The tube was sealed and put into an 80° C. oil bath for 16 h. After cooling down, the solution was transferred into a 100 mL flask and the solvent was removed. NH$_3$ (7N in methanol, 3 mL) was added and the solution was transferred into a 15 mL pressure tube. The tube was sealed and put into a 70° C. oil bath for three hours. After cooling down, the solution was transferred into 100 mL flask and the solvent was removed. The product was purified by C18 reverse phase chromatography (CH$_3$CN/water, 5% to 90%, with 0.1% HCO$_2$H) to give compound 23. Compound 23 was dissolved in methanol, and HCl (4M in dioxane, 0.5 mL) was added. The solution was stirred at 25° C. for 30 minutes. The solvent was removed and the product was suspended in water. The water was removed by lyophilizer to give compound 23 (22 mg) in Table 1.

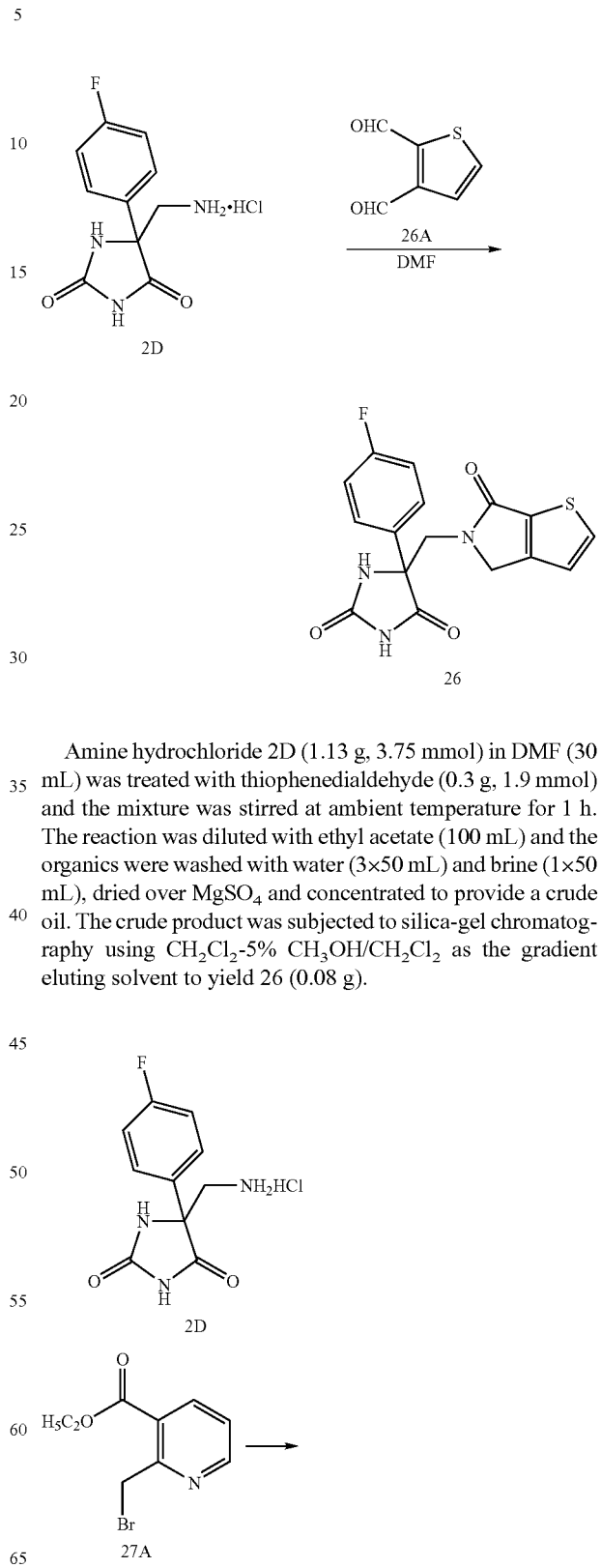

Amine hydrochloride 2D (1.13 g, 3.75 mmol) in DMF (30 mL) was treated with thiophenedialdehyde (0.3 g, 1.9 mmol) and the mixture was stirred at ambient temperature for 1 h. The reaction was diluted with ethyl acetate (100 mL) and the organics were washed with water (3×50 mL) and brine (1×50 mL), dried over MgSO$_4$ and concentrated to provide a crude oil. The crude product was subjected to silica-gel chromatography using CH$_2$Cl$_2$-5% CH$_3$OH/CH$_2$Cl$_2$ as the gradient eluting solvent to yield 26 (0.08 g).

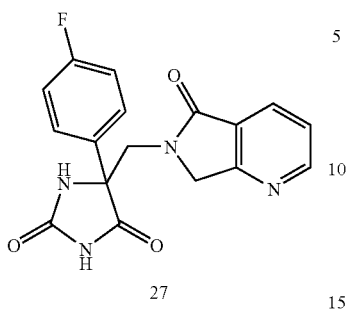

27

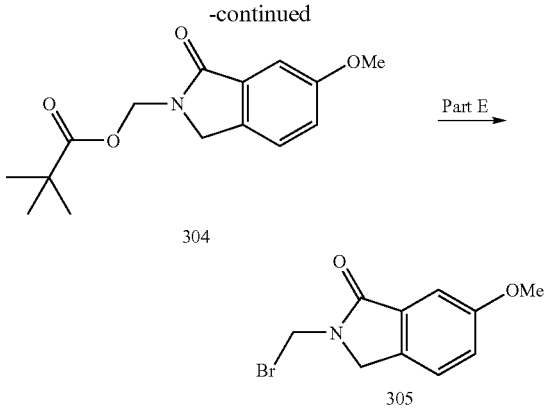

Amine hydrochloride 2D (2.7 g, 8 mmol) in DMF (30 mL) was treated with bromoethylester 27A (3.6 g, 15 mmol) and diisopropylethylamine (2.6 mL). The mixture was heated to 55° C. and stirred for 24 h. The reaction was diluted with ethyl acetate (200 mL) and the organics were washed with water (3×50 mL) and brine (1×50 mL), dried over MgSO$_4$ and concentrated to provide crude solid. The product 27 (1.8 g) was isolated by recrystallization (ethyl acetate: ether; 2:1). The product 27A was prepared from commercially available (Aldrich) ethyl nicitinate using the process described in step 1 example 3.

Compound #25 (Table 1) was prepared analogously using appropriate starting materials.

Example 300A

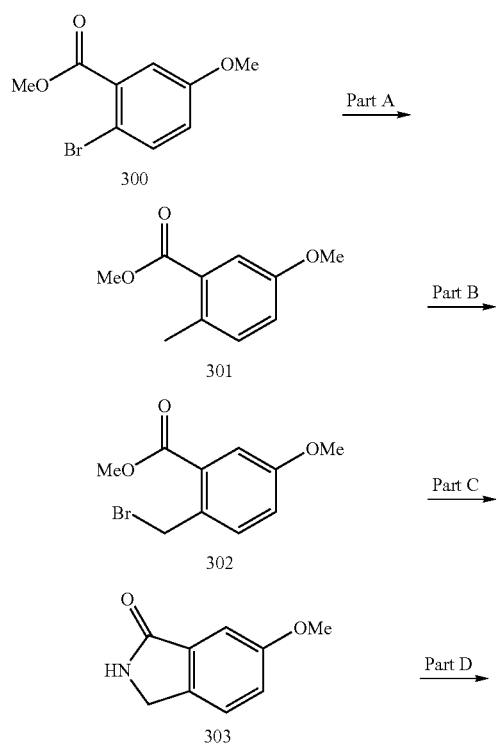

Part A:

Compound 300 (20.0 g, 81.61 mmol), trimethylboroxine (13.36 mL, 97.93 mmol), Pd(dppf)Cl$_2$ (1.0 g, 1.36 mmol), dioxane (350 mL), water (50 mL), and cesium carbonate (22.5 g, 163 mmol) were stirred at 110° C. (oil bath) under nitrogen for 16 hours. After cooling, the solid was removed by filtration. The solution was concentrated and purified by sgc (10:1 EtOAc/hexanes) to give 301 (12.1 g, 80%).

Part B:

Compound 301 (4.4 g, 24.2 mmol) was dissolved in carbon tetrachloride (80 mL) and N-bromosuccinimide (4.48 g, 24.2 mmol) and benzoyl peroxide (276 mg, 1.13 mmol) were added. The reaction mixture was stirred at reflux for 3 hours and then solids were filtered and washed with ether. The combined organic layers were washed with water, dried over sodium sulfate, and concentrated to provide the desired product 302 (6.1 g, 98%).

Part C:

Compound 302 (32.0 g, 124.0 mmol) was dissolved in 7 M ammonia in MeOH (150 mL) and stirred in a sealed pressure flask at 60° C. overnight. The reaction mixture was cooled and the solvent was removed under reduced pressure. The residue was suspended in ethyl acetate and stirred for 30 minutes. The solids were filtered and dissolved in methylene chloride. The methylene chloride was washed with water, dried over sodium sulfate, and concentrated to provide the desired product 303 (13.5 g, 67%).

Part D:

Compound 303 (2.2 g, 13.4 mmol) was dissolved in THF (250 mL) and DMPU (40 mL). Sodium t-butoxide (1.55 g, 16.13 mmol) was added and stirred for 5 hours. Chloromethylpivalate (3.0 mL, 20.1 mmol) was added dropwise and stirred overnight. The reaction was quenched with saturated ammonium chloride and extracted with ethyl acetate. The combined ethyl acetate layers were washed with water, brine, dried over sodium sulfate and concentrated. Purification by column chromatography (SiO$_2$, 25% ethyl acetate/hexanes) afforded the desired product 304 (2.5 g, 67%).

Part E:

Compound 304 (288 mg, 1.04 mmol) was dissolved in methylene chloride (5 mL) and cooled in an ice bath. Bromotrimethylsilane (0.3 mL, 2.08 mmol) was added dropwise and stirred in the ice bath for 30 minutes followed by 2 hours at room temperature. The reaction mixture was concentrated and re-dissolved in methylene chloride (2 mL). Hexanes (8 mL) was added and the solids were filtered to provide the desired product 305 (218 mg, 83%).

Example 400

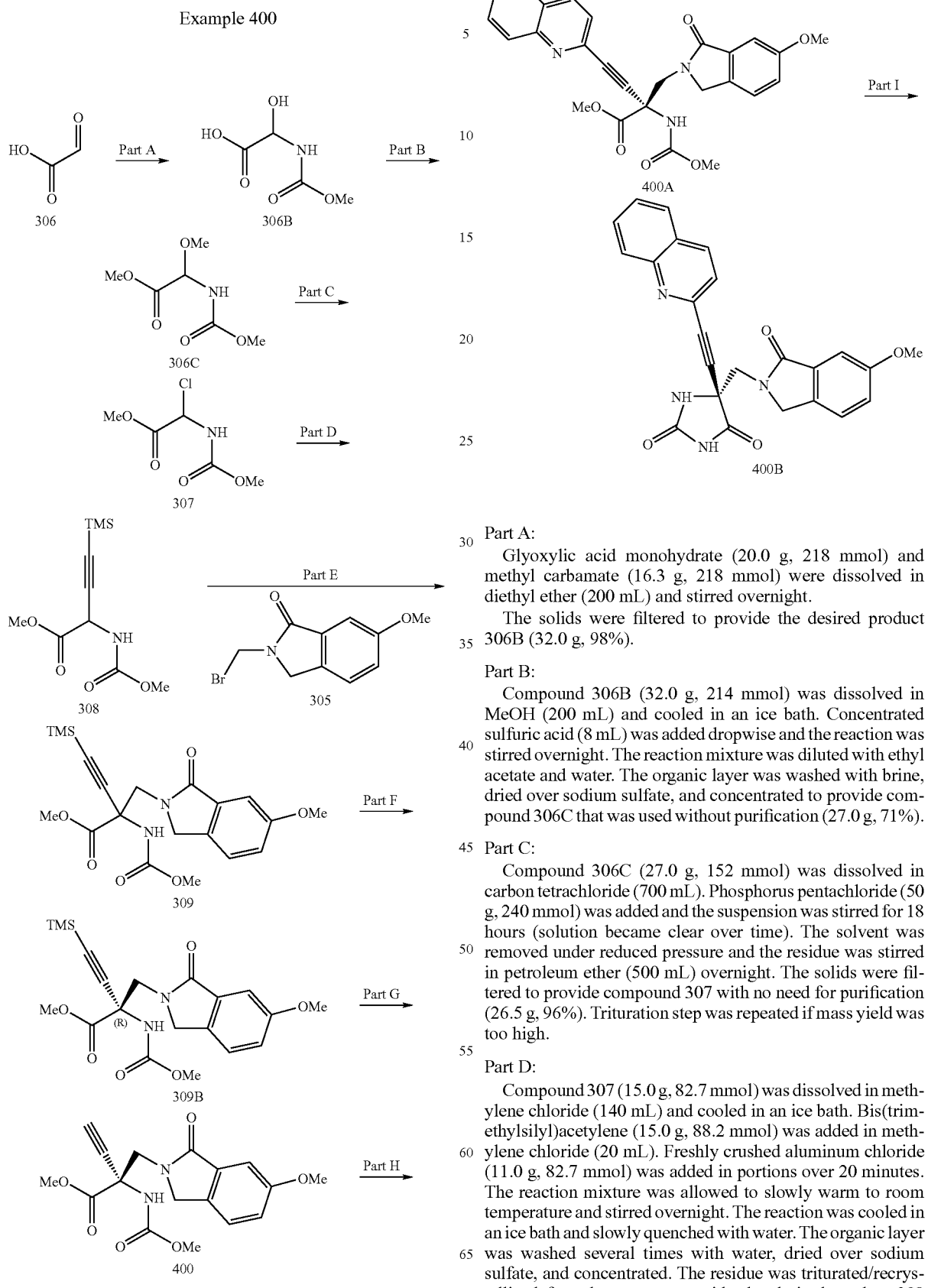

Part A:

Glyoxylic acid monohydrate (20.0 g, 218 mmol) and methyl carbamate (16.3 g, 218 mmol) were dissolved in diethyl ether (200 mL) and stirred overnight.

The solids were filtered to provide the desired product 306B (32.0 g, 98%).

Part B:

Compound 306B (32.0 g, 214 mmol) was dissolved in MeOH (200 mL) and cooled in an ice bath. Concentrated sulfuric acid (8 mL) was added dropwise and the reaction was stirred overnight. The reaction mixture was diluted with ethyl acetate and water. The organic layer was washed with brine, dried over sodium sulfate, and concentrated to provide compound 306C that was used without purification (27.0 g, 71%).

Part C:

Compound 306C (27.0 g, 152 mmol) was dissolved in carbon tetrachloride (700 mL). Phosphorus pentachloride (50 g, 240 mmol) was added and the suspension was stirred for 18 hours (solution became clear over time). The solvent was removed under reduced pressure and the residue was stirred in petroleum ether (500 mL) overnight. The solids were filtered to provide compound 307 with no need for purification (26.5 g, 96%). Trituration step was repeated if mass yield was too high.

Part D:

Compound 307 (15.0 g, 82.7 mmol) was dissolved in methylene chloride (140 mL) and cooled in an ice bath. Bis(trimethylsilyl)acetylene (15.0 g, 88.2 mmol) was added in methylene chloride (20 mL). Freshly crushed aluminum chloride (11.0 g, 82.7 mmol) was added in portions over 20 minutes. The reaction mixture was allowed to slowly warm to room temperature and stirred overnight. The reaction was cooled in an ice bath and slowly quenched with water. The organic layer was washed several times with water, dried over sodium sulfate, and concentrated. The residue was triturated/recrystallized from hexanes to provide the desired product 308

(14.8 g, 69%). HPLC-MS $t_R$=1.84 min (ELSD); mass calculated for formula $C_{10}H_{17}NO_4Si$ 243.09, observed LCMS m/z 244.1 (M+H).

Part E:

Compound 308 (24.0 g, 98.7 mmol) and compound 305 (25.1 g, 99.0 mmol) were dissolved in THF (300 mL) and cooled to −78° C. A 1M solution of LiHMDS (198 mL, 198 mmol) was added dropwise over 30 minutes and the reaction mixture was stirred for 2 hours. Saturated ammonium chloride solution was added slowly and the reaction was allowed to warm to room temperature. The aqueous layer was extracted with ethyl acetate. The combined organic layers were washed with water, brine, dried over sodium sulfate, and concentrated. Purification by column chromatography (SiO$_2$, 33% ethyl acetate/hexanes to 50% ethyl acetate/hexanes) afforded the desired product 309 (26.0 g, 63%). HPLC-MS $t_R$=1.90 min (UV$_{254\ nm}$); mass calculated for formula $C_{20}H_{26}N_2O_6Si$ 418.15, observed LCMS m/z 419.2 (M+H).

Part F:

The two isomers were separated using a chiral OD column. One gram of material was injected into the column and the two peaks were separated by using a solvent mixture of 85% hexanes/ethanol. The second isomer was the desired compound 309B (400 mg, 80%).

Part G:

Compound 309B (8.0 g, 19.1 mmol) was dissolved in THF (250 mL) and cooled to 0° C. Tetrabutylammonium fluoride (1 M in THF, 22.9 mL, 22.9 mmol) was added dropwise and the reaction was stirred for 1 hour at room temperature. The reaction mixture was diluted with ethyl acetate and water. The organic layer was washed with water, saturated sodium bicarbonate, brine, dried over sodium sulfate and concentrated to provide compound 400 (5.8 g, 88%). The product was used without purification.

Part H:

Compound 400 (75 mg, 0.22 mmol) was combined with 3-bromoquinoline (0.032 mL, 0.24 mmol), Pd(PPh$_3$)$_2$Cl$_2$ (3 mg, 0.0044 mmol), CuI (2 mg, 0.009 mmol), diisopropylamine (0.062 mL, 0.44 mmol) in DMF (1 mL) and stirred overnight at 80° C. The reaction mixture was diluted with ethyl acetate and water. The organic layer was washed with water, brine, dried over sodium sulfate and concentrated. Purification by column chromatography (SiO$_2$, 50% ethyl acetate/hexane to 80% ethyl acetate/hexane) afforded the desired product 400A (93 mg, 89%). HPLC-MS $t_R$=1.66 min (UV$_{254\ nm}$); mass calculated for formula $C_{26}H_{23}N_3O_6$ 473.16, observed LCMS m/z 474.1 (M+H).

Part I:

Compound 400A (77 mg, 0.16 mmol) was dissolved in 7 M ammonia solution (3 mL) and stirred in a sealed pressure tube at 90° C. overnight. The reaction mixture was cooled to room temperature and concentrated to afford compound 400B. HPLC-MS $t_R$=1.41 min (UV$_{254\ nm}$); mass calculated for formula $C_{24}H_{18}N_4O_4$ 426.13, observed LCMS m/z 427.0 (M+H).

Example 300E

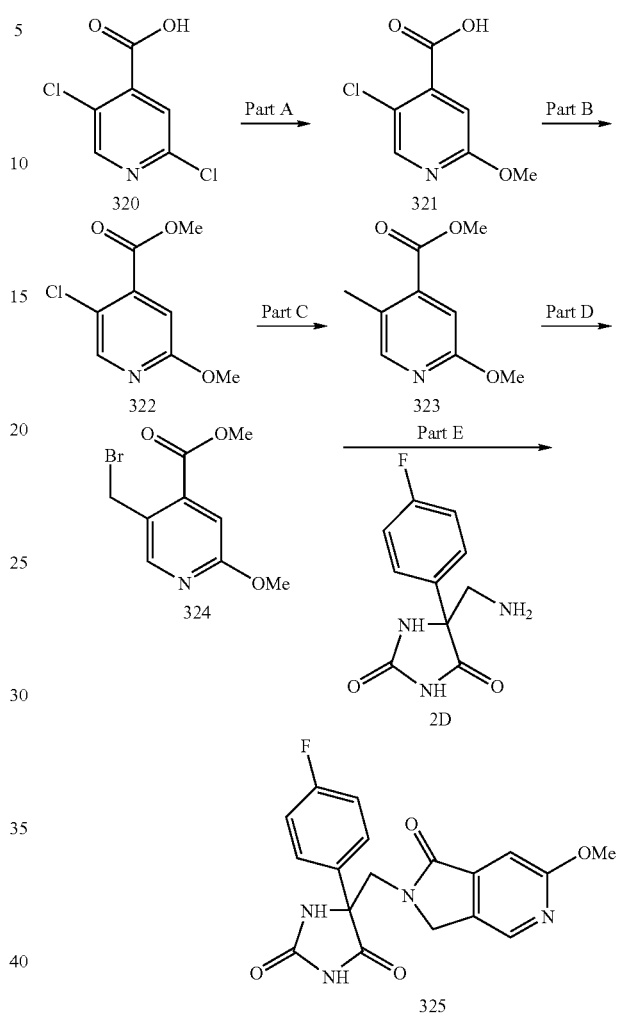

Part A:

Sodium pellets (3.6 g, 156 mmol) were dissolved in MeOH (100 mL) at 0° C. Compound 320 (3.0 g, 15.6 mmol) was added and stirred at 100° C. in a sealed pressure flask overnight. The reaction was cooled to room temperature and diluted with ethyl acetate and 1 N HCl. The organic layer was dried over sodium sulfate and concentrated to provide the desired product 321 with no need for purification (2.1 g, 72%).

Part B:

Compound 321 (2.1 g, 11.1 mmol) was dissolved in toluene (30 mL) and methanol (30 ml) and cooled in an ice bath. TMS diazomethane (2M in hexanes, 11 mL) was added dropwise until yellow color persisted. The solvent was evaporated under reduced pressure to provide the desired product 322 with no need for purification (2.2 g, quant.).

Part C:

Compound 322 (1.0 g, 5.0 mmol) was combined with Pd(P-tBu$_3$)$_2$ (128 mg, 0.25 mmol), Pd(dba)$_3$ (250 mg, 0.25 mmol), trimethylboroxine (1.0 mL, 6.5 mmol), potassium phosphate monohydrate (3.69 g, 15 mmol) in dioxane (25 mL) and stirred at 90° C. overnight. The reaction mixture was filtered and the solvent was evaporated under reduced pressure. Purification by column chromatography (SiO$_2$, 10% ethyl acetate/hexanes) afforded the desired product 323 (0.500 g, 55%).

Part D:

Compound 323 (210 mg, 1.16 mmol) was dissolved in carbon tetrachloride (6 mL) and N-bromosuccinimide (228 mg, 1.28 mmol) and benzoyl peroxide (10 mg) were added. The reaction mixture was stirred at reflux overnight, cooled to room temperature, and filtered (solids were washed with ether). The combined organic layers was washed with water, dried over sodium sulfate, and concentrated to provide the desired product 324 (0.20 g, 67%).

Part E:

Compound 324 (75 mg, 0.29 mmol) and compound 2D (75 mg, 0.29 mmol) were dissolved in DMF (5 mL) and DIEA (0.15 mL, 0.87 mmol) and stirred at 70° C. overnight. The reaction mixture was diluted with ethyl acetate and water. The organic layer was washed with water, brine, dried over sodium sulfate, and concentrated. The residue was purified by reverse phase chromatography to provide the desired product 325 (24.1 mg, 22%). HPLC-MS $t_R$=1.269 min (UV$_{254\ nm}$); mass calculated for formula $C_{18}H_{15}N_4O_4F$ 370.10, observed LCMS m/z 371.1 (M+H).

Example 300F

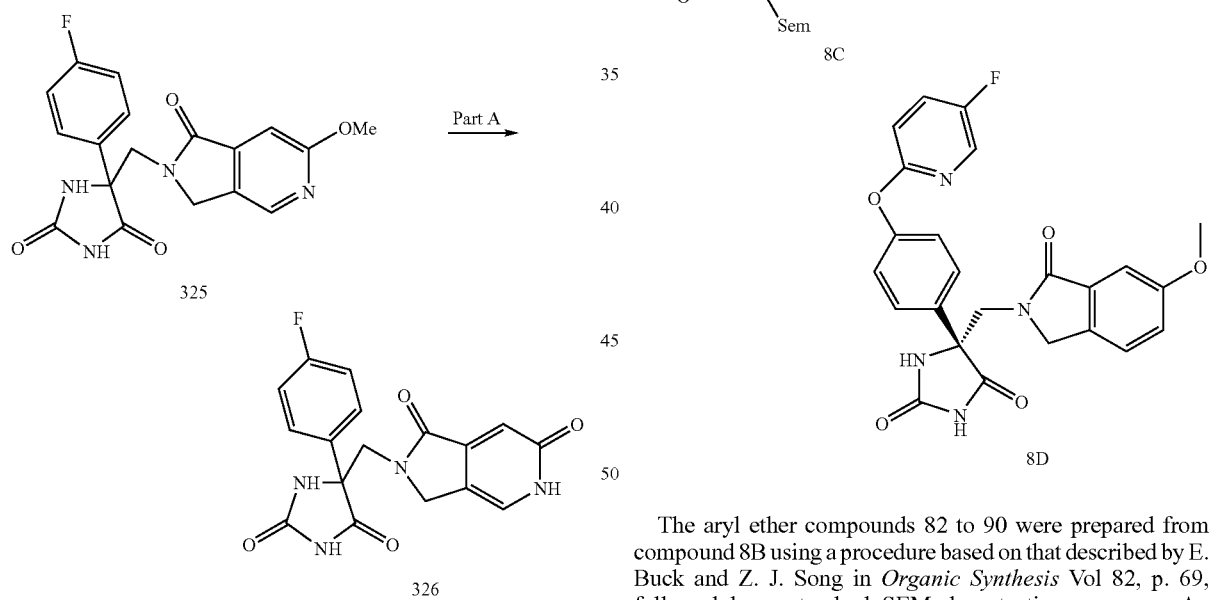

Part A:

Compound 325 (140 mg, 0.378 mmol), chlorotrimethylsilane (226 mg, 1.89 mmol), and sodium iodide (283 mg, 1.89 mmol) were dissolved in acetonitrile (5 mL) and stirred at reflux for 10 minutes. Water (0.3 mL) was added and the reaction was refluxed for 3 hours. The reaction mixture was cooled and diluted with ethyl acetate and water. The organic layer was dried over sodium sulfate and concentrated. Purification by reverse phase chromatography provided the desired product 326 (7.1 mg, 5%). HPLC-MS $t_R$=0.855 min (UV$_{254\ nm}$); mass calculated for formula $C_{17}H_{13}N_4O_4F$ 356.09, observed LCMS m/z 357.1 (M+H).

Example 82

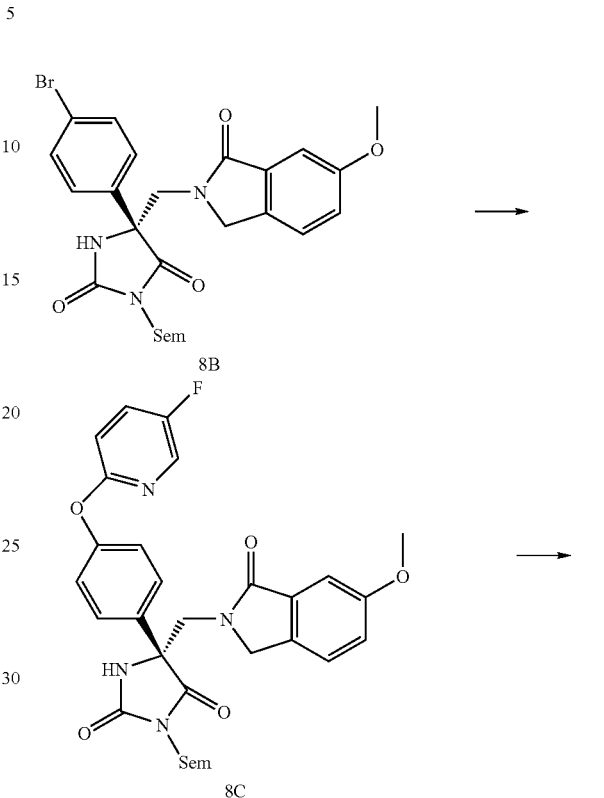

The aryl ether compounds 82 to 90 were prepared from compound 8B using a procedure based on that described by E. Buck and Z. J. Song in *Organic Synthesis* Vol 82, p. 69, followed by a standard SEM deprotection sequence. An example is provided below.

Compound 8B (0.248 g, 0.442 mmol), 5-Fluoro-2-hydroxypyridine (128 mg, 1.13 mmol), cesium carbonate (374 mg, 1.14 mmol), and copper (I) chloride (48 mg, 0.48 mmol) were added to a 10 mL Schlenck tube equipped with a stir bar. The tube was capped with a septum and cycled between vacuum and N$_2$ three times. N-methyl-2-pyrrolidinone (2 mL) was added via syringe and the Schlenck tube was cycled between vacuum and N$_2$ three times. 2,2,6,6-Tetramethyl heptane-3,5-dione (33 μL) was added via syringe. The Schlenck tube was placed in a 100° C. oil bath and heated to 150° C. The reaction mixture was stirred for 23 h at 150° C.

The reaction mixture was allowed to cool to rt, then diluted with EtOAc and water. Aqueous 1% EDTA was added and the layers were separated. The organic layer was washed with 1% aq EDTA, water, and brine. The resulting organic solution was dried with MgSO$_4$, filtered, and concentrated to dryness. A brown solid was obtained. The crude product was purified via sgc using a Biotage SiO$_2$ cartridge and a 1%-2.5% MeOH/CH$_2$Cl$_2$ gradient as the mobile phase. The major spot was collected as product, giving 0.04 g of compound 8C.

Compound 8C (0.04 g) was dissolved in (10 mL) anhydrous acetonitrile and concentrated to dryness on the rotovap. This step was repeated. The compound was redissolved in anhydrous acetonitrile (3 mL) and placed under N$_2$. The flask was cooled in an ice water bath. BF$_3$ etherate (90 μL) was added, the ice bath was removed, and the reaction mixture was stirred at rt for 7 h. The reaction mixture was capped and stored in a 4° C. freezer overnight. The reaction mixture was cooled in an ice-water bath. Diisopropylethylamine (1.5 mL) was added, followed by aq 3.0 M sodium hydroxide. The reaction was stirred for 15 min. The ice bath was removed, and the reaction mixture was stirred for 3 h at rt. Acetic acid was added until the reaction mixture was weakly acidic. The reaction mixture was partially concentrated on the rotovap. EtOAc and water were added. The layers were separated. The organic layer was washed with water and brine, dried with MgSO$_4$, filtered, and concentrated to dryness. The crude product was purified via reverse phase chromatography using an Isco C-18 cartridge (43 g). The mobile phase was a 15% to 80% CH$_3$CN/H$_2$O gradient with 0.1% (volume) formic acid added to both components of the mobile phase. The main peak was isolated as product giving compound 8D.

Example 93A

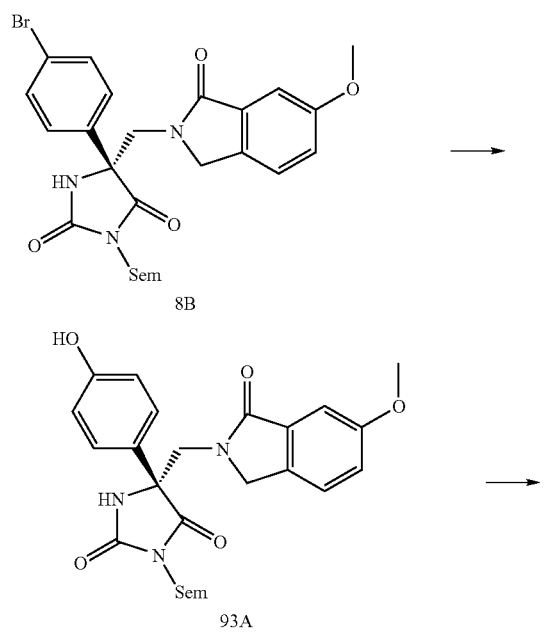

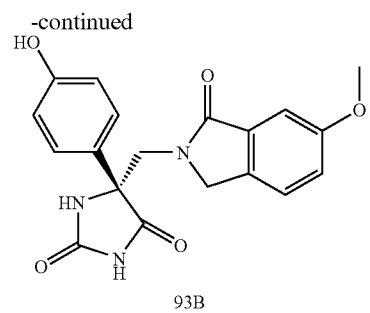

Compound 8B (1.50 g, 2.68 mmol), pinocolatodiboron (816 mg, 3.21 mmol), potassium acetate (785 mg, 8.0 mmol), and palladium (II) dichloride(dppf) CH$_2$Cl$_2$ complex (250 mg, 0.306 mmol) were added to a 100 mL Schlenck flask equipped with a stir bar. The flask was caped with a septum, then cycled between vacuum and nitrogen four times. Dioxane (20 mL, Aldrich anhydrous) was added via syringe. The flask was cycled between vacuum and nitrogen three times, then placed in an 85° C. oil bath. The bath was heated to 100° C., then stirred for 1.5 h. the reaction mixture was allowed to cool to RT and diluted with EtOAc (80 mL). The resulting mixture was filtered through Celite. The Celite was rinsed with additional EtOAc. The combined filtrate was concentrated to near dryness then redissolved in EtOAc. The organic solution was washed with 1.0 M aq pH 7 sodium phosphate buffer, water, and brine. After drying with MgSO$_4$, the organic layer was concentrated to dryness. The crude product was purified via sgc using a 2%-4% MeOH/CH$_2$Cl$_2$ gradient as the mobile phase. A brown solid was obtained (1.9 g). The solid was dissolved in dioxane (16 mL) and water (11 mL) was added. Sodium perborate (3.0 g, 19.5 mmol) was added and the reaction mixture was stirred at rt overnight. The reaction mixture was diluted with EtOAc and aq 1 M NH$_4$Cl. The layers were separated. The organic layer was washed with water and brine, dried with MgSO$_4$, filtered and concentrated to dryness, giving an off white solid (1.37 g). SGC using a gradient of 25% to 100% (5% Methanol in EtOAc)/Hexanes as the mobile phase gave 0.25 g of pure 93A and 0.62 g of impure 93A.

Compound 93A (0.70 g, 1.40 mmol) was dissolved in 50 mL of Aldrich 4N HCl in dioxane and 50 mL of methanol. The solution was added to a pressure tube equipped with a stir bar. The tube was capped, placed in an oil bath, and heated to 95 C. The reaction was stirred at 95° C. for 4 h, then allowed to cool to rt. The reaction mixture was concentrated to dryness. Methanol was added and the reaction mixture was reconcentrated. Methanol (50 mL) was added, followed by triethylamine (5 mL). The reaction mixture was stirred at rt for 1 h, then concentrated to dryness. EtOAc and 1.0 M aq pH 5.5 sodium phosphate buffer were added. The layers were separated. The organic layer was washed with water and brine, dried with MgSO$_4$, filtered, and concentrated to dryness. The crude product was purified via SiO$_2$ chromatography. The mobile phase was a gradient of 10% to 100% of (100:10:1-CH$_2$Cl$_2$:MeOH:concentrated NH$_4$OH) in CH$_2$Cl$_2$. The main UV active peak was isolated as product giving 0.42 g of compound 93B as white solid.

Example 93

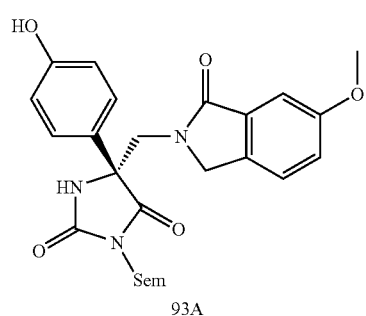

93A

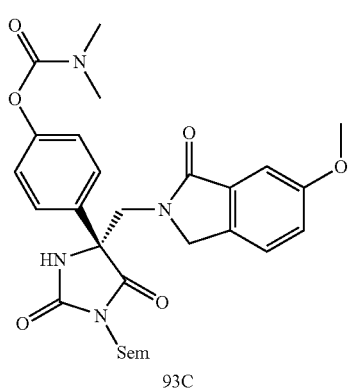

93C

Compound 93A (0.05 g, 0.10 mmol) was dissolved in CH$_2$Cl$_2$ (5 mL). N,N-Dimethylcarbamyl chloride (18 µL) and DMAP (8 mg) were added and the reaction mixture was stirred at rt overnight. The reaction mixture was diluted with CH$_2$Cl$_2$ and washed with 1.0 M aqueous pH 7.0 sodium phosphate buffer, water, and brine. The organic layer was dried with MgSO$_4$, filtered, and concentrated to dryness. The crude product was purified via sgc using a 0.5% to 5% MeOH/CH$_2$Cl$_2$ gradient on a 40 g Isco SiO$_2$ Cartridge. The major UV active peak was isolated as compound 93C.

Compound 93C was converted to compound 93 using SEM deprotection procedures similar to those described previously.

Example 401

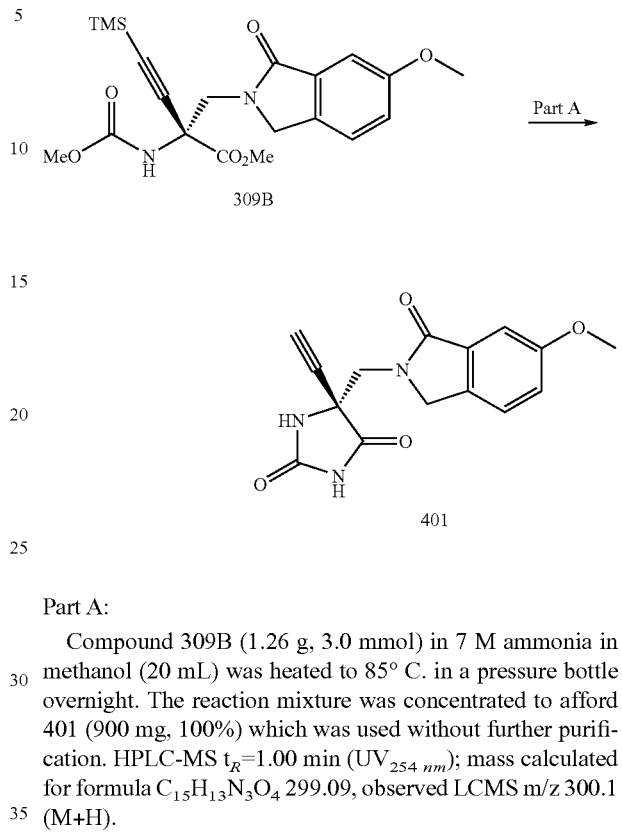

Part A:

Compound 309B (1.26 g, 3.0 mmol) in 7 M ammonia in methanol (20 mL) was heated to 85° C. in a pressure bottle overnight. The reaction mixture was concentrated to afford 401 (900 mg, 100%) which was used without further purification. HPLC-MS t$_R$=1.00 min (UV$_{254\,nm}$); mass calculated for formula C$_{15}$H$_{13}$N$_3$O$_4$ 299.09, observed LCMS m/z 300.1 (M+H).

Example 45

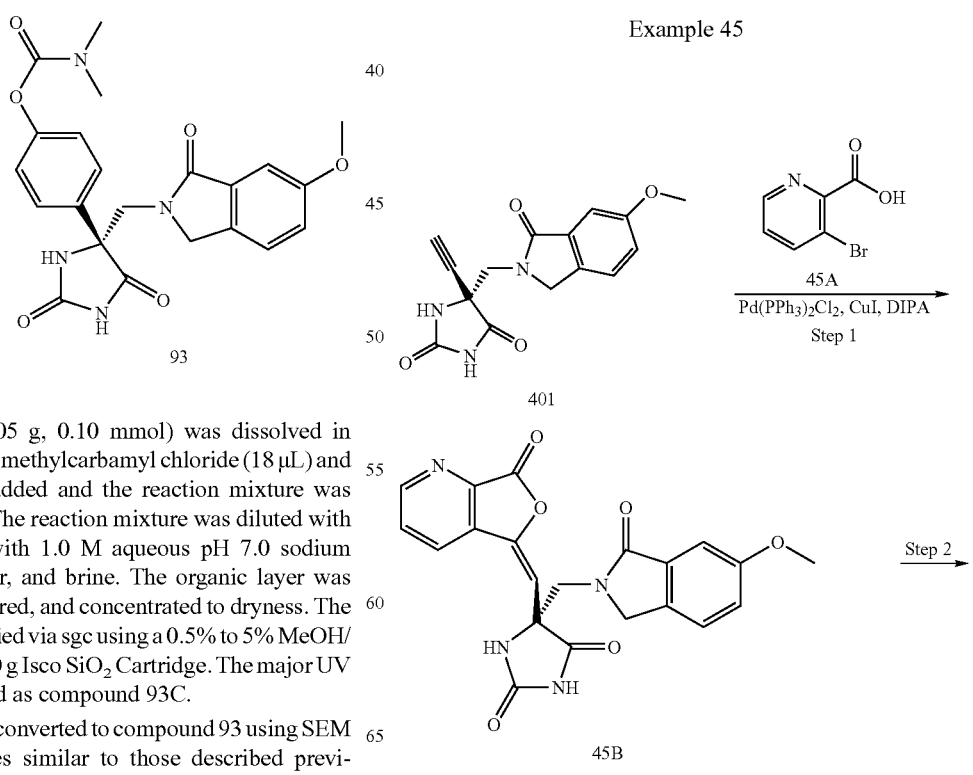

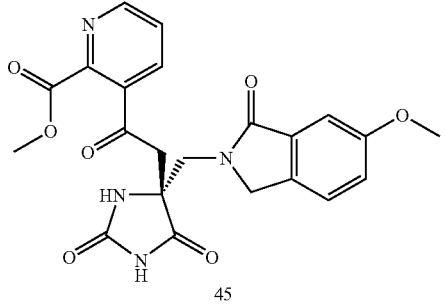

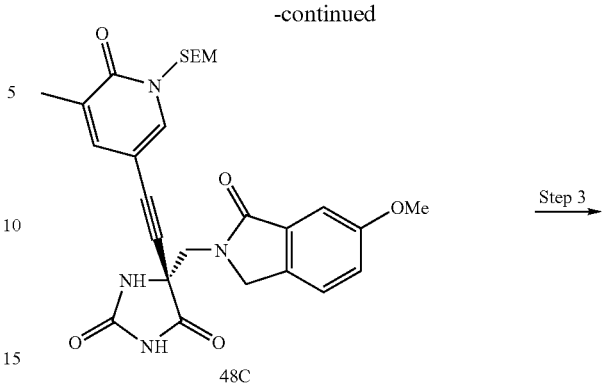

Step 1. Compound 401(100 mg, 0.33 mmol) was combined with compound 45A (80 mg, 0.4 mmol), Pd(PPh$_3$)$_2$Cl$_2$ (8 mg, 0.012 mmol), CuI (17 mg, 0.1 mmol), disopropylamine (0.08 mL, 0.58 mmol) in DMF (1 mL) and stirred at 85° C. for 2 h. The reaction mixture was purified on a Gilson reverse phase HPLC (0-40% acetonitrile in H$_2$O with formic acid 0.1%) afforded the desired product 45B(18 mg, 13%).

Step 2. Compound 45B (20 mg, 0.23 mmol) was stirred in MeOH (5 mL) and HCl (1N, aq., cat.). The reaction was stirred at rt for 2 h. Solvent was removed and the crude material was purified on a Gilson reverse phase HPLC (0-50% acetonitrile in H$_2$O with 0.1% formic acid) afforded the desired product 45 (20 mg, 99%).

Example 48

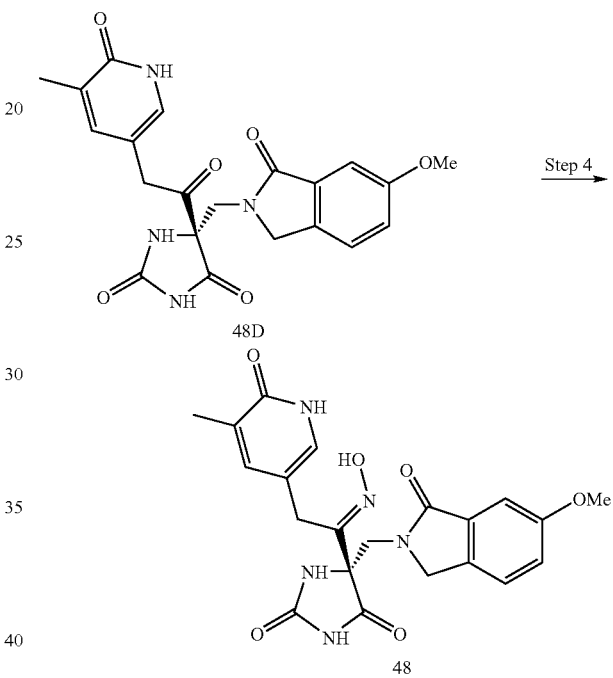

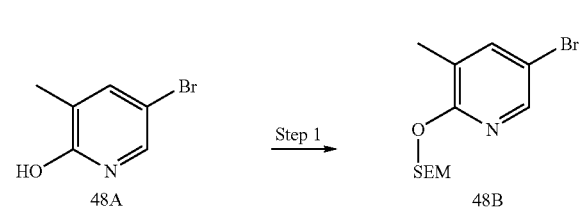

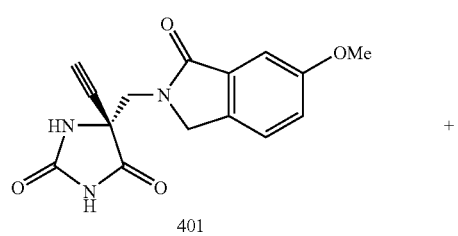

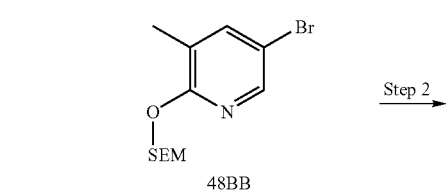

Step 1
A mixture of 48A (161 mg, 0.86 mmol), SEMCI (0.17 mL, 0.94 mmol), and diisopropylethylamine (0.22 mL, 1.28 mmol) in CH$_2$Cl$_2$ (3 mL) was stirred at 25° C. for 2 h. The mixture was added to an aqueous NaHCO$_3$ solution and the organic layers were extracted with CH$_2$Cl$_2$. The combined organic solution was washed with brine solution, dried (Na$_2$SO$_4$), and concentrated in vacuo. The residue was purified by SiO$_2$ column chromatography (CH$_2$Cl$_2$/hexane=2:1). to afford 48B (200 mg, 74% yield).

Step 2
A mixture of 401 (100 mg, 0.33 mmol), 48B (165 mg, 0.52 mmol), Pd(PPh$_3$)$_2$Cl$_2$ (4.9 mg, 70 mol), CuI (1.9 mg, 100 mol), and diisopropylethylamine (0.17 mL, 0.99 mmol) in DMF (1.5 ml) was purged with N$_2$ and heated to 70° C. After heating for 17 h, the mixture was cooled to 25° C. and purified by column chromatography on a reverse phase C-18 column (0.01% HCO$_2$H in water/0.01% HCO$_2$H in CH$_3$CN) to afford 48C (78 mg, 44% yield).

Step 3
48C (78 mg, 0.14 mmol) was dissolved in MeOH (15 mL) and treated with 4 N HCl in dioxane (3 mL). The mixture was heated to 60° C. in a pressure vessel for 16 h and cooled to 25° C. The mixture was neutralized with NH₃-MeOH (7 N solution) and the resulting precipitate was filtered off. The filtrate was concentrated in vacuo and the residue was purified by preparative TLC (10% MeOH in CH₂Cl₂) to afford 48D (25 mg, 40% yield).

Step 4

To a solution of 48D (12 mg, 0.028 mmol) in EtOH (4 mL) were added NH₂OH HCl salt (10 mg, 0.14 mmol) and pyridine (34 mL, 0.42 mmol) at 25° C. The mixture was heated to reflux for 16 h and concentrated in vacuo. The residue was purified by preparative TLC (10% MeOH in CH₂Cl₂) to afford 48 (5 mg, 42% yield).

Example 47

Compound 47A was prepared using Example 400.

Example 41

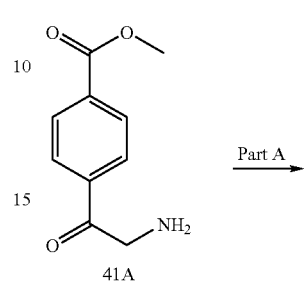

Compound 47A (20 mg) was dissolved in absolute ethanol (10 mL). Lindlar catalyst was added (18 mg) and the reaction mixture was placed under balloon pressure of hydrogen gas. The reaction mixture was left stirring overnight at rt. The reaction mixture was concentrated to dryness. CH₂Cl₂ was added and the resulting material was loaded onto a 19 SiO₂ Sep-Pak.

The product was eluted with 95:5 CH₂Cl₂: MeOH. The filtrate was concentrated to give 457 as a clear oil.

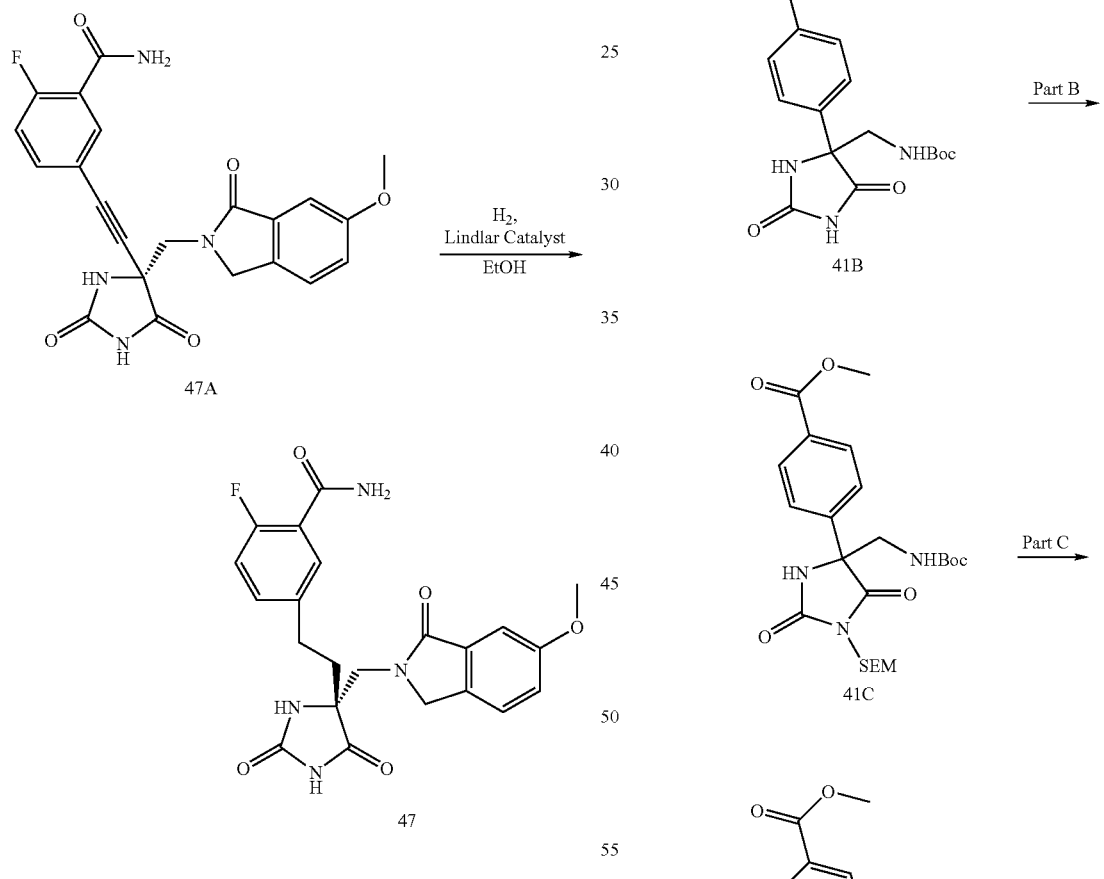

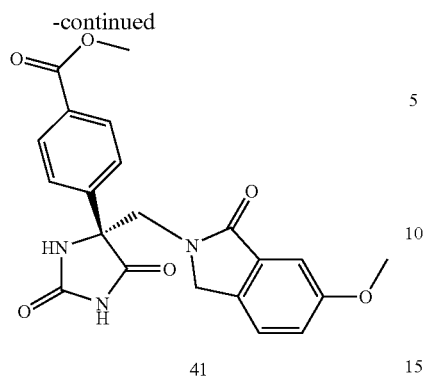

41

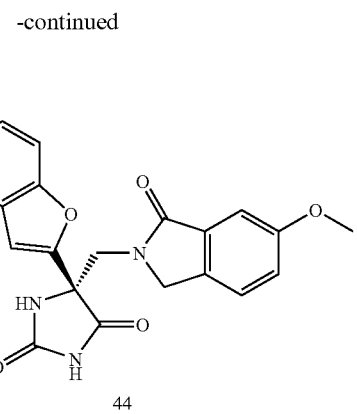

44

Part A:

Compound 41B was prepared from compound 41A according to the procedures described in Example 300D part A and B.

Part B:

To a mixture of 41b (7.87 g, 21.7 mmol) and diisopropylethylamine (7.5 mL, 43.4 mmol) in DMF (80 mL) was added 2-trimethylsilylethoxy methyl chloride (4.7 mL, 23.8 mmol). The mixture was stirred at room temperature overnight, diluted with water and extracted with ethyl acetate. The combined organic layers were washed with water, brine, dried over sodium sulfate and concentrated. The residue was purified by column chromatography (SiO$_2$, 15% EtOAc/hexane to 30% EtOAc/hexane) to afford 41C as a white solid (10.2 g, 95%). HPLC-MS $t_R$=2.17 min (UV$_{254\ nm}$); mass calculated for formula C$_{23}$H$_{35}$N$_3$O$_7$Si 493.2, observed LCMS m/z 516.1 (M+Na).

Part C:

The two isomers of 41C were separated using a chiral AD column. One gram of material was injected into the column and the two peaks were separated by using a solvent mixture of 80% hexanes/2-propanol. The second isomer was the desired compound 41 D (400 mg, 80%).

Part D:

Compound 41 was prepared from 41 D following the procedures described in Example 2 step 3, Example 300E part C and Example 8. HPLC-MS $t_R$=1.32 min (UV$_{254\ nm}$); mass calculated for formula C$_{21}$H$_{19}$N$_3$O$_6$ 409.13, observed LCMS m/z 410.2 (M+H).

Example 44

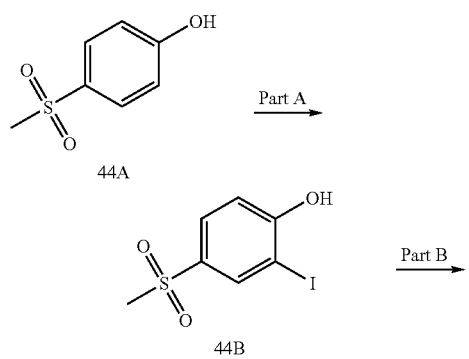

Part A:

Compound 44A (670 mg, 3.91 mmol) and iodine (2.10 g, 8.0 mmol) were dissolved in THF (20 mL) and 1 M sodium carbonate (20 mL) and stirred for 4 hours. The reaction was diluted with ethyl acetate and water. The organic layer was dried over sodium sulfate and concentrated (1.05 g mixture of unseparable mono and di-iodinated products). The residue was combined with methyl iodide (1.5 mL) and cesium carbonate (5 g) in DMF (20 mL) and stirred at 60° C. for 3 hours. The reaction was diluted with water and ethyl acetate. The organic layer was dried over sodium sulfate and concentrated.

Column chromatography (2:1 hexanes/ethyl acetate) provided the mono-iodinated methyl ether (460 mg). The methyl ether was dissolved in methylene chloride (7 mL) and 1 M boron tribromide (7 mL) and stirred at room temperature for 5 hours. The reaction was quenched slowly with water and extracted with ethyl acetate. The organic layer was dried over sodium sulfate and concentrated to provide the desired product (390 mg, 34%). $^1$H NMR (400 MHz, CDCl$_3$) δ 8.25 (d, 1H), 7.85-7.8 (m, 1H), 7.1 (d, 1H), 3.0 (s, 3H).

Part B:

Compound 401 (130 mg, 0.43 mmol), compound 44B (130 mg, 0.43 mmol), Pd(PPh$_3$)$_2$Cl$_2$ (15 mg), CuI (8 mg), and triethylamine (0.4 mL) were dissolved in DMF (3 mL) and stirred at 80° C. under an inert atmosphere. The solvent was evaporated and the residue was purified by reverse phase chromatography to provide the desired product (112.3 mg, 55%). HPLC-MS $t_R$=1.2 min (UV$_{254\ nm}$); mass calculated for formula C22H19N3O7S 469.47, observed LCMS m/z 470.0 (M+H). $^1$H NMR (400 MHz, DMSO-d$_6$) δ 11.2 (s, 1H), 9.0 (s, 1H), 8.3 (m, 2H), 7.9 (s, 1H), 7.5 (d, 1H), 7.35 (s, 1H), 7.2-7.1 (m, 2H), 4.5-4.3 (m, 4H). 3.8 (s, 3H), 3.2 (s, 3H).

Example 46

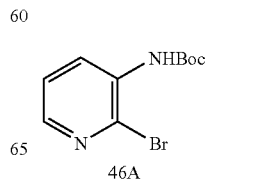

46A

+

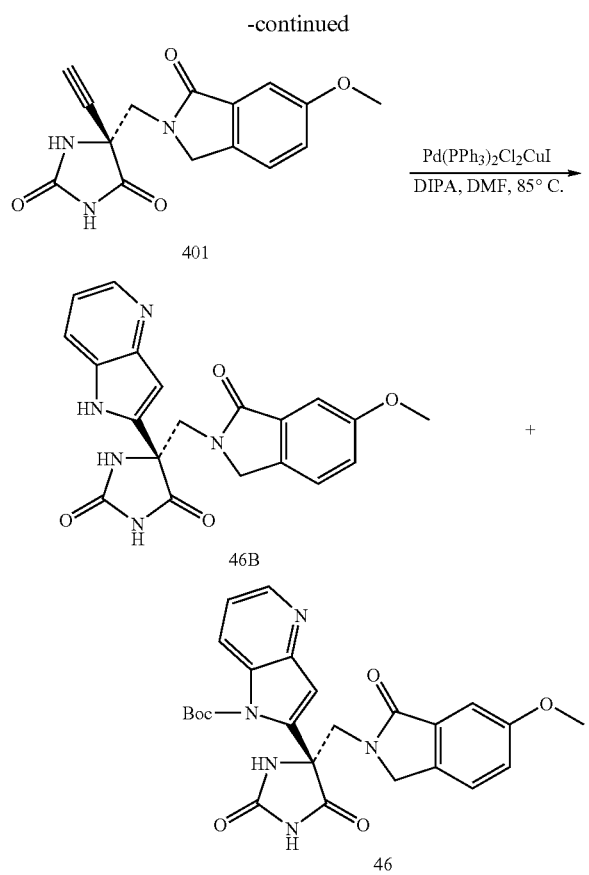

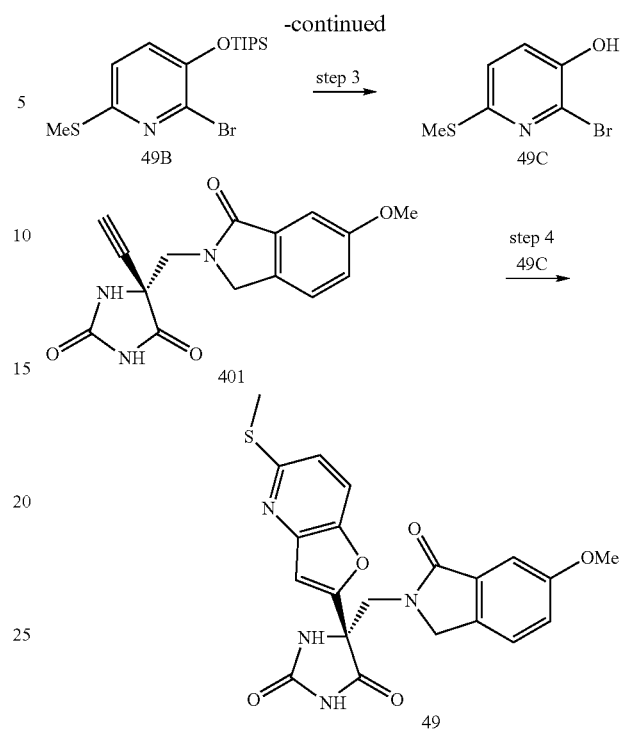

Step 1

Compound 46A (80 mg, 0.29 mmol) was combined with compound 401 (100 mg, 0.33 mmol), Pd(PPh$_3$)$_2$Cl$_2$ (5 mg, 0.007 mmol), CuI (12 mg, 0.06 mmol), diisopropylamine (0.16 mL, 1.13 mmol) in DMF (1 mL) and stirred at 85° C. The reaction mixture was neutralized with acetic acid and purified with Gilson reverse phase (0-40% acetonitrile in H$_2$O with 0.1% formic acid) afforded the desired product 46B (3 mg, 3%) mass calculated for formula C$_{20}$H$_{17}$N$_5$O$_4$ 391.13, observed LCMS m/z 392.2. (M+H) and compound 46 (22 mg, 15%), mass calculated for formula C$_{25}$H$_{25}$N$_5$O$_6$ 491.18, observed LCMS m/z 492.2.

(M+H)

Example 49

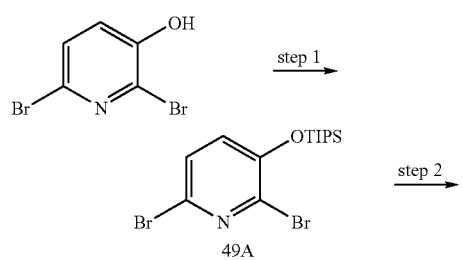

Step 1

The commercially available 2,6-dibromo-3-hydroxypyridine (588 mg, 2.32 mmol) was dissolved in THF (6 mL) and the solution was treated with triethylamine (0.49 mL, 3.48 mmol) and triisopropylsilyl triflate (0.75 mL, 2.78 mmol) at 0° C. The mixture was stirred at the temperature for 10 min then added to an aqueous NaHCO$_3$ solution. The organic layers were extracted by CH$_2$Cl$_2$ and the combined organic solution was washed with brine solution, dried (Na$_2$SO$_4$), and concentrated in vacuo to afford a crude 49A (1.11 g, quantitative) which was used without further purification.

Step 2

A solution of 49A (100 mg, 0.24 mmol) in toluene (1 mL) was treated with t-BuLi (1.7 M in pentane, 0.32 mL, 0.54 mmol) at −78° C. After stirring for 0.5 h at the temperature, methyl disulfide (65 µL, 0.72 mmol) was added to the mixture slowly and the resulting mixture was stirred for 4.5 h at −78° C. to 25° C. The mixture was quenched by MeOH (0.3 mL) and diluted in CH$_2$Cl$_2$ followed by filtration through SiO$_2$ pad. The clear filtrate was concentrated in vacuo to afford a mixture of 49B and its bromide regioisomer (~1:1, 62 mg) which was used without further purification.

Step 3

A mixture of 49B and its regioisomer (62 mg, ~0.16 mmol) was dissolved in THF and solution was treated with TBAF (1 M in THF, 0.24 mL, 0.24 mmol) at 0° C. The mixture was stirred at the temperature for 1 h and poured to a cold mixture of EtOAc and water. The organic layers were extracted by EtOAc and the combined organic solution was washed with brine solution, dried (Na$_2$SO$_4$), and concentrated in vacuo to afford a crude mixture of 49C and its bromide regioisomer (~1:1, 41 mg) which was used without further purification.

Step 4

A mixture of 401 (150 mg, 0.50 mmol), 49C (~50% purity, 460 mg, ~1 mmol), Pd(PPh$_3$)$_2$Cl$_2$ (7 mg, 10 µmol), CuI (1.9 mg, 10 μmol), and diisopropylethylamine (0.43 mL, 2.5 mmol) in DMF (3 ml) was purged with N₂ and heated to 60° C. After heating for 18 h, the mixture was cooled to 25° C. and purified by column chromatography on a reverse phase C-18 column (0.01% HCO₂H in water/0.01% HCO₂H in CH₃CN) to afford a crude 49 which was further purified by preparative TLC (5% MeOH in CH₂Cl₂) to afford pure 49 (27 mg, 12% yield).

Example 50

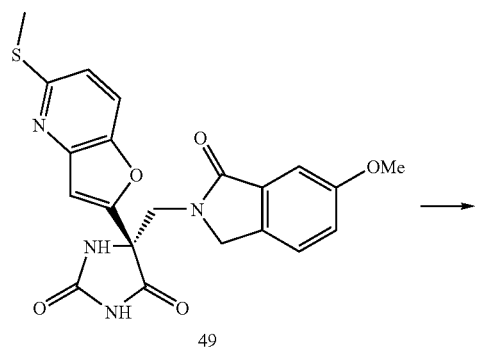

49

-continued

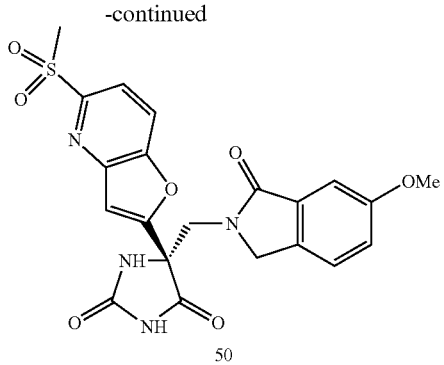

50

A solution of 49 (27 mg, 0.06 mmol) in CH₂Cl₂ (3 mL) was treated with 3-chloroperbenzoic acid (ca 70% purity, 30 mg, 0.12 mmol) at 0° C. The mixture was stirred at 25° C. for 1.5 h. The suspension was dissolved in 10% MeOH—CH₂Cl₂ and treated with ion exchange resin (Amberlyst, A-21, weakly basic) followed by filtration. The filtrate was concentrated in vacuo and the residue was purified by preparative TLC (10% MeOH in CH₂Cl₂) to afford 50 as a white solid (18 mg, 61% yield).

Example 32

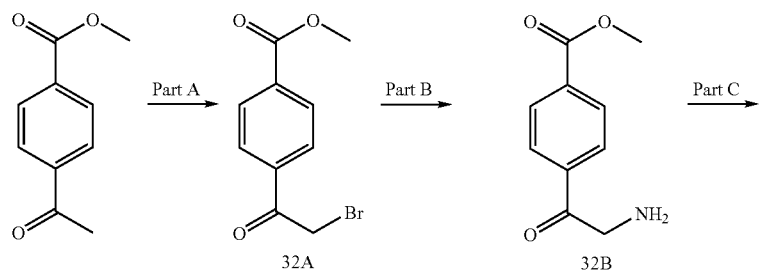

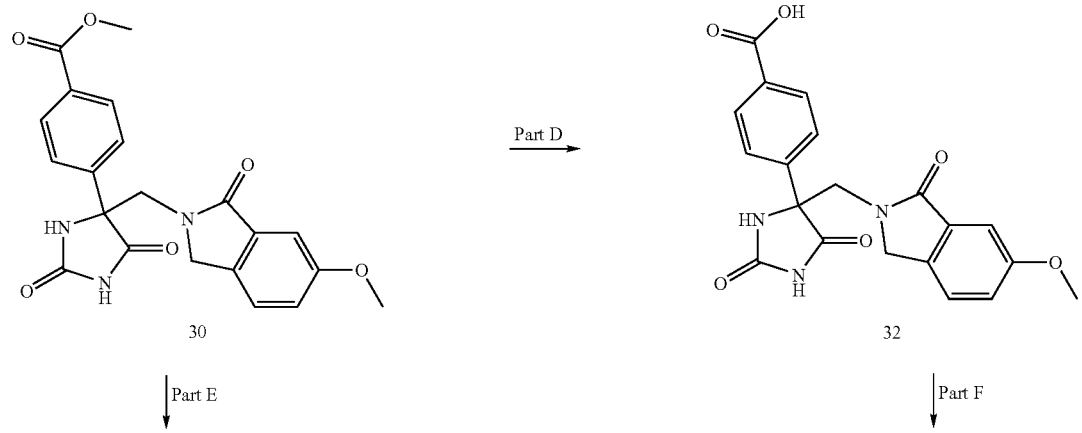

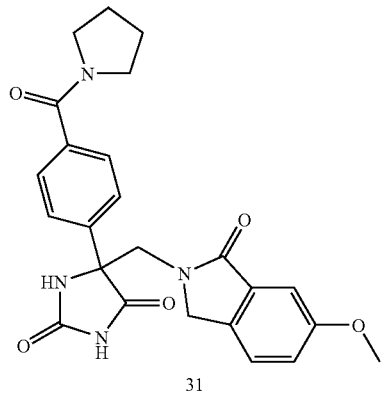

31

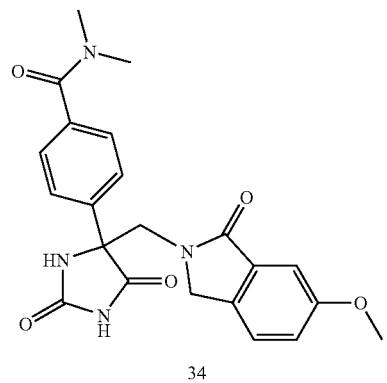

34

Part A

To a solution of methyl 4-acetylbenzoate (1.9 g, 10.6 mmol) in acetic acid (10 mL) was added dropwise bromine (1.7 g, 21.3 mmol). The mixture was heated at 60° C. for 30 min, then stirred at room temperature for 1 hour, and poured into cold water (30 mL). The light yellow precipitate was collected, washed with water and dried (2.6 g, 96%).

Part B

Compound 32A was treated with one equivalent of hexamethylene tetraamine in chloroform for about 1 hour. The product was collected by filtration and then treated with HCl in methanol for 2 hours. The solid was then collected by filtration to give compound 32B.

Part C

Compound 30 was prepared following the procedures described in Example 2 Steps 1, 2, 3 and in Example 30OE Part E: HPLC-MS $t_R$=1.36 min ($UV_{254\ nm}$); mass calculated for formula C21H19N3O6 409.1, observed LCMS m/z 410.1 (M+H).

Part D

Compound 30 (60 mg, 0.147 mmol) was heated in 5% KOH in MeOH (2 mL) at 60° C. overnight, cooled to room temperature and concentrated. The residue was dissolved in water (5 mL), acidified with conc. HCl and filtered. The solid was collected and dried to give compound 32 (23 mg, 40%): HPLC-MS $t_R$=1.04 min ($UV_{254\ nm}$); mass calculated for formula C20H17N3O6 395.1, observed LCMS m/z 396.1 (M+H).

Part E

Compound 30 (39 mg, 0.095 mmol) was heated in pyrrolidine (2 mL) at 60° C. overnight, cooled to room temperature and concentrated. The residue was purified by reverse phase chromatography to give 31: HPLC-MS $t_R$=1.19 min ($UV_{254\ nm}$); mass calculated for formula C24H24N4O5 448.2, observed LCMS m/z 449.2 (M+H).

Part F

A mixture of compound 32 (49 mg, 0.12 mmol), dimethylamine hydrochloride (20 mg, 0.25 mmol), HATU (61 mg, 0.16 mmol), DMAP (2 mg, 0.012 mmol) and diisopropylethylamine (0.065 mL, 0.37 mmol) was stirred in DMF (2 mL) at room temperature overnight. The mixture was diluted with ethyl acetate, washed with 0.1 N HCl, water and brine, dried over sodium sulfate and evaporated. The residue was purified by reverse phase chromatography to give 34: HPLC-MS $t_R$=1.09 min ($UV_{254\ nm}$); mass calculated for formula C22H22N4O5 422.2, observed LCMS m/z 423.1 (M+H).

Example 33

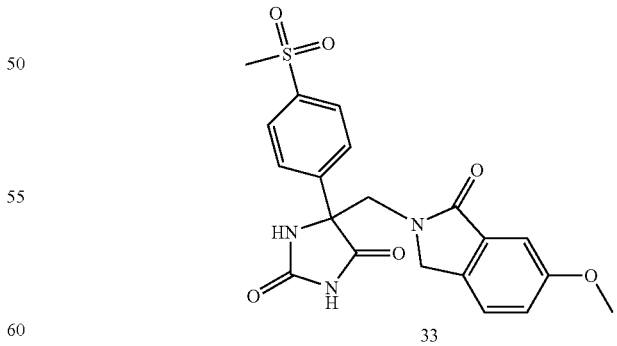

Part A

Compound 33 was prepared from 33A following procedures described in Example 32 Part B and Part C: HPLC-MS $t_R$=1.08 min ($UV_{254\ nm}$); mass calculated for formula C20H19N3O6S 429.1, observed LCMS m/z 430.0 (M+H).

Example 35

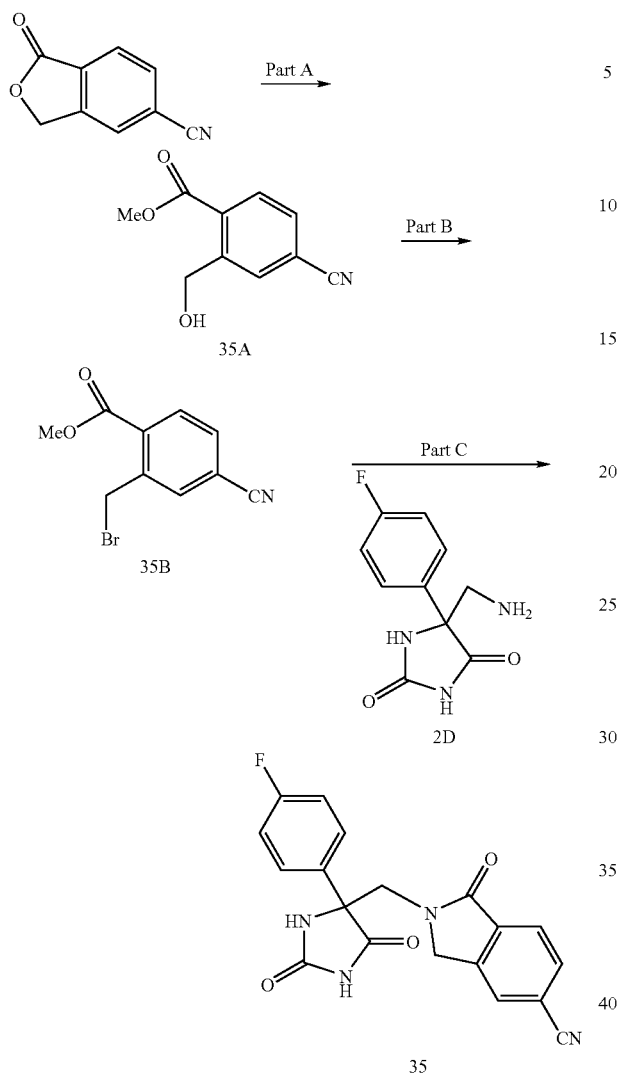

Part A:

A mixture of 5-cyanophthalide (5.0 g, 31.4 mmol) and 1 N of NaOH (31.4 mL) was stirred at 100° C. for 1 h. The solution was concentrated to dryness with azotropic distillation with toluene. The resulting white solid was dissolved in dry DMF (30 mL). Methyl iodide (5.88 mL, 94.2 mmol) was added slowly, and the reaction mixture was allowed to stir at room temperature for 2 h. It was then diluted with $H_2O$ and back extracted with EtOAc (30 mL×4). EtOAc extracts were combined, washed with brine, dried over $Na_2SO_4$, and concentrated. Flash column chromatography on silica (EtOAc/hexane 40:60) gave compound 35A as a white solid (5.5 g, 91%)

Part B:

To compound 35A (5.5 g, 28.77 mmol) in THF (60 mL) was added carbon tetrabromide (11.45 g, 34.52 mmol). The solution was cooled to 0° C. in an ice/water bath, and triphenylphosphine (9.05 g, 34.52 mmol) was added portionwise. The reaction mixture was stirred at room temperature for 3 h under argon. After removing the precipitate by filtration, the solution was concentrated. The residue was dissolved in EtOAc (100 mL), washed with 1 N HCl, $H_2O$, brine, dried over $Na_2SO_4$, and concentrated. Flash column chromatography on silica (EtOAc/hexane 20:80) gave compound 35B as a pale yellow solid (6.8 g, 93%).

Part C:

Compound 35 was prepared using previously described methods from 2D and 35B. HPLC-MS $t_R$=2.943 min ($UV_{254\ nm}$), Mass calculated for formula $C_{19}H_{13}FN_4O_3$ 364.1, observed LCMS m/z 365.0 (M+H).

Example 37

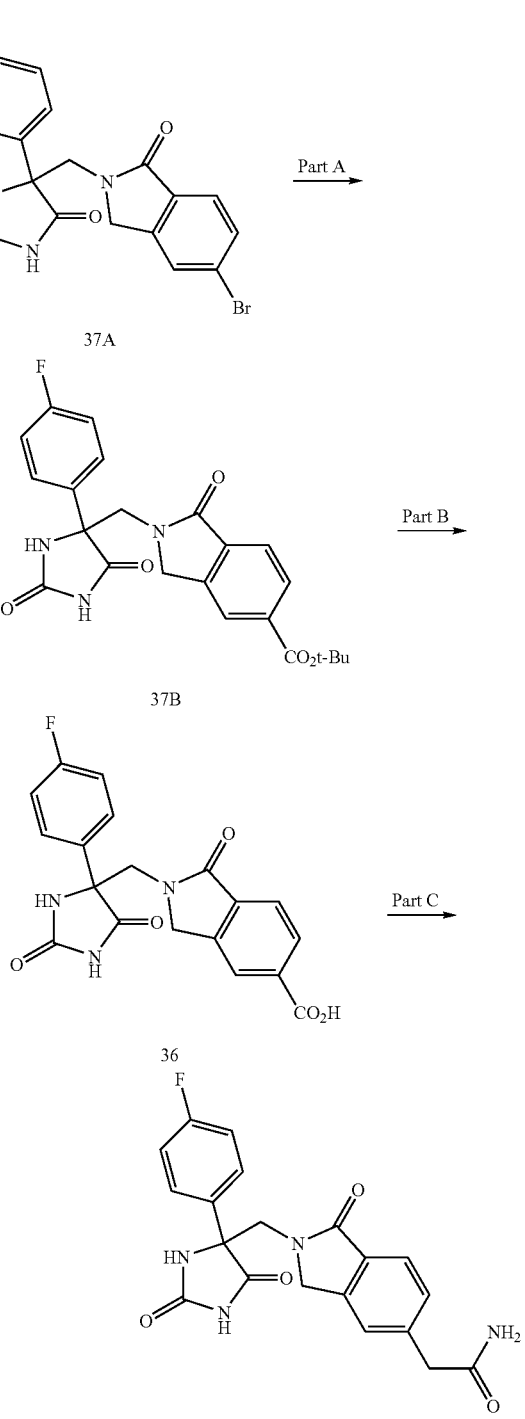

Compound 37A was prepared using procedures described in Example 375.

Part A:

Compound 37A (550 mg, 1.32 mmol) and Pd(t-Bu$_3$P)$_2$ (34 mg, 0.066 mmol, 5 mol %) in NMP (5 mL) were added with a 0.5 M solution of 2-tert-butoxy-2-oxoethylzinc chloride in THF (10.5 mL, 5.2 mmol) under argon. The reaction mixture was allowed to stir at 90° C. overnight. After cooling to room temperature, it was diluted with EtOAc, washed with water, brine, dried over Na$_2$SO$_4$, and concentrated. Column chromatography on silica gel (MeOH/DCM, 10:90) afforded 37B as a pale yellow solid (260 mg, 43%). HPLC-MS (5 min) $t_R$=1.69 min (UV$_{254\ nm}$), Mass calculated for formula C$_{19}$H$_{13}$FN$_4$O$_3$ 453.2, observed LCMS m/z 454.1 (M+H).

Part B:

Compound 37B (40 mg, 0.088 mmol) was treated with TFA in DCM at room temperature to afford 36 as a white solid (20 mg, 27%). HPLC-MS $t_R$=2.64 min (UV$_{254\ nm}$), Mass calculated for formula C$_{20}$H$_{16}$FN$_3$O$_5$ 397.1, observed LCMS m/z 398.0 (M+H).

Part C:

Compound 36 (20 mg, 0.05 mmol) in DMF (1 mL) was added with HOBt (14 mg, 0.1 mmol) and EDC (19 mg, 0.1 mmol). After stirring at room temperature for 10 min, NH$_4$Cl (20 mg, 0.15 mol) was added, followed by the addition of DIEA (0.026 mL). The reaction mixture was then stirred at room temperature overnight. It was diluted with EtOAc, washed with 1 N HCl, saturated NaHCO$_3$, and brine, dried over Na$_2$SO$_4$, and concentrated. Recrystallization in EtOAc gave 37 (7.4 mg, 37%) as a white solid. HPLC-MS $t_R$=2.64 min (UV$_{254\ nm}$), Mass calculated for formula C$_{20}$H$_{17}$FN$_4$O$_4$ 396.1, observed LCMS m/z 397.1 (M+H).

NMR spectral data for the some of the above compounds are provided below:

Compound 50. $^1$H NMR (500 Hz, CD$_3$OD) δ 8.27 (d, 1H, J=8.6 Hz), 8.14 (d, 1H, J=8.6 Hz), 7.45 (d, 1H, J=8.3 Hz), 7.37 (s, 1H), 7.29 (d, 1H, J=2.5 Hz), 7.20 (dd, 1H, J=8.3 Hz, 2.5 Hz), 4.56 (d, 1H, J=8.7 Hz), 4.53 (d, 1H, J=8.7 Hz), 4.50 (d, 1H, J=12.5 Hz), 4.46 (d, 1H, J=12.6 Hz), 3.87 (s, 3H), 3.30 (s, 3H).

Compound 98. $^1$H NMR (400 Hz DMSO-d$_6$) δ (ppm): 11.24 (s, 1H), 8.97 (s, 1H), 8.80 (d, J=2.01 Hz, 1H), 8.57 (d, J=2.46 Hz, 1H), 8.17 (s, 1H), 7.60 (s, 1H), 7.49 (d, J=8.19 Hz, 1H), 7.24 (s, 1H), 7.17-7.14 (m, 2H), 4.46-4.25 (m, 4H), 3.79 (s, 3H).

Compound 68. $^1$H NMR (500 Hz, CD$_3$OD) δ 8.42 (s, 1H), 8.32 (d, 1H, J=2.1 Hz), 7.79 (d, 2H, J=8.5 Hz), 7.74 (d, 2H, J=8.5 Hz), 7.42 (d, 1H, J=8.4 Hz), 7.28-7.32 (m, 1H), 7.19 (dd, 1H, J=8.4, 2.5 Hz), 4.32-4.46 (m, 3H), 4.24 (d, 1H, J=14.2 Hz), 3.87 (s, 3H).

Compound 66. $^1$H NMR (500 Hz, CD$_3$OD) δ 8.88 (d, 1H, J=5.0 Hz), 8.30 (s, 1H), 8.19 (d, 2H, J=8.5 Hz), 7.88 (d, 2H, J=8.2 Hz), 7.67 (dd, 1H, J=5.1, 1.3 Hz), 7.41 (d, 1H, J=8.6 Hz), 7.31 (d, 1H, J=2.5 Hz), 7.19 (dd, 1H, J=8.2, 2.5 Hz), 4.34-4.47 (m, 3H), 4.26 (d, 1H, J=14.7 Hz), 3.87 (s, 3H).

Compound 64. $^1$H NMR (500 Hz, CD$_3$OD) δ 8.10 (d, 2H, J=8.5 Hz), 7.99 (s, 1H), 7.84 (d, 2H, J=8.5 Hz), 7.56 (s, 1H), 7.37 (d, 1H, J=8.2 Hz), 7.27 (d, 1H, J=2.7 Hz), 7.15 (dd, 1H, J=8.4, 2.5 Hz), 4.28-4.43 (m, 3H), 4.24 (d, 1H, J=14.5 Hz), 3.84 (s, 3H), 2.65 (s, 3H), 0.84-0.89 (m, 1H), 0.69-0.74 (m, 2H), 0.49-0.52 (m, 2H).

Compound 97. $^1$H NMR (500 MHz, MeOH-d$_4$) δ 8.19 (s, 1H), 7.83 (s, 1H), 7.66-7.70 (m, 1H), 7.55-7.58 (m, 1H), 7.41-7.44 (m, 1H), 7.29-7.32 (m, 1H), 7.17-7.21 (m, 1H), 7.07 (s, 1H), 4.35-4.55 (m, 4H), 3.87 (s, 3H).

Compound 85. $^1$H NMR (500 MHz, MeOH-d$_4$) δ 7.70-7.75 (m, 2H) 7.65-7.70 (m, 1H), 7.41-7.56 (m, 3H), 7.28-7.31 (m, 1H), 7.17-7.23 (m, 2H), 7.08-7.13 (m, 2H), 4.29-4.47 (m, 3H), 4.15-4.24 (m, 1H), 3.87 (s, 3H).

Compound 84. $^1$H NMR (500 MHz, MeOH-d$_4$) δ 7.80-7.88 (m, 2H), 7.70-7.78 (m, 2H) 7.38-7.46 (m, 1H), 7.26-7.33 (m, 1H), 7.16-7.24 (m, 1H), 7.08-7.15 (m, 2H), 6.98-7.06 (m, 2H), 4.29-4.46 (m, 3H), 4.15-4.26 (m, 1H), 3.87 (s, 3H), 2.93 (s, 3H).

Compound 43 (400 Hz DMSO-d6) δ 8.99 (s, 1H), 7.98 (dd, J=14.8 Hz, 2 Hz, 2H), 7.90 (dd, J=14.8 Hz, 2 Hz, 2H), 7.47 (d, J=8.4 Hz, 1H), 7.14 (m, 2H), 4.26 (m, 3H), 4.08 (m, 1H), 3.79 (s, 3H), 3.22 (s, 3H).

Compound 76. $^1$H NMR (500 MHz, DMSO-d$_6$) δ 10.97 (s, 1H), 9.00 (d, J=2.0 Hz, 1H), 8.39 (d, J=8.5 Hz, 1H), 8.22 (d, J=7.5 Hz, 1H), 8.08 (t, J=7.5 Hz, 1H), 8.00 (d, J=7.5 Hz, 1H), 7.78 (d, J=8.5 Hz, 1H), 7.75 (br. s, 1H), 7.48 (d, J=8.5 Hz, 1H), 7.19 (d, J=2.5 Hz, 1H), 7.16 (dd, J=8.5, 2.5 Hz, 1H), 4.34 (d, J=17.5 Hz, 1H), 4.26 (d, J=17.5 Hz, 1H), 4.24 (d, J=14.5 Hz, 1H), 4.17 (d, J=14.5 Hz, 1H), 3.81 (s, 3H).

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Each document referred to herein is incorporated by reference in its entirety for all purposes.

We claim:

1. A compound represented by Formula (I):

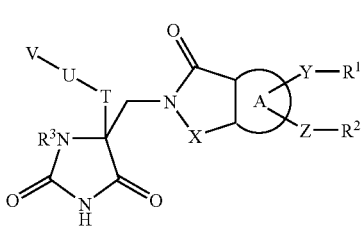

or a pharmaceutically acceptable salt or ester thereof, wherein:

ring A is phenyl which is substituted with —Y—R$^1$ and -Z-R$^2$ as shown;

X is —(C(R$^3$)$_2$)$_m$—;

T is absent;

U is absent;

V is

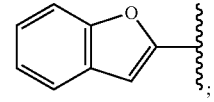

which is unsubstituted or substituted with one to four R$^{10}$ moieties which can be the same or different;

Y is selected from the group consisting of a covalent bond, —(C(R$^4$)$_2$)$_n$—, —N(R$^4$)—, —C(O)N(R$^4$)—, —N(R$^4$)C(O)—, —N(R$^4$)C(O)N(R$^4$)—, —S(O)$_2$N(R$^4$)—, —N(R$^4$)—S(O)$_2$—, —O—, —S—, —C(O)—, —S(O)—, and —S(O)$_2$—;

Z is selected from the group consisting of a covalent bond, —(C(R$^4$)$_2$)$_n$—, —N(R$^4$)—, —C(O)N(R$^4$)—, —N(R$^4$)C(O)—, —N(R$^4$)C(O)N(R$^4$)—, —S(O)$_2$N(R$^4$)—, —N(R$^4$)—S(O)$_2$—, —O—, —S—, —C(O)—, —S(O)—, and —S(O)$_2$—;

m is 1;

n is 1 to 3;

R$^1$ is selected from the group consisting of H, cyano, —C(O)OH, —C(O)O-alkyl, —C(O)NH$_2$, —C(O)NH (alkyl), —C(O)N(alkyl)$_2$, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the R$^1$ alkyl, alkynyl, aryl, heteroaryl, and heterocyclyl, optionally with the five-to eight-membered cycloalkyl, aryl, heterocyclyl or heteroaryl ring is unsubstituted or optionally independently substituted with one to four R$^{20}$ moieties which can be the same or different; with the proviso that when Y is —N(R$^4$)—, —S— or —O—, then R$^1$ is not halogen or cyano;

R$^2$ is selected from the group consisting of H, cyano, —C(O)OH, —C(O)O-alkyl, —C(O)NH$_2$, —C(O)NH(alkyl), —C(O)N(alkyl)$_2$, alkynyl, halogen, alkyl, cycloalkyl, haloalkyl, aryl, heteroaryl, and heterocyclyl, wherein when each of said cycloalkyl, heterocyclyl, aryl and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of the R$^2$ alkyl, cycloalkyl, aryl, heteroaryl, and heterocyclyl, optionally with the five-to eight-membered, aryl, heterocyclyl or heteroaryl ring is unsubstituted or optionally independently substituted with one to four R$^{20}$ moieties which can be the same or different; with the proviso that when Z is —N(R$^4$)—, —S— or —O—, then R$^2$ is not halogen or cyano;

each R$^3$ is the same of different and is independently selected from the group consisting of H, and alkyl;

each R$^4$ is the same or different and is independently selected from the group consisting of H, alkyl, cycloalkyl, haloalkyl, hydroxy, -alkylcycloalkyl, -alkyl-N(alkyl)$_2$, heterocyclyl, aryl, and heteroaryl, wherein when each of said cycloalkyl, heterocyclyl, aryl, and heteroaryl contains two radicals on adjacent carbon atoms, said radicals may optionally be taken together with the carbon atoms to which they are attached to form a five- to eight-membered cycloalkyl, aryl, heterocyclyl or heteroaryl ring;

R$^{10}$ is selected from the group consisting of hydrogen, cyano, nitro, —C(R$^4$)=N—OR$^4$, —OR$^4$, —SR$^4$, —N(R$^4$)$_2$, —S(O)R$^4$, —S(O)$_2$R$^4$, —N(R$^4$)S(O)$_2$R$^4$, —N(R$^4$)—C(O)—R$^4$, —N(R$^4$)—C(O)—N(R$^4$)$_2$, —N(R$^4$)—C(O)—OR$^4$, —OC(O)N(R$^4$)$_2$, —C(O)N(R$^4$)—S(O)$_2$R$^4$, —S(O)$_2$N(R$^4$)—C(O)—R$^4$, —C(O)N(R$^4$)C(O)R$^4$, —C(O)N(R$^4$)C(O)NR$^4$, —S(O)$_2$N(R$^4$)$_2$, —N(R$^4$)—C(=NR$^4$)—N(R$^4$)$_2$, —N(R$^4$)—C(=N—CN)—N(R$^4$)$_2$, -haloalkoxy, —C(O)OR$^4$, —C(O)R$^4$, —C(O)N(R$^4$)$_2$, halogen, alkyl, haloalkyl, aryl, heteroaryl, heterocyclyl, and cycloalkyl, wherein each of the R$^{10}$ alkyl, aryl, heteroaryl, heterocyclyl, and cycloalkyl is unsubstituted or optionally independently substituted with one to four R$^{30}$ moieties which can be the same or different;

or wherein two R$^{10}$ moieties, when attached to the same or adjacent carbon atoms may optionally be taken together with the carbon atom(s) to which they are attached to form a cycloalkyl, cycloalkenyl, heterocyclyl, aryl, or heteroaryl ring;

R$^{20}$ is selected from the group consisting of cyano, nitro, —C(R$^4$)=N—OR$^4$, —OR$^4$, —SR$^4$, —N(R$^4$)$_2$, —S(O)R$^4$, —S(O)$_2$R$^4$, —N(R$^4$)S(O)$_2$R$^4$, —N(R$^4$)—C(O)—R$^4$, —N(R$^4$)—C(O)—N(R$^4$)$_2$, —N(R$^4$)—C(O)—OR$^4$, —OC(O)N(R$^4$)$_2$, —C(O)N(R$^4$)—S(O)$_2$R$^4$, —S(O)$_2$N(R$_4$)—C(O)—R$^4$, —C(O)N(R$^4$)C(O)R$^4$, —C(O)N(R$^4$)C(O)NR$^4$, —S(O)$_2$N(R$^4$)$_2$, —N(R$^4$)—C(=NR$^4$)—N(R$^4$)$_2$, —N(R$^4$)—C(=N—CN)—N(R$^4$)$_2$, -haloalkoxy, —C(O)OR$^4$, —C(O)R$^4$, —C(O)N(R$^4$)$_2$, halogen, alkyl, haloalkyl, aryl, heteroaryl, heterocyclyl, and cycloalkyl; wherein when each of said R$^{20}$ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said R$^{20}$ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, hydroxyalkyl, cyano, nitro, —NH$_2$, —NH(alkyl), and —N(alkyl)$_2$;

or when two R$^{20}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

R$^{30}$ is selected from the group consisting of cyano, nitro, —C(R$^4$)=N—OR$^4$, —OR$^4$, —SR$^4$, —N(R$^4$)$_2$, —S(O)R$^4$, —S(O)$_2$R$^4$, —N(R$^4$)S(O)$_2$R$^4$, —N(R$^4$)—C(O)—R$^4$, —N(R$^4$)—C(O)—N(R$^4$)$_2$, —N(R$^4$)—C(O)—OR$^4$, —OC(O)N(R$^4$)$_2$, —C(O)N(R$^4$)—S(O)$_2$R$^4$, —S(O)$_2$N(R$_4$)—C(O)—R$^4$, —C(O)N(R$^4$)C(O)R$^4$, —C(O)N(R$^4$)C(O)NR$^4$, —S(O)$_2$N(R$^4$)$_2$, —N(R$^4$)—C(=NR$^4$)—N(R$^4$)$_2$, —N(R$^4$)—C(=N—CN)—N(R$^4$)$_2$, -haloalkoxy, —C(O)OR$^4$, —C(O)R$^4$, —C(O)N(R$^4$)$_2$, halogen, alkyl, haloalkyl, aryl, heteroaryl, heterocyclyl, and cycloalkyl; wherein when each of said R$^{30}$ aryl, heteroaryl, heterocyclyl and cycloalkyl contains two radicals on adjacent carbon atoms, said radicals may optionally be taken together with the carbon atoms to which they are attached to form a five- to eight-membered cycloalkyl, aryl, heterocyclyl or heteroaryl ring; wherein each of said R$^{30}$ alkyl, aryl, heteroaryl, heterocyclyl, and cycloalkyl, optionally with said five- to eight-membered cycloalkyl, aryl, heterocyclyl or heteroaryl ring is unsubstituted or substituted with one to four moieties selected independently from the group consisting of alkyl, halo, haloalkyl, hydroxy, alkoxy, haloalkoxy, cyano, nitro, —NH$_2$, —NH(alkyl), and —N(alkyl)$_2$;

or when two R$^{30}$ moieties when attached to the same or adjacent carbon atoms may optionally be taken together with the carbon atom(s) to which they are attached to form a cycloalkyl, cycloalkenyl, heterocyclyl, aryl, or heteroaryl ring;

with the proviso that at least one of conditions (1)-(2) below are satisfied:

(1) V is substituted with at least one R$^{10}$ moiety selected from the group consisting of cyano, —C(O)OR$^4$, —C(O)R$^4$, —C(O)N(R$^4$)$_2$, —C(O)N(R$^4$)C(O)R$^4$,—C(O)N(R$^4$)C(O)NR$^4$, —SR$^4$, —S(O)$_2$R$^4$, —N(R$^4$)—C(O)OR$^4$, —OC(O)N(R$^4$)$_2$, —N(R$^4$)C(O)N(R$^4$)$_2$, —N(R$^4$)—C(O)—R$^4$, —S(O)$_2$N(R$^4$)$_2$, —S(O)$_2$N(R$_4$)—C(O)—R$^4$, —N(R$^4$)—C(=NR$^4$)—N(R$^4$)$_2$, —N(R$^4$)—C(=N—CN)—N(R$^4$)$_2$, and —C(R$^4$)=N—OR$^4$, wherein each R$^4$ independently is selected from the group consisting of H, alkyl, cycloalkyl, heterocyclyl, aryl, and heteroaryl, wherein when each of said R$^4$ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring;

(2) each of —Y—R¹ and -Z-R² is independently selected from the group consisting of cyano, —(C(R⁴)₂)ₙ—C(O)OH, —(C(R⁴)₂)ₙ—C(O)O-alkyl, —(C(R⁴)₂)ₙ—C(O)NH₂, —(C(R⁴)₂)ₙ—C(O)NH(alkyl), and —(C(R⁴)₂)ₙ—C(O)N(alkyl)₂, wherein each R⁴ independently is H or alkyl; and n is 1-3.

2. The compound of claim 1, wherein R³ is H.

3. The compound of claim 1, wherein said V is substituted with at least one R¹⁰ moiety selected from the group consisting of cyano, —C(O)OR⁴, —C(O)R⁴, —C(O)N(R⁴)₂, —C(O)N(R⁴)C(O)R⁴, —C(O)N(R⁴)C(O)NR⁴, —SR⁴, —S(O)₂R⁴, —N(R⁴)—C(O)OR⁴, —OC(O)N(R⁴)₂, —N(R⁴)C(O)N(R⁴)₂, —N(R⁴)—C(O)—R⁴, —S(O)₂N(R⁴)₂, —S(O)₂N(R₄)—C(O)—R⁴, —N(R⁴)—C(=NR⁴)—N(R⁴)₂, —N(R⁴)—C(=N—CN)—N(R⁴)₂, and —C(R⁴)=N—OR⁴, wherein each R⁴ independently is selected from the group consisting of H, alkyl, cycloalkyl, heterocyclyl, aryl, and heteroaryl, wherein when each of said R⁴ cycloalkyl, heterocyclyl, aryl, and heteroaryl contains two radicals on adjacent carbon atoms, said radicals may optionally be taken together with the carbon atoms to which they are attached to form a five- to eight-membered aryl, heterocyclyl, heteroaryl or cycloalkyl ring.

4. The compound of claim 3, wherein said V is substituted with at least one R¹⁰ moiety selected from the group consisting of cyano, —C(O)OR⁴, —C(O)R⁴, —C(O)N(R⁴)₂, and —C(R⁴)=N—OR⁴.

5. The compound of claim 3, wherein said V is substituted with at least one R¹⁰ moiety that is cyano.

6. The compound of claim 3, wherein said V is substituted with at least one R¹⁰ moiety that is —SR⁴.

7. The compound of claim 3, wherein said V is substituted with at least one R¹⁰ moiety that is —S(O)₂R⁴.

8. The compound of claim 3, wherein said V is substituted with at least one R¹⁰ moiety that is —S(O)₂N(R⁴)₂.

9. The compound of claim 3, wherein each of Y and Z is independently selected from the group consisting of a covalent bond and —O—.

10. The compound of claim 9, wherein Y is —O— and Z is a covalent bond.

11. The compound of claim 3, wherein each of R¹ and R² is independently selected form the group consisting of H and alkyl.

12. The compound of claim 11, wherein R¹ is alkyl and R² is H.

13. The compound of claim 12, wherein R¹ is methyl.

14. The compound of claim 3, selected from the group consisting of:

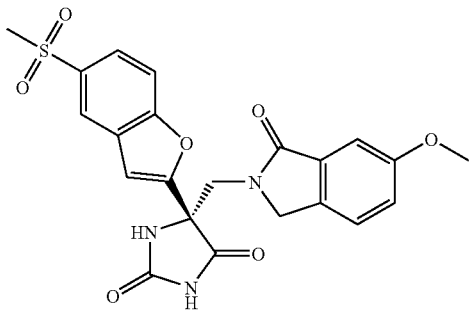

and

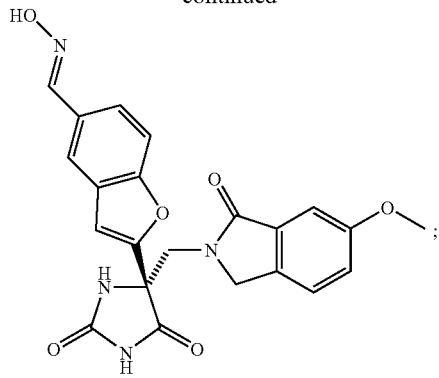

or a pharmaceutically acceptable salt or ester thereof.

15. The compound of claim 1, wherein each of —Y—R¹ and -Z-R² is independently selected from the group consisting of cyano, —(C(R⁴)₂)ₙ—C(O)OH, —(C(R⁴)₂)ₙ—C(O)O-alkyl, —(C(R⁴)₂)ₙ—C(O)NH₂, —(C(R⁴)₂)ₙ—C(O)NH(alkyl), and —(C(R⁴)₂)ₙ—C(O)N(alkyl)₂, wherein each R⁴ independently is H or alkyl; and n is 1-3.

16. The compound of claim 15, wherein n is 1.

17. A compound selected from the group consisting of:

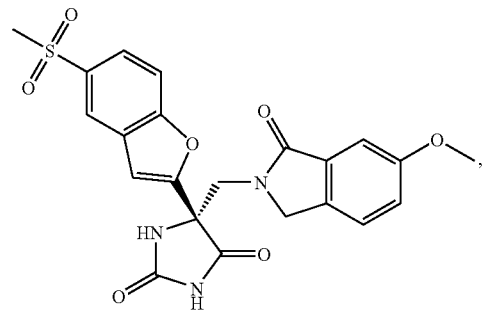

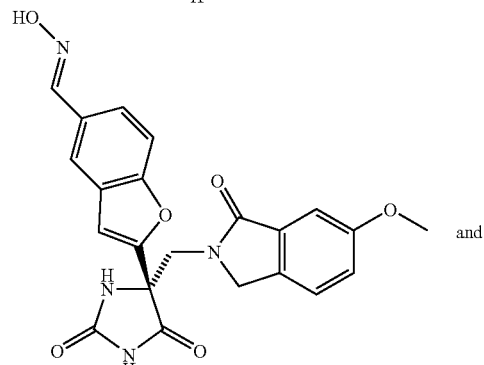

and

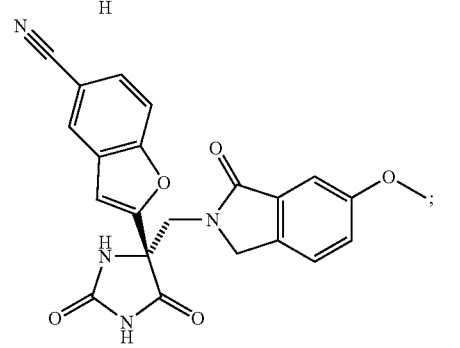

or a pharmaceutically acceptable salt or ester thereof.

18. A pharmaceutical composition comprising the compound of claim 1 or a pharmaceutically acceptable salt or ester thereof, and at least one pharmaceutically acceptable carrier.

19. A pharmaceutical composition comprising the compound of claim 17 or a pharmaceutically acceptable salt or ester thereof, and at least one pharmaceutically acceptable carrier.

* * * * *